(12) United States Patent
Cheng et al.

(10) Patent No.: US 11,564,889 B2
(45) Date of Patent: Jan. 31, 2023

(54) STEM CELL BIOMIMETIC MICROPARTICLES

(71) Applicant: North Carolina State University, Raleigh, NC (US)

(72) Inventors: Ke Cheng, Raleigh, NC (US); Junnan Tang, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 202 days.

(21) Appl. No.: 16/337,635

(22) PCT Filed: Sep. 28, 2017

(86) PCT No.: PCT/US2017/053982
§ 371 (c)(1),
(2) Date: Mar. 28, 2019

(87) PCT Pub. No.: WO2018/064315
PCT Pub. Date: Apr. 5, 2018

(65) Prior Publication Data
US 2020/0030243 A1    Jan. 30, 2020

Related U.S. Application Data

(60) Provisional application No. 62/405,411, filed on Oct. 7, 2016, provisional application No. 62/401,272, filed on Sep. 29, 2016.

(51) Int. Cl.
| | | |
|---|---|---|
| *A61K 9/50* | (2006.01) | |
| *A61K 9/00* | (2006.01) | |
| *A61K 9/10* | (2006.01) | |
| *A61K 35/28* | (2015.01) | |
| *A61K 38/18* | (2006.01) | |
| *A61K 47/34* | (2017.01) | |

(52) U.S. Cl.
CPC .......... *A61K 9/5089* (2013.01); *A61K 9/0019* (2013.01); *A61K 9/10* (2013.01); *A61K 9/5031* (2013.01); *A61K 9/5068* (2013.01); *A61K 35/28* (2013.01); *A61K 38/18* (2013.01); *A61K 47/34* (2013.01)

(58) Field of Classification Search
CPC ................ A61K 35/28; A61K 35/34
See application file for complete search history.

(56) References Cited

U.S. PATENT DOCUMENTS

| 2003/0166867 A1 | 9/2003 | Merx et al. |
| 2013/0337066 A1* | 12/2013 | Zhang ...................... A61K 9/14 424/489 |
| 2015/0335788 A1 | 11/2015 | Xia et al. |
| 2019/0336444 A1* | 11/2019 | Fedorchak ............. A61K 9/107 |

FOREIGN PATENT DOCUMENTS

| CN | 103857387 A | 6/2014 |
| EP | 2548569 A1 | 1/2013 |
| RU | 2531046 C2 | 10/2014 |

OTHER PUBLICATIONS

Omar Qutachi, Delivery of definable number of drug or growth factor loaded poly(DL-lactic acid-co-glycolic acid) microparticles within human embryonic stem cell derived aggregates, Journal of Controlled Release 168 (2013) 18-27 (Year: 2013).*
Ramin Khanabdali, Harnessing the secretome of cardiac stem cells as therapy for ischemic heart disease, Biochemical Pharmacology 113 (2016) 1-11, publication date: Feb. 21, 2016 (Year: 2016).*
International Search Report and Written Opinion for PCT/US2017/053982 dated Dec. 21, 2017.
China National Intellectual Property Administration (CNIPA) Office Action for 2017800740385 dated Jan. 26, 2021.

* cited by examiner

*Primary Examiner* — Mark V Stevens
*Assistant Examiner* — Alparslan Asan
(74) *Attorney, Agent, or Firm* — Peter J. Schlueter; Casimir Jones, S.C.

(57) ABSTRACT

Provided are stem cell biomimetic microparticles comprised of at least one stem cell-derived paracrine polypeptide or growth factor embedded in a polymer core particle that further comprises an outer layer of at least one fragment of a cell membrane of a stem cell disposed on the core particle. The polymer core may be constituted of any biocompatible and biodegradable polymer or copolymer, or a combination thereof that allows the embedding of the paracrine factors and their prolonged release from the core. The core and hence the microparticles can be biodegradable, allowing eventual elimination from the recipient animal or human subject. The core particles are sized to allow both transport through blood vessels and extravasation from the blood vessels into the surrounding tissues. The core particle may further include at least one polypeptide or peptide growth factor to induce the generation and proliferation of a population of stem cells.

9 Claims, 35 Drawing Sheets

DAPI alpha-SA (cardiomyocytes) ki67

DAPI alpha-SA (cardiomyocytes) microparticle ( ) = microparticles with synchronized beating

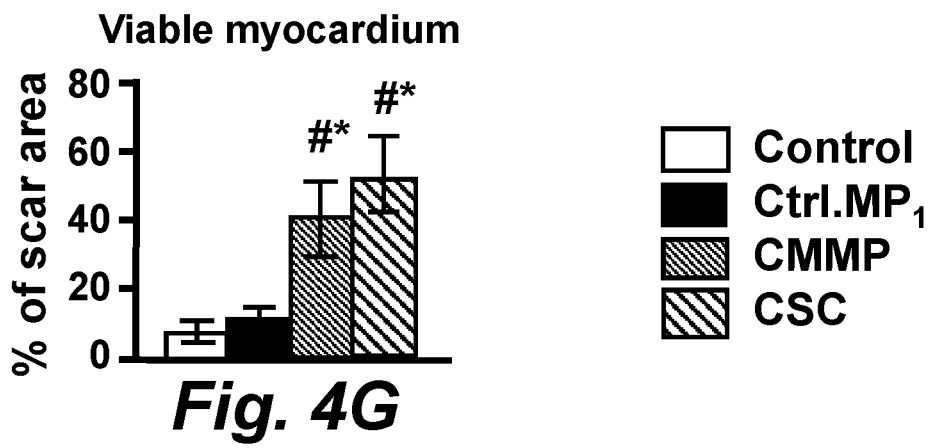
Fig. 4G
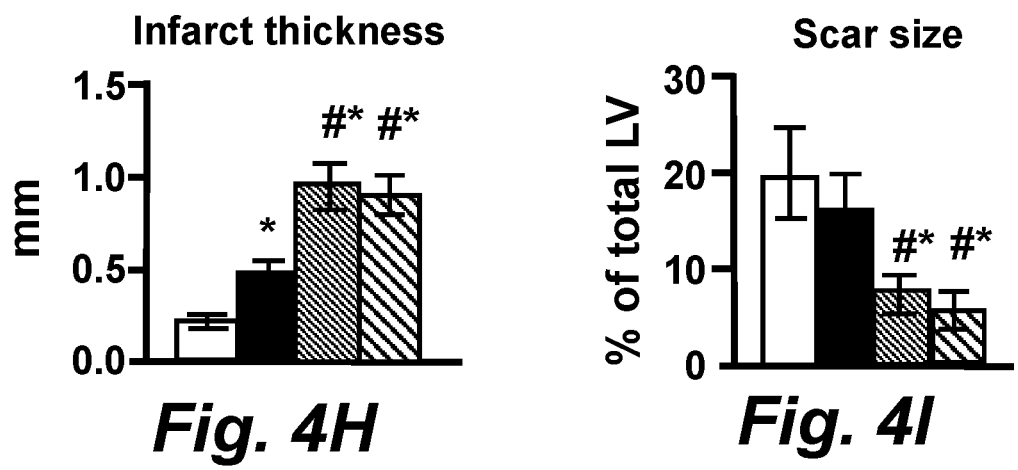
Fig. 4H
Fig. 4I
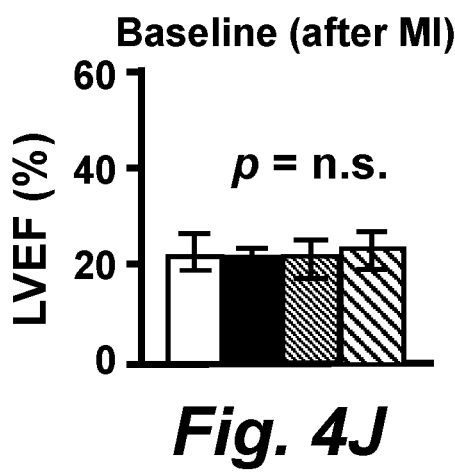
Fig. 4J
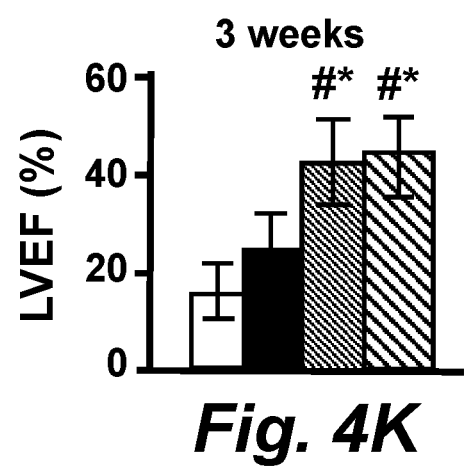
Fig. 4K BV = blood vessel    P = parenchyma

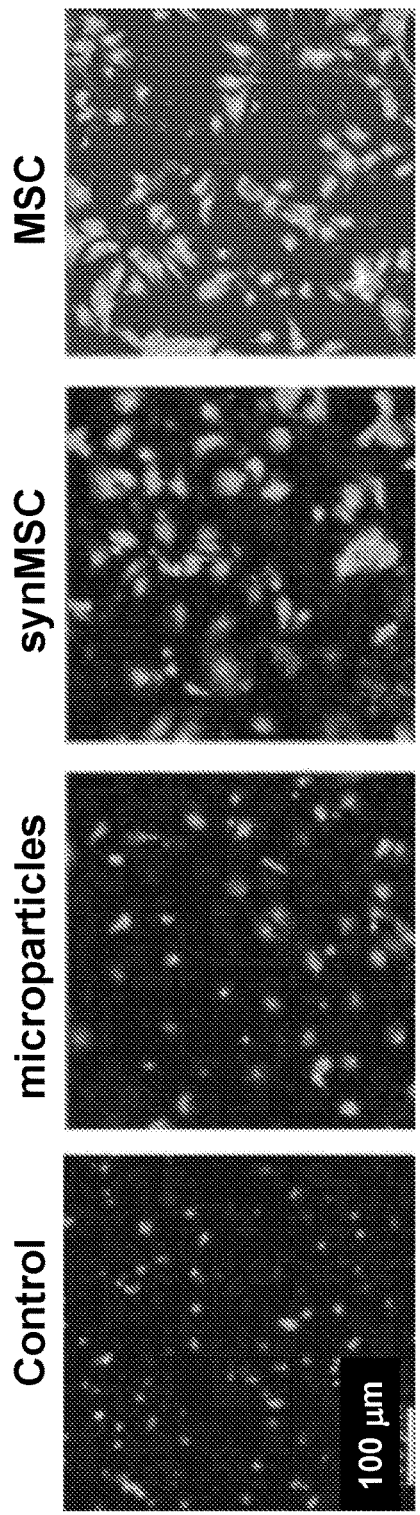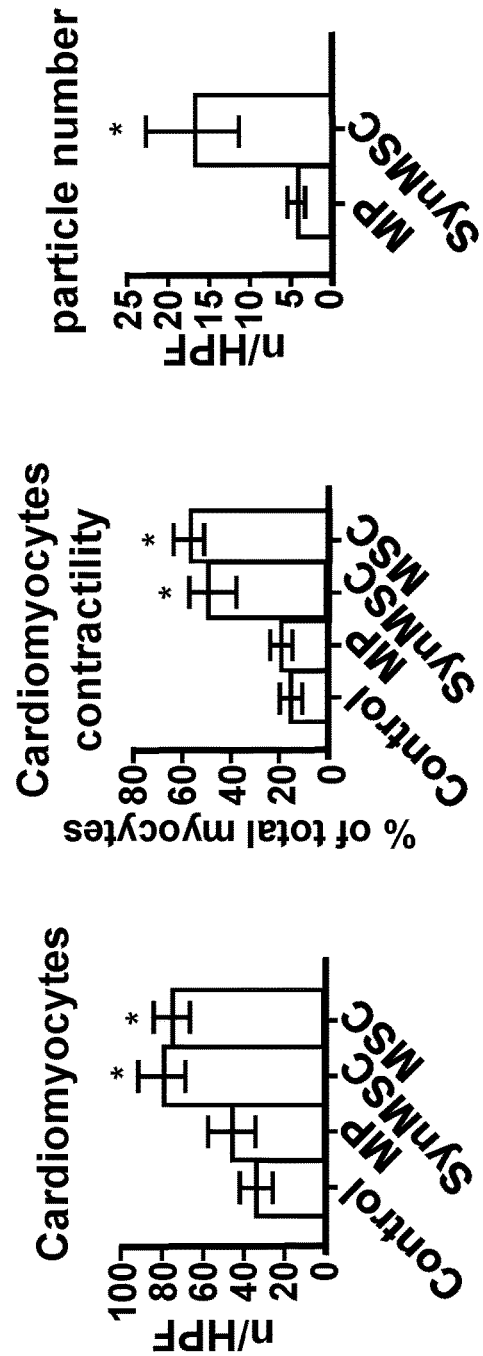
Fig. 15A
Fig. 15B
Fig. 15C
Fig. 15D

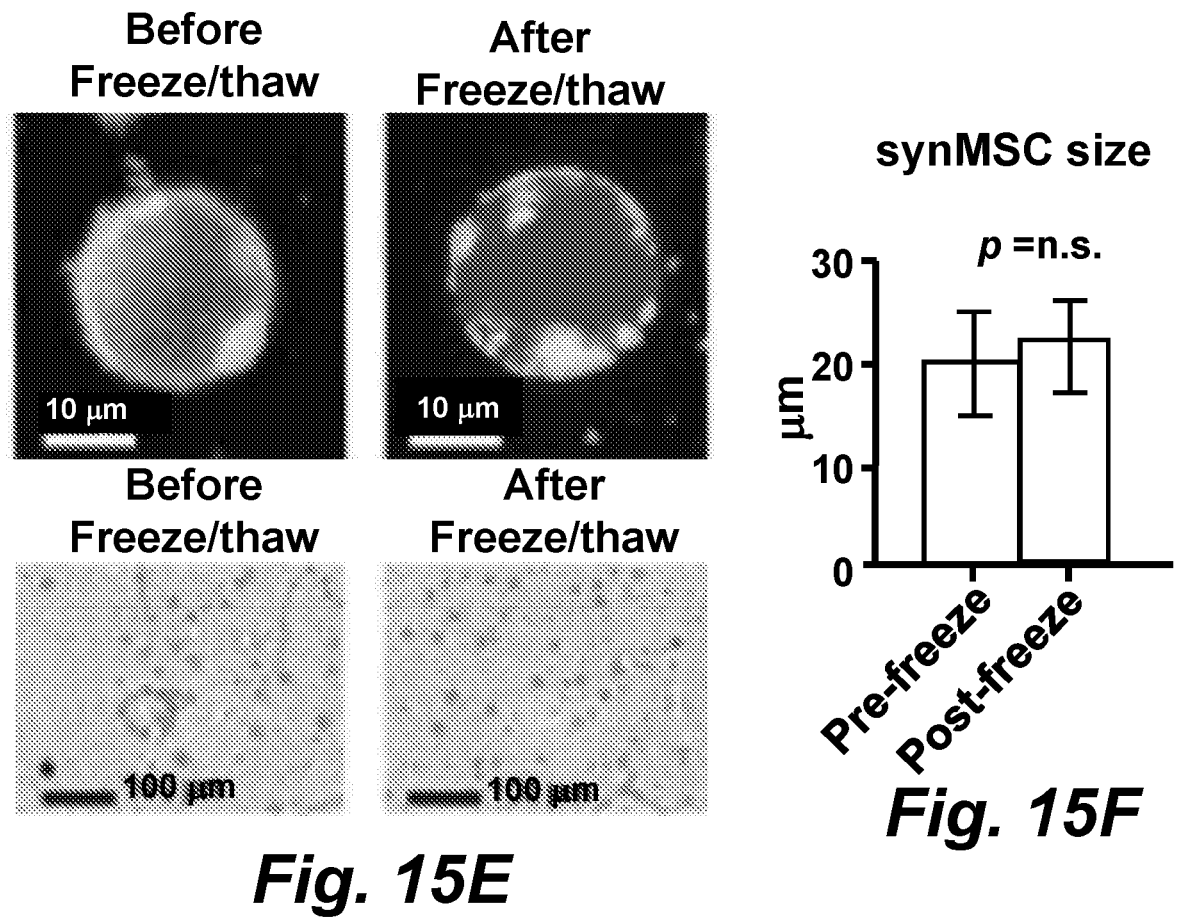
Fig. 15E
Fig. 15F
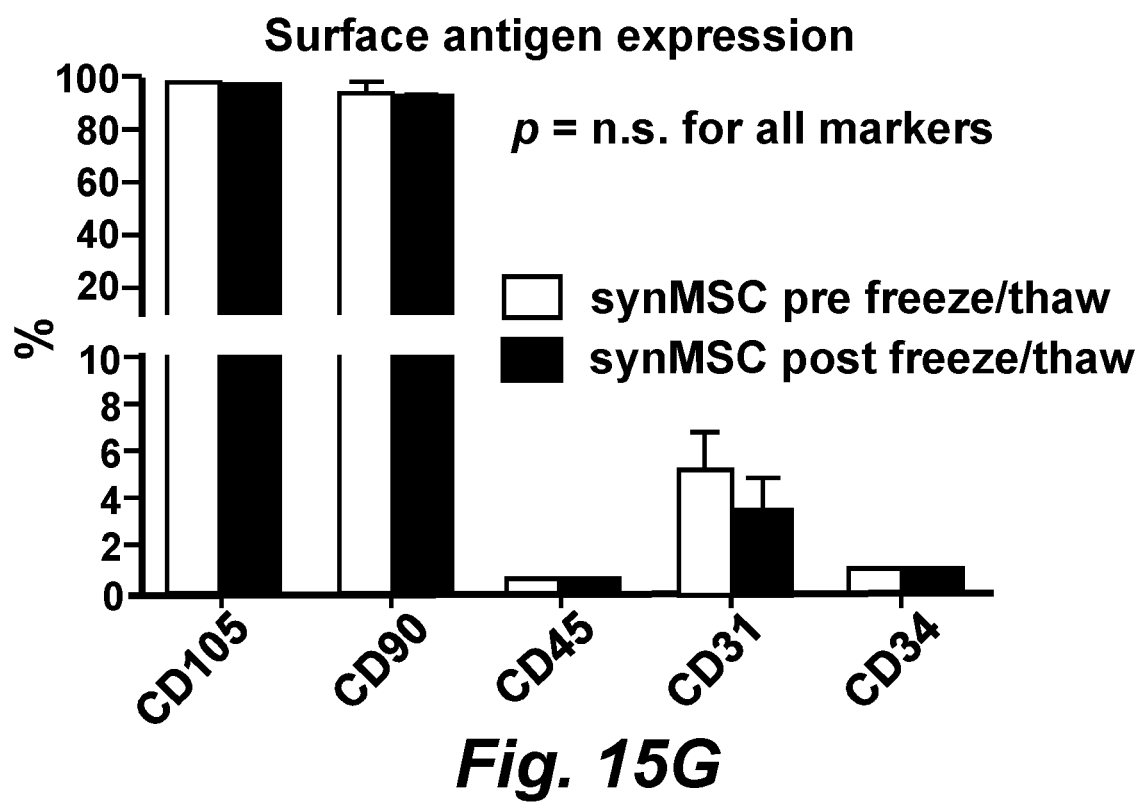
Fig. 15G

STEM CELL BIOMIMETIC MICROPARTICLES

CROSS-REFERENCE TO RELATED APPLICATIONS

This application is the 35 U.S.C. 5371 national stage application of PCT Application No. PCT/US2017/053982, filed on Sep. 28, 2017, where the PCT claims priority from U.S. Provisional Patent Application Ser. No. 62/401,272 entitled "STEM CELL BIOMIMETIC MICROPARTICLES" filed on Sep. 29, 2016 and from U.S. Provisional Patent Application Ser. No. 62/405,411 entitled "STEM CELL BIOMIMETIC MICROPARTICLES" filed on Oct. 7, 2016, both of which are herein incorporated by reference in their entireties.

STATEMENT REGARDING FEDERALLY SPONSORED RESEARCH OR DEVELOPMENT

This invention was made with government support under grant number HL123920 awarded by the National Institutes of Health. The government has certain rights in this invention.

TECHNICAL FIELD

The present disclosure is generally related to stem cell biomimetic microparticles. The present disclosure is also generally related to methods of manufacture and the use of the stem cell biomimetic microparticles for tissue repair.

BACKGROUND

Multiple types of adult stem cells such as mesenchymal stem cells, cardiac stem cells, and endothelial progenitor cells have entered clinical investigations worldwide (Makkar et al., (2012) Lancet 379: 895-904; Bolli et al., (2011) Lancet 378: 1847-1857; Malliaras et al., (2014) J. Am. Coll. Cardiol. 63: 110-122; Chen et al., (2004) Am. J. Cardiol. 94: 92-95; Cheng et al., (2014) J. Am. Heart. Assoc. 3: e001260; Katritsis et al., (2005) Catheter Cardiovasc. Interv. 65: 321-329). Differentiation of injected cells into the host tissues has been reported. However, these sporadic events could not explain the therapeutic benefits seen in animal models and human trials (Bai et al., (2010) Eur. Heart J. 31: 489-501; Forrester et al., (2003) Circulation 108: 1139-1145). Later on, the field realized that one important mode of therapeutic action is the secretion of paracrine factors by injected stem cells that act like "mini-drug pumps" to promote endogenous repair (Avolio et al., (2014) Stem Cells 32: 2373-2385; Li et al., (2012) J. Am. Coll. Cardiol. 59: 942-953). Moreover, stem cell membranes are not null in the repair process: contact with the injected stem cells triggers intracellular protective/regenerative pathways in the host cells (Xie et al., (2014) Stem Cells 32: 2397-2406; Ho et al. (2016) Stem Cells 34: 445-455).

SUMMARY

Briefly described, one aspect of the disclosure, therefore, encompasses embodiments of a stem cell biomimetic microparticle comprising at least one stem cell paracrine factor embedded in a biocompatible polymer core microparticle and an outer layer of at least one fragment of a cell membrane of a stem cell disposed on the polymer core microparticle.

In some embodiments of this aspect of the disclosure, the biocompatible polymer core of the microparticle can consist of a single species of polymer, a plurality of polymer species, a block copolymer, or a plurality of polymer species, and wherein the polymer or polymers of the polymer core can be cross-linked.

In some embodiments of this aspect of the disclosure, the biocompatible polymer core of the microparticle can be biodegradable.

In some embodiments of this aspect of the disclosure, the biocompatible polymer core comprises poly(lactic-co-glycolic acid) (PLGA).

In some embodiments of this aspect of the disclosure, the at least one stem cell paracrine factor and the cell membrane fragment or fragments can be from the same species of stem cell.

In some embodiments of this aspect of the disclosure, the at least one stem cell paracrine factor and the cell membrane fragment or fragments can be derived from cardiac stem cells.

In some embodiments of this aspect of the disclosure, the at least one stem cell paracrine factor and the cell membrane fragment or fragments can be from different species of stem cells.

In some embodiments of this aspect of the disclosure, the at least one stem cell paracrine factor can be from a stem cell-conditioned culture medium.

In some embodiments of this aspect of the disclosure, the at least one stem cell paracrine factor can be an isolated paracrine factor.

Another aspect of the disclosure encompasses embodiments of a stem cell biomimetic microparticle composition comprising a stem cell biomimetic microparticle of the disclosure and a pharmaceutically acceptable carrier.

In some embodiments of this aspect of the disclosure, the composition can be formulated for delivery directly into a target tissue of a subject animal or human or for local or systemic administration to a subject animal or human.

Another aspect of the disclosure encompasses embodiments of a method of generating a biomimetic microparticle, said method comprising the steps of: (a) admixing an aqueous solution comprising at least one stem cell paracrine factor with an organic phase having a polymerizable monomer dissolved therein; (b) emulsifying the admixture from step (a); and (c) admixing the emulsion from step (b) with an aqueous solution and allowing the organic phase to evaporate, thereby generating biocompatible polymer microparticles having the at least one stem cell paracrine factor embedded therein.

In some embodiments of this aspect of the disclosure, the method can further comprise the steps of: (i) obtaining an isolated stem cell membrane or fragments thereof; and (ii) generating stem cell membrane-coated biomimetic microparticles by mixing the biocompatible polymer microparticles from step (c) with the suspension of isolated stem cell membrane or fragments thereof.

In some embodiments of this aspect of the disclosure, the aqueous solution comprising the at least one stem cell paracrine factor can be a stem cell-conditioned culture medium or an aqueous solution of at least one isolated stem cell paracrine factor.

In some embodiments of this aspect of the disclosure, the aqueous solution comprising the at least one stem cell paracrine factor can be a cardiac stem cell-conditioned culture medium and wherein the cell membrane fragments are isolated from cardiac stem cells.

In some embodiments of this aspect of the disclosure, the polymerizable monomer polymer can be poly(lactic-co-glycolic acid) (PLGA).

In some embodiments of this aspect of the disclosure, the step (c) can further comprise lyophilizing the biocompatible polymer microparticles.

Yet another aspect of the disclosure encompasses embodiments of a method of tissue repair in a patient in need thereof by delivering to the patient a pharmaceutically acceptable composition comprising a stem cell biomimetic microparticle, wherein said stem cell biomimetic microparticle can comprise at least one stem cell paracrine factor embedded in a biocompatible polymer core microparticle and an outer layer of at least one fragment of a cell membrane of a stem cell disposed on the biocompatible polymer core microparticle.

In some embodiments of this aspect of the disclosure, the biocompatible polymer core of the microparticle can consist of a single species of polymer, a plurality of polymer species, a block copolymer, or a plurality of polymer species, and wherein the polymers of the polymer core can be optionally cross-linked.

In some embodiments of this aspect of the disclosure, the biocompatible polymer core of the microparticle can be biodegradable.

In some embodiments of this aspect of the disclosure, the biocompatible polymer core can comprise poly(lactic-co-glycolic acid) (PLGA).

In some embodiments of this aspect of the disclosure, the at least one stem cell paracrine factor and the cell membrane fragment or fragments can be from the same species of stem cell.

In some embodiments of this aspect of the disclosure, the at least one stem cell paracrine factor and the cell membrane fragment or fragments can be derived from cardiac stem cells.

In some embodiments of this aspect of the disclosure, the at least one stem cell paracrine factor and the cell membrane fragment or fragments can be from different species of stem cells.

In some embodiments of this aspect of the disclosure, the at least one stem cell paracrine factor can be from a stem cell-conditioned culture medium.

In some embodiments of this aspect of the disclosure, the at least one stem cell paracrine factor can be an isolated paracrine factor.

In some embodiments of this aspect of the disclosure, the pharmaceutically acceptable composition can be formulated for delivery directly into a target tissue of a subject animal or human or for local or systemic administration to a subject animal or human.

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 1A schematically illustrates the biochemical design and study model of an embodiment of the CMMPs of the disclosure. Microparticles (MPs, i.e. Control $MP_1$) were fabricated from Poly(lactic-co-glycolic acid) (PLGA) and conditioned media of human cardiac stem cells (CSCs); MPs were then cloaked with membrane fragments of CSCs to form Cell-mimicking Microparticles (CMMPs). Control $MP_2$ was fabricated by cloaking empty PLGA particles with CSC membranes. The therapeutic potential of CMMPs was tested in a mouse model of myocardial infarction.

FIGS. 1B and 1C illustrate Texas red succinimidyl ester-labeled MPs (FIG. 1B, left) were cloaked with the membrane fragments of green fluorescent DiO-labeled CSCs (FIG. 1B, right) to form the CMMP (FIG. 1C, particle with coat). Scale bar, 20 μm.

FIGS. 1D and 1E illustrate scanning electron microscopy (SEM) images revealing the CSC membrane fragments on CMMPs (FIG. 1E) but not on Control $MP_1$ (non-cloaked MP) (FIG. 1D). Scale bar, 10 μm.

FIGS. 1F and 1G illustrate a pair of graphs showing major human CSC markers CD105 (FIG. 1F) and CD90 (FIG. 1G) were positive on CMMPs and Control $MP_2$ but not on non-cloaked Control $MP_1$, indicating the membrane cloaking on CMMPs.

FIG. 1H is a bar graph showing that CMMPs, Control $MP_1$ and Control $MP_2$ have similar sizes to those of CSCs. n=3 for each group.

FIG. 1I illustrates a pair of bar graphs showing that CMMPs and Control $MP_2$ carried similar surface antigens as CSCs did. n=5 for each group.

FIGS. 1J-1L illustrate graphs showing similar release profiles of CSC factors (vascular endothelial growth factor (VEGF) (FIG. 1J), insulin-like growth factor (IGF)-1 (FIG. 1K), and hepatocyte growth factor (HGF) (FIG. 1L)) observed in CMMPs and Control $MP_1$, indicating membrane cloaking did not affect the release of CSC factors from CMMPs and Control $MP_1$. n=3 for each time point. All data are mean±s.d. Comparisons between any two groups were performed using two-tailed unpaired Student's t-test. Comparisons among more than two groups were performed using one-way ANOVA followed by post-hoc Bonferroni test.

FIG. 2A illustrates fluorescent images of CSCs (left panel) and CMMPs (right panel) labeled with CD105-PE conjugated antibody and the quantitative analysis of fluorescent intensities of CSCs and CMMPs.

FIG. 2B illustrates fluorescent images of CSCs (left panel) and CMMPs (right panel) labeled with CD90-FITC conjugated antibody and the quantitative analysis of fluorescent intensities of CSCs and CMMPs.

FIG. 3A illustrates representative images of cardiomyocytes stained with alpha sarcomeric actin co-cultured with Control $MP_1$, Control $MP_2$, CMMPs, or CSCs. Scale bar, 200 μm.

FIG. 3B illustrates a graph showing a quantitative analysis reflected that Control $MP_1$ increased the numbers of NRCMs as compared to those from Control $MP_2$ or solitary NRCM culture, but the greatest NRCM numbers were seen in those co-cultured with CMMPs and genuine CSCs. n=5 for each group.

FIG. 3C illustrates a graph showing a higher NRCM contractility seen in those cultured with CMMPs and CSCs compared to those cultured with Control $MP_1$ (red bar). n=5 for each group.

FIG. 3D illustrates representative images and quantitative analysis of NRCMs stained with alpha sarcomeric actin and proliferation marker Ki67, treated with Control MP$_1$, Control MP$_2$, CMMPs or CSC. n=5 for each group. Scale bar, 50 µm.

FIG. 3E illustrates representative images and quantitative analysis of CMMP or Control MP$_1$, Control MP$_2$ binding to NRCMs. n=3 for each group. Scale bar, 50 µm.

FIG. 3F illustrates representative movie screenshots and quantitation of Control MP$_1$' and CMMPs' synchronized movement with adjacent beating cardiomyocytes. n=3 for each group. Scale bar, 50 µm.

FIGS. 3G and 3H illustrate time-lapse images revealing the rolling (FIG. 3G) and traveling (FIG. 3H) of CMMPs on attached cardiomyocytes. Arrows indicated the rolling or moving directions. Scale bar, 20 µm. All data are mean±s.d. * indicates P<0.05 when compared to Control group; # indicates P<0.05 when compared to Control MP$_1$ group; & indicates P<0.05 when compared to Control MP$_2$. Comparisons between any two groups were performed using two-tailed unpaired Student's t-test. Comparisons among more than two groups were performed using one-way ANOVA followed by post-hoc Bonferroni test.

FIGS. 4A-4K illustrate cell-mimicking microparticles (CMMPs) ameliorate ventricular dysfunction and promote cardiac repair in a mouse model of heart attack.

FIG. 4A schematically illustrates the design of animal experiments to test the therapeutic benefits of CMMPs in a mouse model of myocardial infarction.

FIG. 4B illustrates representative ex vivo fluorescent imaging of mouse hearts and quantitative analysis of fluorescent intensities at Day 3 after Control MP$_1$ or CMMP injections. n=3 animals per group. * indicates P<0.05 when compared to Control MP$_1$ group.

FIG. 4C illustrates representative microscopic images and quantitative analysis of mouse hearts (myocytes stained with alpha sarcomeric actin 3 days after injection of Control MP$_1$ or CMMPs. n=3 animals per group. Scale bar, 50 µm. * indicates P<0.05 when compared to Control MP$_1$ group.

FIG. 4D illustrates representative fluorescent micrographs and quantitative analysis showing the presence of TUNEL$^+$ apoptotic cells in CMMP-treated hearts at Day 7. n=3 animals per group. Scale bar, 50 µm. * indicates P<0.05.

FIG. 4E illustrates Representative fluorescent micrographs showing the presence of CD45$^+$ cells (green) in the hearts treated with or without CMMPs (red) at Day 7. n=animals per group. Scale bar, 50 µm. NS indicates P>0.05.

FIG. 4F illustrates representative Masson's trichrome-stained myocardial sections 4 weeks after treatment with Control PBS, Control MP$_1$, CMMPs, or CSCs. Snapshots=high magnification images of the red box area.

FIGS. 4G-4I is a series of bar graphs illustrating quantitative analyses of viable myocardium (FIG. 4G), infarct thickness (FIG. 4H) and scar size (FIG. 4I) from the Masson's trichrome images. n=5 animals per group.

FIGS. 4J and 4K illustrate left ventricular ejection fraction (LVEF) measured by echocardiography at baseline (4 h post-MI) and 4 weeks afterward in Control PBS, Control MP$_1$, CMMP and CSC groups. n=7 animals per group. * indicates P<0.05 when compared to Control group; # indicates P<0.05 when compared to Control MP$_1$ group; NS indicates P>0.05. All data are mean±s.d. Comparisons between any two groups were performed using two-tailed unpaired Student's t-test. Comparisons among more than two groups were performed using one-way ANOVA followed by post-hoc Bonferroni test.

FIG. 5A illustrates representative images showing alpha sarcomeric actin (αSA)-positive cardiomyocyte nuclei in control PBS-, Control MP$_1$-, or CMMP-treated hearts at 4 weeks. The numbers of αSA-positive nuclei were quantified. n=3 animals per group. Scale Bar, 100 µm.

FIG. 5B illustrates representative images showing Ki67-positive cardiomyocyte nuclei in control PBS-, Control MP$_1$-, or CMMP-treated hearts at 4 weeks. The numbers of Ki67-positive nuclei were quantified, n=3 animals per group. Scale Bar, 20 µm.

FIG. 5C illustrates representative images showing lectin-labeled blood vessels in control PBS- and Control MP$_1$- or CMMP-treated hearts at 4 weeks. The lectin fluorescent intensities were quantified. n=3 animals per group. Scale Bar, 100 µm.

FIG. 5D illustrates representative images showing arterioles stained with alpha smooth muscle actin (αSMA) in control PBS-, Control MP$_1$-, or CMMP-treated hearts at 4 weeks. The numbers of αSMA positive vasculatures were quantified. n=3 animals per group. Scale Bar, 50 µm. * indicates P<0.05 when compared to CMMP group. All data are mean±s.d. Comparisons among more than two groups were performed using one-way ANOVA followed by post-hoc Bonferroni test.

FIG. 6A schematically illustrates the animal study design to assess the local T cell immune reaction induced by human cardiac stem cells (CSCs) or CMMPs derived from human CSCs.

FIGS. 6B and 6C illustrate representative fluorescent images showing the presence of infiltrated CD3$^+$ T cells in CSCs (FIG. 6B) or CMMPs (FIG. 6C)-injected hearts at Day 7. Scale bar, 10 µm.

FIGS. 6D and 6E illustrate representative fluorescent images showing the presence of infiltrated CD8$^+$ T cells in CSCs (FIG. 6D)- or CMMPs (FIG. 6E)-injected hearts at Day 7. Scale bar, 10 µm.

FIGS. 6F and 6G illustrate quantitative analysis of CD3$^+$ and CD8$^+$ T cells in CSCs or CMMPs injected hearts at Day 7, n=3 animals per group. All data are mean±s.d. Comparisons between any two groups were performed using two-tailed unpaired Student's t-test. * indicates P<0.05 when compared to CSC group, FIG. 7 schematically illustrates a method of obtaining a population of cardiac stem cells using the cardiosphere system.

FIG. 14A is a schematic illustration of the fabrication process of synMSC.

FIG. 14B illustrates scanning electron microscopy images (left) and fluorescent images (right) on the structure of MP and synMSC, Scale bar, 10 μm.

FIGS. 14C and 14D illustrate quantitative analyses on the diameter and expressions of MSC markers in the MP, synMSC, and MSC.

FIGS. 14E-14G illustrate quantitative analyses on the release of vascular endothelia growth factor (VEGF), stromal cell-derived factor-1 (SDF-1), and insulin-like growth factor-1 (IGF-1) from synMSC, n=3 for each group. All data are mean±SD.

FIGS. 15A-15I illustrate the potency and stability of synthetic mesenchymal stem cells (synMSC) in vitro.

FIG. 15A illustrate fluorescent images of neonatal rat cardiomyocytes (NRCM) stained with a sarcomeric actin and co-cultured with microparticles (MP), synMSC, and MSC. Scale bar, 100 μm.

FIGS. 15B and 15C illustrate quantitative analyses of NRCM numbers and contractility when co-cultured with MP, synMSC, and MSC. FIG. 15D illustrates quantitative analyses on the number of MP and synMSC binding to NRCM.

FIG. 15E illustrates fluorescent images (above) and white light microscopy images (below) on synMSC morphology and aggregation before and after freeze/thaw. Scale bar, above, 10 μm; below, 100 μm.

FIGS. 15F and 15G illustrate quantitative analyses on the size and surface antigen expressions of synMSC before and after freeze/thaw.

FIG. 15H illustrates representative fluorescent images and illustration showing macrophage attraction after the injection of freeze/thawed MSC and synMSC into a mouse heart. Scale bar, 100 μm.

FIG. 15I illustrates quantitative analyses of the CD68+ macrophages in freeze/thawed MSC- or synMSC-injected mouse heart. N=4 for each group. All data are mean±SD.

FIG. 16A illustrates representative positron emission tomography/computed tomography (PET/CT) images and single photon emission computed tomography (SPECT)/CT images obtained at baseline and end point of mice after myocardial infarction (MI) with or without synMSC treatment.

FIG. 16B illustrates quantitative analyses on the percentage of altered infarct area and left ventricular (LV) volume (end point vs baseline) in control and synMSC-treated mice.

FIG. 16C illustrates Masson trichrome staining images from the base, midpapillary, and apical regions of the infarcted heart 2 wks after MI of control, synMSC-, and MSC-treated mice.

FIGS. 16D and 16E illustrate quantitative analyses of infarct wall thickness (FIG. 16D) and infarct size (FIG. 16E) of LV in control, synMSC-, and MSC-treated mice. n=8 for each group. All data are mean±SD. *P<0.05 when compared with control.

FIGS. 17A-17CF illustrate representative fluorescent images showing c-kit-positive, CD34-positive, and ki67-positive cells in the infarcted heart after control, synMSC, or MSC treatment, Arrows indicate the positively stained cells. Scale bars: FIGS. 17A and 17C, 20 μm; FIG. 17B, 50 μm.

FIGS. 17D-17F illustrate quantitative analyses on c-kit-positive cells, CD34-positive cells, and ki67-positive cells in the infarcted heart after control, synMSC, or MSC treatment. n=6 for each group. All data are mean±SD. *P<0.05 when compared with control.

DETAILED DESCRIPTION

Figure 1A:
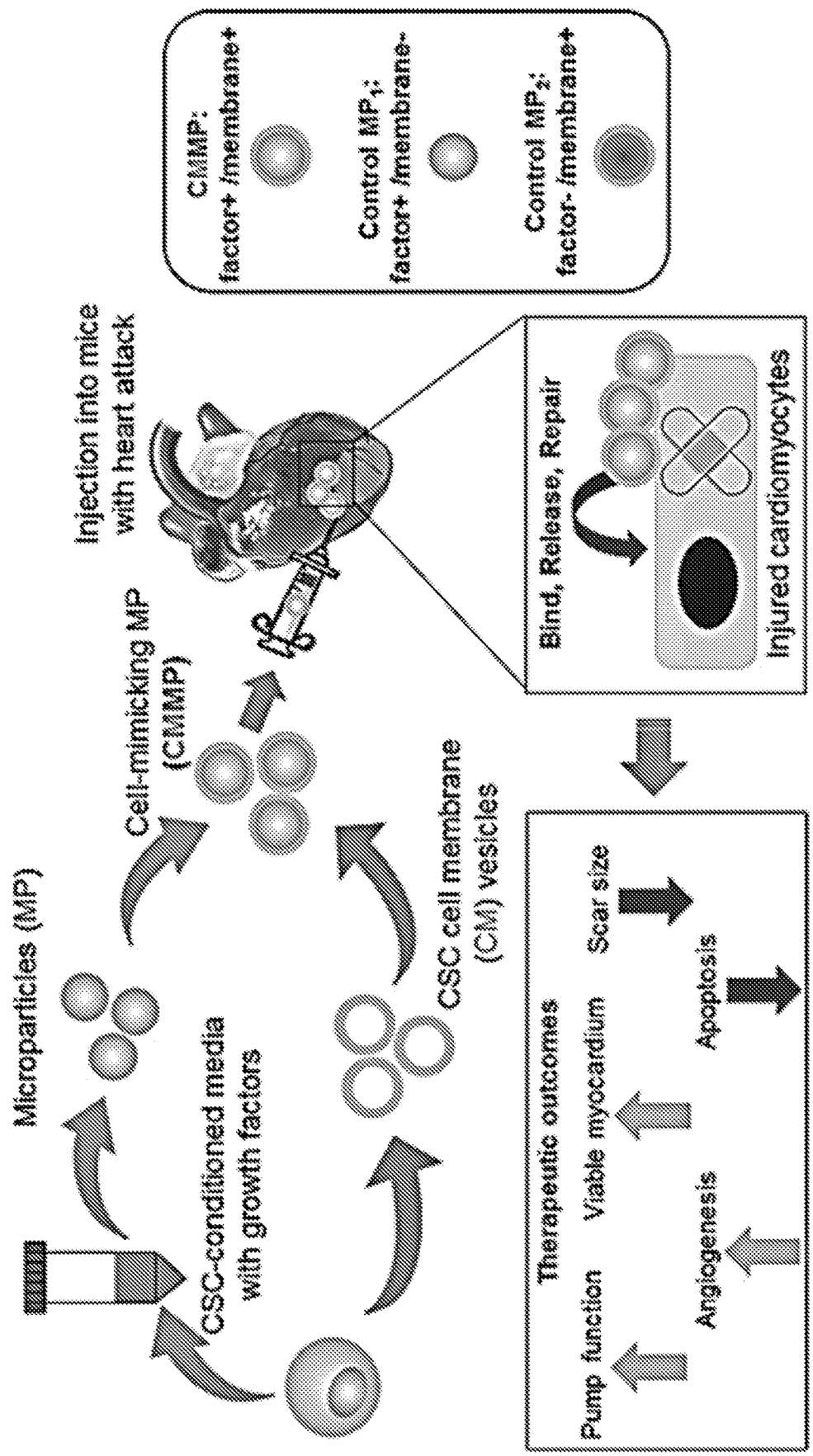
FIGS. 1A-1L illustrate the physiochemical and biological properties of cell-mimicking microparticles (CMMPs).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range, Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Prior to describing the various embodiments; the following definitions are provided and should be used unless otherwise indicated.

Abbreviations

CMMP, Cell-mimicking microparticle; CSCs, cardiac stem cells; PLGA, poly(lactic-co-glycolic acid; PVA, polyvinyl alcohol; microparticle, MP; Control $MP_1$, control microparticle fabricated from PLGA and conditioned media of human CSCs; Control $MP_2$, control microparticle fabricated from PLGA MPs and CSC membranes, SEM, scanning electron microscopy; VEGF, vascular endothelial growth factor; IGF-1, insulin-like growth factor; HGF, hepatocyte growth factor; FITC, fluorescein isothiocyanate; NRCM, neonatal rat cardiomyocyte; LVEF, left ventricular ejection fraction; PBS, phosphate-buffered saline; αSMA; alpha smooth muscle actin; GFP; green fluorescent protein; MI, myocardial infarction; synMSC, synthetic mesenchymal stem cell.

Definitions

The terms "administration of" and "administering" a compound or composition as used herein refers to providing a compound of the disclosure or a prodrug of a compound of the disclosure to the individual in need of treatment. The compounds of the present disclosure may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration.

The term "biocompatible" as used herein refers to a material that does not elicit any undesirable local or systemic effects in vivo.

The terms "biological material" and "biological tissue" as used herein refer to cells or tissue in vivo (e.g. cells or tissue of a subject) and in vitro (e.g. cultured cells).

The term "secretome" as used herein refers to polypeptides secreted into and collected from an extracellular culture medium.

The term "biodegradable" as used herein refers to a polymer or polymer backbone that undergoes with the passage of time substantial degradation under physiological conditions or in a biological environment. In other words, the polymer backbone has a molecular structure that is susceptible to break down (i.e. a reduction in molecular weight) by chemical decomposition in a biological environment (e.g. within a subject or in contact with biological material such as blood, tissue, etc.), as opposed to physical degradation. Such chemical decomposition will typically be via the hydrolysis of labile or biodegradable moieties that form part of the molecular structure of the backbone. Accordingly, such labile or biodegradable moieties will generally be susceptible to hydrolytic cleavage.

Biodegradable and biocompatible polymers have been designated as probable carriers for long term and short time delivery vehicles including non-hydrolysable polymeric conjugates. PEGs and PEOs are the most common hydroxyl end polymers with a wide range of molecular weights to choose for the purpose of solubility (easy carrier mode), degradation times and ease of conjugation. End-protected methoxy-PEGs will also be employed as a straight chain carrier capable of swelling and thereby reducing the chances of getting protein attached or stuck during the subcellular transportation. Certain copolymers of ethylene and vinyl acetate, i.e. EVAc which have exceptionally good biocompatibility, low crystallinity and hydrophobic in nature are candidates. Among the most common and recommended biodegradable polymers from lactic and glycolic acids can be used.

The term "biomimetic" as used herein refers to a material or structure designed to resemble and/or function in a manner similar to a cell found in a native state in an animal or human. In the embodiments of the disclosure, the biomimetic compositions herein disclosed are suitable as substitutes for the replacement of a population of stem cells such as, but not limited to cardiac stem cells.

The term "paracrine signaling" as used herein refers to a form of cell-cell communication in which a cell produces a signal to induce changes in nearby cells, altering the behavior or differentiation of those cells. Signaling molecules known as paracrine factors diffuse over a relatively short distance (local action), as opposed to endocrine factors (hormones which travel considerably longer distances via the circulatory system), juxtacrine interactions, and autocrine signaling. Cells that produce paracrine factors secrete them into the immediate extracellular environment. Factors then travel to nearby cells in which the gradient of factor received determines the outcome Although paracrine signaling elicits a diverse array of responses in the induced cells, most paracrine factors utilize a relatively narrow set of receptors and pathways. Different organs in the body, even between different species, can utilize similar sets of paracrine factors in differential development. Highly conserved receptors and pathways can be organized into four major families based on similar structures: Fibroblast growth factor (FGF) family, Hedgehog family, Wnt family, and TGF-β superfamily. Binding of a paracrine factor to its respective receptor initiates signal transduction cascades, eliciting different responses.

For paracrine factors to induce a response in the receiving cell, that cell must have the appropriate receptors available on the cell membrane to receive the signals, also known as being competent. Additionally, the responding cell must also have the ability to be mechanistically induced.

The term "cell growth factor" (also referred to as "paracrine factor") as used herein refers to a naturally occurring substance capable of stimulating cellular growth, proliferation and cellular differentiation. Usually it is a protein or a steroid hormone but may further include any molecule such as, but not limited to, a nucleic acid or small molecule secreted by the stem cells of the compositions of the disclosure and which may interact with and influence the growth or differentiation of cells in close proximity to the secreting cell. Growth factors are important for regulating a variety of cellular processes. Growth factors typically act as signaling molecules between cells. Examples are cytokines and hormones that bind to specific receptors on the surface of their target cells. They often promote cell differentiation and maturation, which varies between growth factors. For example, bone morphogenic proteins stimulate bone cell differentiation, while fibroblast growth factors and vascular endothelial growth factors stimulate blood vessel differentiation (angiogenesis). While growth factor implies a positive effect on cell division, cytokine is a neutral term with respect to whether a molecule affects proliferation. Some cytokines can be growth factors, such as G-CSF and GM-CSF. Individual growth factor proteins tend to occur as members of larger families of structurally and evolutionarily related proteins such as, but not limited to, Adrenomedullin (AM), Angiopoietin (Ang-2), Autocrine motility factor, Bone morphogenetic proteins (BMP-2, BMP-4, BMP-6), Brain-derived neurotrophic factor (BDNF), Epidermal growth factor (EGF), Erythropoietin (EPO), Fibroblast growth factor (FGF-2 (FGF-β), FGF-4), Glial cell line-derived neurotrophic factor (GDNF), Granulocyte colony-stimulating factor (G-CSF), Granulocyte macrophage colony-stimulating factor (GM-CSF), Growth differentiation factor-9 (GDF-5, GDF-7, GDF-8, GDF9, GDF-11), Hepatocyte growth factor (HGF), Hepatoma-derived growth factor (HDGF), Insulin-like growth factor (IGF-1, IGF-2), Migration-stimulating factor, Myostatin (GDF-8), Platelet-derived growth factor (PDGF), Thrombopoietin (TPO), Transforming growth factor-alpha (TGF-α), Transforming growth factor-beta (TGF-β), Tumor necrosis factor-alpha (TNF-α), and Vascular endothelial growth factor (VEGF).

The term "pharmaceutically acceptable carrier, excipient, or vehicle" as used herein refers to a medium which does not interfere with the effectiveness or activity of an active ingredient and which is not toxic to the hosts to which it is administered and which is approved by a regulatory agency of the Federal or a state government or listed in the U.S. Pharmacopeia or other generally recognized pharmacopeia for use in animals, and more particularly in humans. A carrier, excipient, or vehicle includes diluents, binders, adhesives, lubricants, disintegrates, bulking agents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The terms "pharmaceutically acceptable" or "pharmacologically acceptable" as used herein refer to a material that is not biologically or otherwise undesirable, i.e., the material may be administered to an individual in a formulation or composition without causing any undesirable biological effects or interacting in a deleterious manner with any of the components of the composition in which it is contained.

The terms "subject" and "patient" as used herein include humans, mammals cats, dogs, horses, etc.), living cells, and other living organisms. A living organism can be as simple as, for example, a single eukaryotic cell or as complex as a mammal. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. In some embodiments, a system includes a sample and a subject. The term "living host" refers to host or organisms noted above that are alive and are not dead. The term "living host" refers to the entire host or organism and not just a part excised (e.g., a liver or other organ) from the living host.

The term "biomolecule species" as used herein refers to any molecule that may be of biological origin and/or interact with a cell in contact therewith. A biomolecule species of use in the microparticles of the disclosure may be, but are not to be limited to, a protein, a polypeptide, a peptide, a nucleic acid molecule, a saccharide, a polysaccharide, a cytokine and the like that may be, but is not limited to, increasing or decreasing the proliferation of the cell or cell line, may sustain viability and/or proliferation of the cell or cell line, or may initiate a change in the cell type from a stem cell type, a precursor cell type or a progenitor cell type.

The term "proliferative status" as used herein refers to whether a population of cells including, but not limited to, mesenchymal stem or progenitor cells, or a subpopulation thereof, are dividing and thereby increasing in number, in the quiescent state, or whether the cells are not proliferating, dying or undergoing apoptosis.

The terms "modulating the proliferative status" or "modulating the proliferation" as used herein refers to the ability of a compound to alter the proliferation rate of a population of stem or progenitor cells. A compound may be toxic, wherein the proliferation of the cells is slowed or halted, or the proliferation may be enhanced such as, for example, by the addition to the cells of a cytokine or growth factor.

The term "polymer" as used herein refers to molecules comprising two or more monomer subunits that may be identical repeating subunits or different repeating subunits. A monomer generally comprises a simple structure, low-molecular weight molecule containing carbon. Polymers may optionally be substituted. Polymers that can be used in the present disclosure include without limitation vinyl, acryl, styrene, carbohydrate derived polymers, polyethylene glycol (PEG), polyoxyethylene, polymethylene glycol, poly-trimethylene glycols, polyvinylpyrrolidone, polyoxyethylene, polyoxypropylene block polymers, and copolymers, salts, and derivatives thereof. In aspects of the disclosure, the polymer is poly(2-acrylamido-2-methyl-1-propanesulfonic acid); poly(2-acrylamido-2-methyl-1-propanesulfonic acid-coacrylonitrile, poly(2-acrylamido-2-methyl-1-propanesulfonic acid-co-styrene), poly(vinylsulfonic acid); poly(sodium 4-styrenesulfonic acid); and sulfates and sulfonates derived therefrom; poly(acrylic acid), poly(methylacrylate), poly(methyl methacrylate), and polyvinyl alcohol).

The term "growth factors" as used herein refers to proteins, peptides or other molecules having a growth, proliferative, differentiation, or trophic effect on cells, Such factors may be used for inducing proliferation or differentiation and can include, for example, any trophic factor that allows cells to proliferate, including any molecule which binds to a receptor on the surface of the cell to exert a trophic, or growth-inducing effect on the cell. Such factors include paracrine factors secreted by stem cells and which may induce or sustain proliferation or differentiation by cells in close proximity to the biomimetic microparticles of the disclosure. Factors include, but are not limited to, Adrenomedullin (AM); Angiopoietin (Ang); Autocrine motility factor; Bone morphogenetic proteins (BMPs); Ciliary neurotrophic factor family; Ciliary neurotrophic factor (CNTF); Leukemia inhibitory factor (LIF); Interleukin-6 (IL-6); Colony-stimulating factors; Macrophage colony-stimulating factor (m-CSF); Granulocyte colony-stimulating factor (G-CSF); Granulocyte macrophage colony-stimulating factor (GM-CSF); Epidermal growth factor (EGF); Ephrin A1; Ephrin A2; Ephrin A3; Ephrin A4; Ephrin A5; Ephrin B1; Ephrin B2; Ephrin B3; Erythropoietin (EPO); Fibroblast growth factor (FGF); Foetal Bovine Somatotrophin (FBS); GDNF family of ligands: Glial cell line-derived neurotrophic factor (GDNF); Neurturin; Persephin; Artemin; Growth differentiation factor-9 (GDF9); Hepatocyte growth factor (HGF); Hepatoma-derived growth factor (HDGF); Insulin; Insulin-like growth factor-1 (IGF-1); Insulin-like growth factor-2 (IGF-2); Interleukins: IL-1; IL-2; IL-3; IL-4; IL-5; IL-6; IL-7; Keratinocyte growth factor (KGF); Migration-stimulating factor (MSF); Macrophage-stimulating protein (MSP); Myostatin (GDF-8); Neuregulins; Neuregulin 1 (NRG1); Neuregulin 2 (NRG2); Neuregulin 3 (NRG3); Neuregulin 4 (NRG4); Brain-derived neurotrophic factor (BDNF); Nerve growth factor (NGF); Neurotrophin-3 (NT-3); Neurotrophin-4 (NT-4); Placental growth factor (PGF); Platelet-derived growth factor (PDGF); Renalase (RNLS); T-cell growth factor (TCGF); Thrombopoietin (TPO); Transforming growth factors; Transforming growth factor alpha (TGF-α); Transforming growth factor beta (TGF-β); Tumor necrosis factor-alpha (TNF-α); Vascular endothelial growth factor (VEGF), and the like.

Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made.

Description

Stem cell therapy represents a promising strategy in regenerative medicine. However, cells need to be carefully preserved and processed before usage. In addition, cell transplantation carries immunogenicity and/or tumorigenicity risks. Mounting lines of evidence indicate that stem cells exert their beneficial effects mainly through secretion (of regenerative factors) and membrane-based cell-cell interaction with the injured cells.

Based on these two aspects, a "core-shell" therapeutic microparticle is provided that mimics stem cell biointerfacing during regeneration. This particle, a cell-mimicking microparticle (CMMP), contains control-released stem cell factors in its polymeric core and is cloaked with stem cell membrane fragments on the surface. While not wishing to be bound to any one theory, it is contemplated that CMMP can exert similar regenerative outcomes as real cardiac stem cells but are advantageous over the later since they are more stable during storage and do not stimulate T cell immune reaction since they are not real cells.

Accordingly, provided are embodiments of a polymer microparticle that emulates, for example, cardiac stem cell functions during tissue repair. In a mouse model of myocardial infarction, injection of CMMPs of the disclosure led to the preservation of viable myocardium and augmentation of cardiac functions similar to cardiac stem cell therapy. CMMPs (derived from human cells) did not stimulate T cells infiltration in immuno-competent mice, suggesting an advantageous safety profile. Although one application is targeted to the heart, the CMMPs of the disclosure represent a platform technology that can be applied to multiple stem cell types and the repair of a variety of organ systems.

The present disclosure, therefore, encompasses embodiments of a synthetic cell-mimicking microparticle (CMMP) that is useful for recapitulating (mimicking) stem cell functions in tissue repair. The CMMPs of the disclosure can accommodate and deliver secreted proteins and membranes similar to those of genuine cardiac stem cells. It has been shown, for example, that in a mouse model of myocardial infarction, injection of CMMPs will lead to the preservation of viable myocardium and augmentation of cardiac functions similar to cardiac stem cell therapy. CMMPs (derived from human cells) do not stimulate T cells infiltration in immuno-competent mice. However, the microparticles of the disclosure may be used to mimic a broad range of stem cells that may be usefully applied as therapeutic agents. Accordingly, CMMPs can function as "synthetic stem cells" that mimic the paracrine and biointerfacing activities of natural stem cells in therapeutic cardiac regeneration.

The last one and half decades have witnessed an expansion of available stem cell therapies for multiple diseases (Segers & Lee (2008) *Nature* 451: 937-942; Lindvall & Kokaia (2006) *Nature* 441: 1094-1096; Fox et al., (2014) *Science* 345: 1247391). Deviating from the initial perspective that stem cells exert their therapeutic effects through direct cell differentiation and tissue replacement, the paradigm has now shifted as emerging evidence suggests that most adult stem cell types exert their beneficial effects through paracrine mechanisms (soluble factors) (Hodgkinson et al., (2016) *Circ Res.* 118: 95-107; Walter et al., (2014) *Lancet Respir. Med.* 2: 1016-1026; Lanzoni et al., (2013) *Stem Cells* 31: 2047-2060). In addition, studies further suggest that cell-cell contact between the injected cells and the host cells plays an important role in tissue regeneration (Xie et al. (2014) *Stem Cells* 32: 2397-2406; Ho et al. (2016) *Stem Cells* 34: 445-455).

CMMP represents a synthetic microparticle functionalized with both stem cell-derived membrane and secretome, combining two major components of stem cell-induced regeneration. Advantageously, CMMP overcomes several limitations of live stem cells as therapeutic agents, First, living stem cells need to be carefully cryo-preserved and thawed before they can be sent to the clinic. As living organisms, how the cells are prepared and processed can greatly affect the therapeutic outcomes. Second, stem cell transplantation carries certain risks (e.g. tumorigenicity and immunogenicity if allogeneic or xenogeneic cells were used).

While it is contemplated that CMMPs of the disclosure can be delivered intramyocardially via direct muscle injection, such injection normally requires open-chest surgery. However, percutaneous options are becoming available with the implementation of the NOGA mapping systems (Gyöngyösi & Dib (2011) *Nat. Rev. Cardiol.* 8: 393-404), although the CMMPs may be directly delivered to a site of injury and thereby promote extravasation through the mechanism of angiopellosis. In addition, CMMP represents a platform technology that is generalizable to other stem cell types and the repair of various other organ systems.

The present disclosure, therefore, encompasses embodiments of stem cell biomimetic microparticles that comprise at least one stem cell-derived paracrine polypeptide or growth factor embedded in a polymer core particle which further comprises an outer layer of at least one fragment of a cell membrane of a stem cell disposed on the core particle. The polymer core itself is constituted of any biocompatible and biodegradable polymer or copolymer, or a combination of polymer or copolymer species that will allow the embedding of the paracrine factors and their prolonged release from the core. The core and hence the microparticles are preferably biodegradable which will lead to their being eventually eliminated from a recipient animal or human subject.

The core particles are sized to allow both transport through blood vessels and extravasation from the blood vessels into the surrounding tissues. The polymer of the core particle may be formed from a solution of the component monomers that further includes at least one polypeptide or peptide growth factor selected to induce the generation and proliferation of a population of stem cells. Most preferably, the growth factor(s) has been selected as also being secreted by a targeted stem cell population. Accordingly, one source of the polypeptides for incorporation in the biomimetic microparticles of the disclosure is a conditioned culture medium that has been used to culture and increase a population of isolated stem cells.

During the culturing of the cells they are known to generate and secrete paracrine growth factors that can, for example, interact with receptors on the surface of similar stem cells to promote the growth of the recipient cells. Thus, by admixing the cultured medium with the solution of the polymer precursors and then forming a polymer, the growth factors become embedded in the matrix of the polymer of the microparticles. Before admixing with the polymer precursor, the growth factor polypeptides of the conditioned medium can be concentrated to a degree that when embedded in the microparticles and delivered to a recipient animal or human subject they will be secreted from the microparticles to provide a concentration effective in stimulating the growth and proliferation of cells in the target tissue. The constituents of the conditioned medium may be concentrated by methods well known to those of skill in the art, for example, but not intended to be limiting, by such as lyophilization and resuspension in a reduced liquid volume and by ultrafiltration.

Other than conditioned cell culture medium, the microparticles of the disclosure may have embedded therein defined growth factor polypeptides that have been identified as capable of inducing and sustaining stem cell proliferation in vivo. Any combination or number of different such growth factors may be incorporated into the microparticles, the combination being adjusted for the type of stem cell and tissue repair of interest. Accordingly, the conditioned medium as a source of the growth factors may be replaced by a physiologically acceptable solution of isolated growth factors such as those that are readily commercially available Compositions of the present disclosure can include those that comprise a sustained release or controlled release matrix comprising at least one polymer material within which are embedded stem cell-derived paracrine factors. Embodiments of the present disclosure can be used in conjunction with other treatments that use sustained-release formulations, As used herein, a sustained-release microparticle polymer is preferably degradable by enzymatic or acid-based hydrolysis or by dissolution. Once inserted into the recipient tissue, the microparticles can be acted upon by enzymes and body fluids. Polymer matrix desirably is chosen from biocompatible materials such as polylactides (polylactic acid), polyglycolide (polymer of glycolic acid), polylactide co-glycolide (copolymers of lactic acid and glycolic acid), polyanhydrides, poly(ortho)esters, polyvinyl propylene, polyvinylpyrrolidone and silicone. Illustrative biodegradable matrices include a polylactide matrix, a polyglycolide matrix, and a polylactide co-glycolide (co-polymers of lactic acid and glycolic acid) matrix.

The biomimetic microparticles of the disclosure further comprise an outer layer disposed on the outer surface of the microparticles, the layer comprising fragments of the cell membrane of a stem cell. While it is preferable that the membrane fragments are isolated from the same type of stem cell that was used to provide the paracrine factors embedded in the microparticles, it is considered possible to provide a combination where the paracrine factors are sourced from one species of stem cell and the membranes from a second species of stem cell. Most advantageously, the stem cell membranes are isolated from cultured stem cells such as, but not limited to, cardiospheres, i.e. populations of stem cells cultured in vitro and which form spherical clusters of stem cell progeny.

Advantageously, the biomimetic microparticles of the disclosure, prior to the addition of the outer cell membrane layer may be prepared for prolonged storage using such techniques that maintain the stability of embedded growth factors and the integrity of the polymer matrix forming the body of the microparticles. Such technique are well-known to those in the art and include, but are not limited to, lyophilization (freeze-drying), freezing, or in buffered solution, and the like. The preserved microparticles may then, before administering to a recipient animal or human patient, be resuspended in a physiologically acceptable medium and then coated with the fragments of the isolated cell membranes.

A particle termed synMSC was fabricated by coating MSC cell membranes onto PLGA particles loaded with MSC secretome. This novel particle exhibited similar secretome and surface antigen profiles when compared with real MSCs. synMSC promoted cardiomyocyte function and displayed cryopreservation and lyophilization stability in vitro. Intramyocardial injection of synMSC mitigated left ventricle remodeling in a mouse model of acute MI at a level comparable to genuine MSC.

Emerging lines of evidences indicate that adult stem cells exert their therapeutic effects mainly through paracrine effects rather than direct differentiation. To that end, scientists have begun to consider the direct delivery of stem cell-released soluble factors as an alternative approach to stem cell transplantation. However, the progress is hindered by the short-lived effect of injected soluble factors. The cardiac contraction can quickly wash away the injected factors. Approaches that allow controlled release of soluble factors are paramount and urgently needed for the clinical implementation of stem cell-derived factors for therapeutic heart regeneration. Although exosomes show great potential in cardiac repair and may overcome the shortcomings associated with cell transplantation, the lack of standardized protocol for exosome isolation and the quick washout of exosomes after injection remains challenges for clinical application. synMSCs were designed that combined the secretome (containing both soluble factors and exosomes) and membranes of MSC. synMSC can release soluble factors such as vascular endothelial growth factor, stromal cell-derived factor-1, and insulin-like growth factor 1, binding to cardiomyocytes in vitro. In addition, the expression of MHC class I molecules, but not of MHC class II molecules or co-stimulatory molecules, in MSC cell membranes allows it to escape allorecognition by the immune system and may modulate the host immune response. The MSC membrane coating on PLGA particles could effectively protect synMSC from being attacked by host immune and inflammatory cells.

A great number of cardiomyocytes die after the induction of MI, The restoration of cardiomyocyte numbers is one important target for cell-based therapy. By co-culturing the synMSC with NRCM, a significant increase in NRCM number and contractility was observed at a level comparable to MSC, which may be associated with the growth factors released by synMSC.

The MSC membrane on synMSC can allow them to closely attach to cardiomyocytes by cell-cell interactions. Second, it has been reported that the stem cell membranes are not null in the regeneration process: direct contact may trigger downstream signaling in cardiomyocytes to favor survival and function augmentation.

One major challenges of stem cell-based therapy is the cryopreservation stability of cells. It is now found that snap freezing in −80° C. and rapid thawing did not alter the structure, size, or surface antigen expressions of synMSC. Furthermore, lyophilization did not alter the traits of synMSC. Importantly, when the freeze/thawed MSC (with dead MSC caused by harsh freezing/thawing) were injected into a mouse heart, they were targeted by macrophages (initiating the phagocytosis of dead MSC) whereas synMSCs were not suggesting advantageous cryopreservation stability of synMSCs over MSCs.

Currently, as CT can provide great detail in anatomic structure, hybrid imaging of positron emission tomography and single photon emission CT with CT has been adopted in clinical and small animal cardiovascular disease diagnosis. Positron emission tomography utilizing glucose tracer analog $^{18}$F-FDG allows the detection of cells with different metabolic activities, and gated single photon emission CT utilizing $^{99m}$Tc-tetrofosmin makes accurate assessment of ventricular volumes. Accordingly, it was evaluated whether the myocardial viability and left ventricle volume of mice heart by $^{16}$F-fluorodeoxglucose positron emission tomography/CT and $^{99m}$Tc-tetrofosmin single photon emission CT/CT.

synMSCs significantly mitigated left ventricle remodeling, as indicated by a significant reduction of infarct area, confirming the therapeutic potential of synMSC. Furthermore, the left ventricle morphometry evaluation by Masson trichrome staining revealed synMSC exhibited protection of heart morphometry at a level that was comparable to MSC.

It has been reported that MSC provides cardioprotection by paracrine actions that activate cardiac stem cells, angiogenesis, and cell proliferation. Consistent with these findings, a significant increase of c-kit-positive stem cells was found in synMSC-treated mice (similar to MSC treatment) although it is difficult to distinguish the origination of these c-kit-positive stem cells (cardiac derived or bone marrow derived). In addition, a larger number of vessels were found in synMSC-treated mice that would provide sufficient oxygen and nutrients to the surrounded cardiomyocytes.

Taken together, the successful fabrication of the synMSCs of the disclosure and their demonstrated therapeutic effects in an acute MI mouse model, suggest the advantageous use of this approach in regenerative medicine. Moreover, this synthetic stem cell approach can provide tissue engineering for treating multiple diseases. The results suggest that synthetic stem cells offer an alternative option to stem cell-mediated regenerative therapies.

One aspect of the disclosure, therefore, encompasses embodiments of a stem cell biomimetic microparticle comprising at least one stem cell paracrine factor embedded in a biocompatible polymer core microparticle and an outer layer of at least one fragment of a cell membrane of a stem cell disposed on the polymer core microparticle.

In some embodiments of this aspect of the disclosure, the biocompatible polymer core of the microparticle can consist of a single species of polymer, a plurality of polymer species, a block copolymer, or a plurality of polymer species, and wherein the polymer or polymers of the polymer core can be cross-linked.

In some embodiments of this aspect of the disclosure, the biocompatible polymer core of the microparticle can be biodegradable.

In some embodiments of this aspect of the disclosure, the biocompatible polymer core comprises poly(lactic-co-glycolic acid) (PLGA).

In some embodiments of this aspect of the disclosure, the at least one stem cell paracrine factor and the cell membrane fragment or fragments can be from the same species of stem cell.

In some embodiments of this aspect of the disclosure, the at least one stem cell paracrine factor and the cell membrane fragment or fragments can be derived from cardiac stem cells.

In some embodiments of this aspect of the disclosure, the at least one stem cell paracrine factor and the cell membrane fragment or fragments can be from different species of stem cells.

In some embodiments of this aspect of the disclosure, the at least one stem cell paracrine factor can be from a stem cell-conditioned culture medium.

In some embodiments of this aspect of the disclosure, the at least one stem cell paracrine factor can be an isolated paracrine factor.

Another aspect of the disclosure encompasses embodiments of a stem cell biomimetic microparticle composition comprising a stem cell biomimetic microparticle of the disclosure and a pharmaceutically acceptable carrier.

In some embodiments of this aspect of the disclosure, the composition can be formulated for delivery directly into a target tissue of a subject animal or human or for local or systemic administration to a subject animal or human.

Another aspect of the disclosure encompasses embodiments of a method of generating a biomimetic microparticle, said method comprising the steps of: (a) admixing an aqueous solution comprising at least one stem cell paracrine factor with an organic phase having a polymerizable monomer dissolved therein; (b) emulsifying the admixture from step (a); and (c) admixing the emulsion from step (b) with an aqueous solution and allowing the organic phase to evaporate, thereby generating biocompatible polymer microparticles having the at least one stem cell paracrine factor embedded therein.

In some embodiments of this aspect of the disclosure, the method can further comprise the steps of: (i) obtaining an isolated stem cell membrane or fragments thereof; and (ii) generating stem cell membrane-coated biomimetic microparticles by mixing the biocompatible polymer microparticles from step (c) with the suspension of isolated stem cell membrane or fragments thereof.

In some embodiments of this aspect of the disclosure, the aqueous solution comprising the at least one stem cell paracrine factor can be a stem cell-conditioned culture medium or an aqueous solution of at least one isolated stem cell paracrine factor.

In some embodiments of this aspect of the disclosure, the aqueous solution comprising the at least one stem cell paracrine factor can be a cardiac stem cell-conditioned culture medium and wherein the cell membrane fragments are isolated from cardiac stem cells.

In some embodiments of this aspect of the disclosure, the polymerizable monomer polymer can be poly(lactic-co-glycolic acid) (PLGA).

In some embodiments of this aspect of the disclosure, the step (c) can further comprise lyophilizing the biocompatible polymer microparticles.

Yet another aspect of the disclosure encompasses embodiments of a method of tissue repair in a patient in need thereof by delivering to the patient a pharmaceutically acceptable composition comprising a stem cell biomimetic microparticle, wherein said stem cell biomimetic microparticle can comprise at least one stem cell paracrine factor embedded in a biocompatible polymer core microparticle and an outer layer of at least one fragment of a cell membrane of a stem cell disposed on the biocompatible polymer core microparticle.

In some embodiments of this aspect of the disclosure, the biocompatible polymer core of the microparticle can consist of a single species of polymer, a plurality of polymer species, a block copolymer, or a plurality of polymer species, and wherein the polymers of the polymer core can be optionally cross-linked.

In some embodiments of this aspect of the disclosure, the biocompatible polymer core of the microparticle can be biodegradable.

In some embodiments of this aspect of the disclosure, the biocompatible polymer core can comprise poly(lactic-co-glycolic acid) (PLGA).

In some embodiments of this aspect of the disclosure, the at least one stem cell paracrine factor and the cell membrane fragment or fragments can be from the same species of stem cell.

In some embodiments of this aspect of the disclosure, the at least one stem cell paracrine factor and the cell membrane fragment or fragments can be derived from cardiac stem cells.

In some embodiments of this aspect of the disclosure, the at least one stem cell paracrine factor and the cell membrane fragment or fragments can be from different species of stem cells.

In some embodiments of this aspect of the disclosure, the at least one stem cell paracrine factor can be from a stem cell-conditioned culture medium.

In some embodiments of this aspect of the disclosure, the at least one stem cell paracrine factor can be an isolated paracrine factor.

In some embodiments of this aspect of the disclosure, the pharmaceutically acceptable composition can be formulated for delivery directly into a target tissue of a subject animal or human or for local or systemic administration to a subject animal or human.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Derivation and Culture of Human CSCs:

Human CSCs were derived from donor human hearts as previously described (Cheng et al., (2014) *J. Am. Heart Assoc.* 3: e001260; Cheng et al. (2012) *Biomaterials* 33; 5317-5324). Briefly, myocardial tissues were minced into small pieces about 2 mm$^3$, then washed with PBS and digested with collagenase solution (Sigma, St. Louis, Mo., USA). The tissue fragments were cultured as "cardiac explants" on plates coated with 0.5 mg/ml fibronectin (Corning, Corning, N.Y., USA) in Iscove's Modified Dulbecco's Medium (IMAM; Invitrogen, Carlsbad, Calif., USA) supplemented with 20% fetal bovine serum (FBS; Corning), 0.5% Gentamicin (Gibco, Life Technologies, California, USA), 0.1 mM 2-mercaptoethanol (Invitrogen, Carlsbad, Calif., USA) and 1% L-glutamine (Invitrogen, Carlsbad, Calif., USA), Within 1-2 weeks, a layer of stromal-like flat cells, and phase-bright round cells, emerged from the cardiac explant with phase bright cells over them. These cardiac explant-derived cells were harvested using TryPEL Select (Gibco), and then seeded at a density of $2\times10^4$ cells/ml in UltraLow Attachment flasks (Corning) for cardiosphere formation. In about 1 week, explant-derived cells spontaneously aggregated into cardiospheres. Cardiosphere-derived cardiac stem cells (CSCs) were generated by seeding collected cardiospheres on fibronectin-coated plates. All cultures were incubated in 5% $CO_2$ at 37° C.

Example 2

Fabrication of Control MPs and CMMPs:

CSC factor-loaded poly(lactic-co-glycolic acid) (PLGA) microspheres (Control $MP_1$) were fabricated by a water/oil/water (w/o/w) emulsion technique, Briefly, human CSC conditioned media as the internal aqueous phase with polyvinyl alcohol (PVA) (0.1% w/v) was mixed in methylene chloride (DCM) containing PLGA as the oil phase. The mixture was then sonicated on ice for 30 s using a sonicator with a Microtip probe (Misonix, XL2020, Farmingdale, N.Y., USA). After that, the primary emulsion was immediately introduced into water with PVA (0.7% w/v) to produce a w/o/w emulsion. The secondary emulsion was emulsified for 5 min on a high-speed homogenizer. The w/o/w emulsion was continuously stirred overnight at room temperature to promote solvent evaporation. The solidified microparticles, namely Control $MP_1$, were then centrifuged, washed three times with water, lyophilized and stored at −80° C. To prepare CMMPs, DiO (Invitrogen)-labeled CSCs went through three freeze/thaw cycles. After which, the disrupted CSCs were sonicated for approximately 5 minutes at room temperature along with the Control $MP_1$. After that, the particles were washed three times in PBS by centrifugation. Control $MP_2$ was fabricated by cloaking empty PLGA particles with CSC membranes. Successful membrane coating was confirmed using fluorescent microscopy.

Example 3

Protein Release Studies:

Total protein contents in microparticles were determined using the following method. Approximately 10 mg freeze-dried microspheres were dissolved in 1 ml DCM for 60 min. Then, 1 ml PBS was added into solution followed by agitation for 10 min to extract protein from DCM into PBS. After centrifugation, the concentration of protein in the aqueous phase was determined by a BCA Protein Assay Kit (Thermo Fisher Scientific, Waltham, Mass., USA). For release studies, microparticles were incubated in PBS at 37° C. Supernatant was collected at various time points and the concentrations of proteins were determined by commercially available ELISA kits (R & D Systems, Minneapolis, Minn., USA).

Example 4

Scanning Electron Microscopy:

The morphology of microspheres was studied by scanning electron microscopy (SEM, Philips XL30 scanning microscope, Philips, The Netherlands). Freeze-dried microspheres were mounted on aluminum stubs with double-sided tape and coated with a thin layer of gold. The coated specimen was then scanned and photographed under the microscope at an acceleration voltage of 15 kV.

Example 5

Flow Cytometry:

To characterize the phenotypes of Control $MP_1$, Control $MP_2$, CMMP and CSC, flow cytometry was performed using a CytoFLEX Flow Cytometer (Beckman Coulter, Brea, Calif.) and analyzed using FCS Express software (De Novo Software, Los Angeles, Calif.). Briefly, cells were incubated with FITC, PE, or APC-conjugated antibodies against CD105 (3 µl per 100 µl of sample, FAB 10971P, R&D Systems), CD90 (4 µl per 100 µl of sample, BD 555595), CD45 (5 µl per 100 µl of sample, BD 555982), CD34 (5 µl per 100 µl of sample, BD 555821), and CD117 (5 µl per 100 µl of sample, c-kit) (BD 550412) from BD company (Franklin Lakes, N.J.) for 60 min. Isotype-identical antibodies from BD Company served as negative controls (3 µl per 100 µl of sample).

Example 6

Immunocytochemistry:

Control $MP_1$, Control $MP_2$, CMMP, and CSC were pre-labeled with red-fluorescent Texas red succinimidyl ester (1 mg/ml [Invitrogen, Carlsbad, Calif.]). NRCM or NRCM co-cultured with pre-labeled Control $MP_1$, Control $MP_2$, CMMP, and CSC were plated onto fibronectin-coated chamber slides (BD Biosciences) and subsequently fixed with 4% paraformaldehyde (PFA) before immunocytochemistry (ICC) staining. Slides were stained with the antibodies against α-SA (1:100, a7811, Sigma) or ki67 (1:100, ab15580, Abcam) and detected by FITC- or Texas Red-conjugated secondary antibodies (1:100). Nuclei were stained with DAPI. Images were taken with an epi-fluorescent microscope (Olympus IX81).

Example 7

Mouse Model of Myocardial Infarction:

The method to induce myocardial infarction in mice was based on previous studies (Andrade et al., (2015) *PLoS One* 10: e0143221). Briefly, male CD1 mice were anesthetized with 3% isofluorane combined with 2% oxygen inhalation. Under sterile conditions, the heart was exposed by a minimally invasive left thoracotomy and acute myocardial infarction (AMI) was produced by permanent ligation of the left anterior descending coronary artery. Immediately after AMI induction, the heart was randomized to receive one of the following four treatment arms: 1) "Control (PBS)" group: Intramyocardial injection of 50 µl PBS into the heart immediately after AMI; 2) "Control $MP_1$" group: Intramyocardial injection of $1 \times 10^5$ Control $MP_1$ in 50 µl PBS into the heart immediately after AMI; 3) "CMMP" group: Intramyocardial injection of $1 \times 10^5$ CMMPs in 50 µl PBS into the heart immediately after AMI; 4) "CSC" group: Intramyocardial injection of $1 \times 10^5$ CSCs in 50 µl PBS into the heart immediately after AMI. To enable visualization of Control $MP_1$ or CMMP in a cohort of animals, the Control $MP_1$ or CMMP were pre-labeled with Texas Red-X succinimidyl ester (1 mg/ml [Invitrogen, Carlsbad, Calif.]).

Example 8

Ex Vivo Fluorescent Imaging for Biodistribution of CMMPs:

7 days after injection, a cohort of mice receiving CMMPs were sacrificed for harvesting the heart, lung, spleen, liver and kidney for biodistribution studies. Ex vivo fluorescent imaging was performed with an IVIS Xenogen In Vivo Imager (Caliper Lifesciences, Waltham, Mass.).

Example 9

Heart Morphometry:

After the echocardiography study at 4 weeks, all animals were euthanized and hearts were harvested and frozen in OCT compound. Specimens were sectioned at 10 µm thickness from the apex to the ligation level with 100 µm intervals. Masson's trichrome staining was performed as described by the manufacturer's instructions (HT15 Trichrome Staining (Masson) Kit; Sigma-Aldrich). Images were acquired with a PathScan Enabler IV slide scanner (Advanced Imaging Concepts, Princeton, N.J.). From the Masson's trichrome stained images, morphometric parameters including viable myocardium, infarct thickness and scar size were measured in each section with NIH ImageJ software. The percentage of viable myocardium as a fraction of the scar area (infarcted size) was quantified as described (Cheng et al., (2010) *Circ. Res.* 106: 1570-1581). Three selected sections were quantified for each animal.

Example 10

Cardiac Function Assessment:

All animals underwent transthoracic echocardiography under 1.5% isofluorane-oxygen mixture anesthesia in supine position at 4 h and 4 weeks. The procedure was performed by an animal cardiologist blind to the experimental design using a Philips CX30 ultrasound system couple with an L15 high-frequency probe. Hearts were imaged in 2D in long-axis views at the level of the greatest LV diameter. EF was determined by using the formula (LVEDV−LVESV/LVEDV)×100%.

Example 11

Histology:

For immunohistochemistry staining, heart cryosections were fixed with 4% paraformaldehyde, permeabilized and blocked with Protein Block Solution (DAKO, Carpinteria, Calif.) containing 0.1% saponin (Sigma, St. Louis, Mo.), and then incubated with the following antibodies overnight at 4° C.: mouse anti-alpha sarcomeric actin (1:100, a7811, Sigma), rabbit anti-CD45 (1:100, ab10559, Abcam, Cambridge, United Kingdom), mouse anti-Actin, α-Smooth Muscle antibody (1:100, A5228, Sigma), rabbit anti-Ki67 (1:100, ab15580, Abcam), rabbit anti-CD3 (1:100, ab16669, Abcam) and mouse anti-CD8 alpha (1:100, mca48r, abd Serotec, Raleigh, N.C.). FITC- or Texas-Red secondary antibodies (1:100) were obtained from Abcam Company and used for the conjunction with these primary antibodies. For assessment of cell apoptosis, heart cryosections were incubated with TUNEL solution (Roche Diagnostics GmbH, Mannheim, Germany) and counter-stained with DAPI (Life Technology, NY, USA). For assessment of angiogram, heart cryosections were incubated with Lectin (FL-1171, Vector laboratories, Burlingame, Calif., USA). Images were taken by an Olympus epi-fluorescence microscopy system.

Example 12

Immunogenicity Studies for Human CSCs and CMMPs:

Immune-competent male CD1 mice were anesthetized with 3% isofluorane combined with 2% oxygen inhalation. Under sterile conditions, the heart was exposed by a minimally invasive left thoracotomy, and the heart was randomized to receive one of the two treatments: 1) "CMMP" group: Intramyocardial injection of $1\times10^5$ CMMPs in 50 µl PBS into the heart; 2) "CSC" group: Intramyocardial injection of $1\times10^5$ human CSCs in 50 µl PBS into the heart. To enable visualization of CMMPs or CSCs, they were pre-labeled with red fluorophore.

Example 13

Statistical Analysis:

All results are expressed as mean±standard deviation (s.d.). Comparison between two groups was performed with two-tailed Student's t test. Comparisons between any two groups were performed using two-tailed unpaired Student's t-test. Comparisons among more than two groups were performed using one-way ANOVA followed by post-hoc Bonferroni test. Differences were considered statistically significant when the P value<0.05.

Example 14

Figure 7:
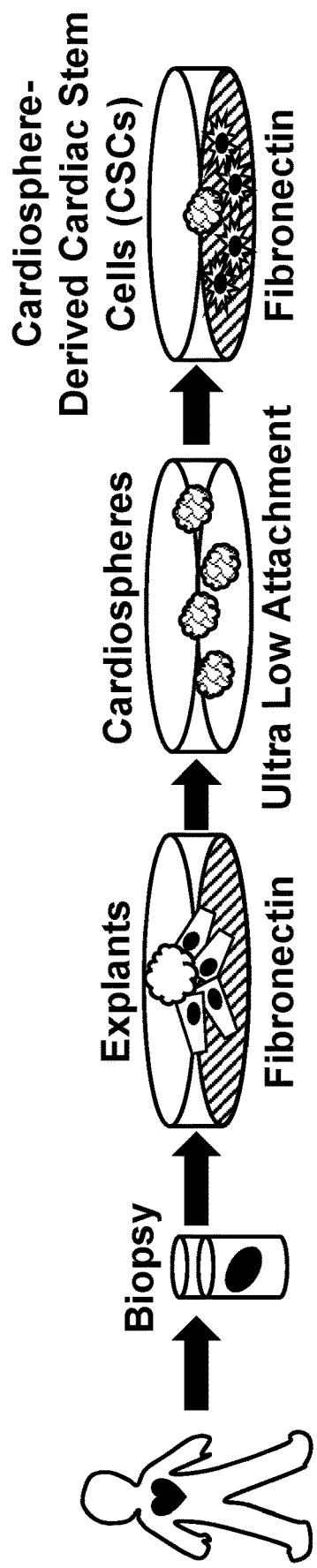
Figure 7:
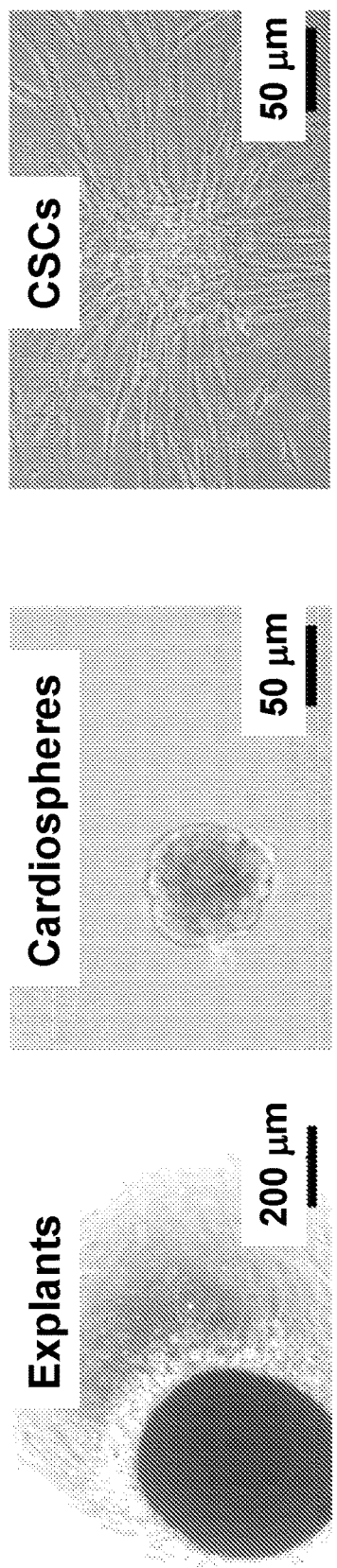

Physiochemical and Biological Properties of CMMPs:

The biochemical design and model of CMMPs of the disclosure are outlined in FIG. 1A, Therapeutic microparticles (MPs), i.e. Control $MP_1$, were fabricated from Poly (lactic-co-glycolic acid) (PLGA) and conditioned media of human cardiac stem cells (CSCs) that were isolated from human hearts using the cardiosphere method as previously described (Cheng et al., (2012) *Biomaterials* 33: 5317-5324; Cheng et al., (2014) *JACC Heart Fail.* 2: 49-61) and shown schematically in FIG. 7.

Figure 1B:
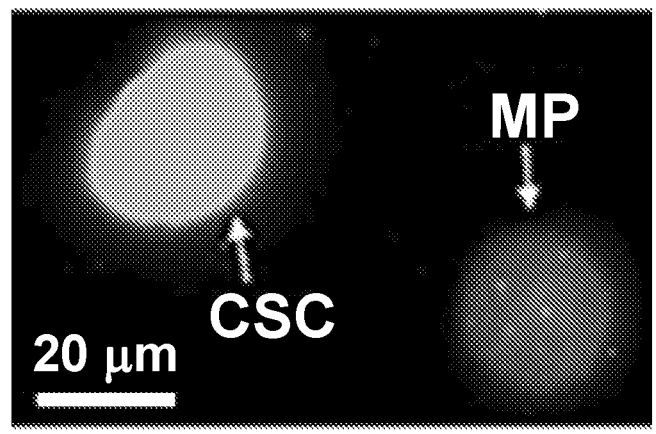
Figure 1C:
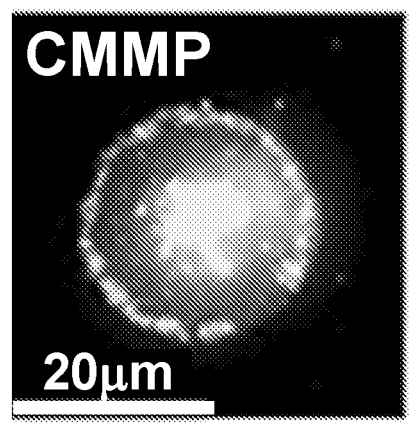

The conditioned media contained growth factors secreted by CSCs (Li et al., (2012) *J. Am. Coll. Cardiol.* 59: 942-953). CSCs have been tested and proven safe and effective in Phase I/II clinical trials (Makkar et al., (2012) *Lancet* 379: 895-904; Bolli et al., (2011) *Lancet* 378: 1847-1857; Malliaras et al., (2014) *J. Am. Coll. Cardiol.* 63: 110-122). After that, MPs (Texas red succinimidyl ester-labeled) (FIG. 1B) were cloaked with the membrane fragments of cardiac stem cells (green fluorescent DiO-labeled) (FIG. 1B) to become the final product CMMP (FIG. 1C).

Figure 1D:
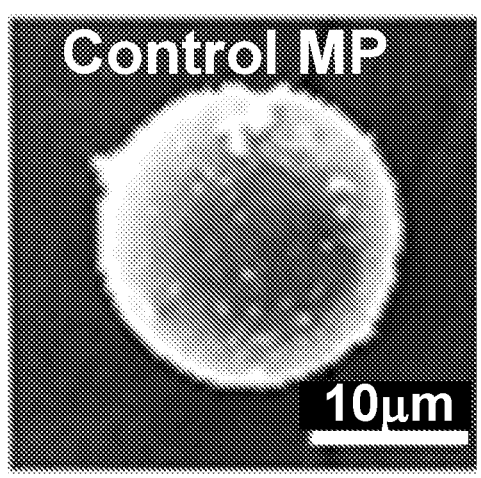
Figure 1E:
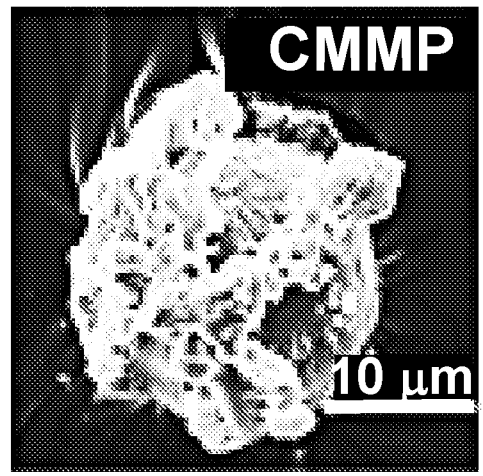
Figure 8:
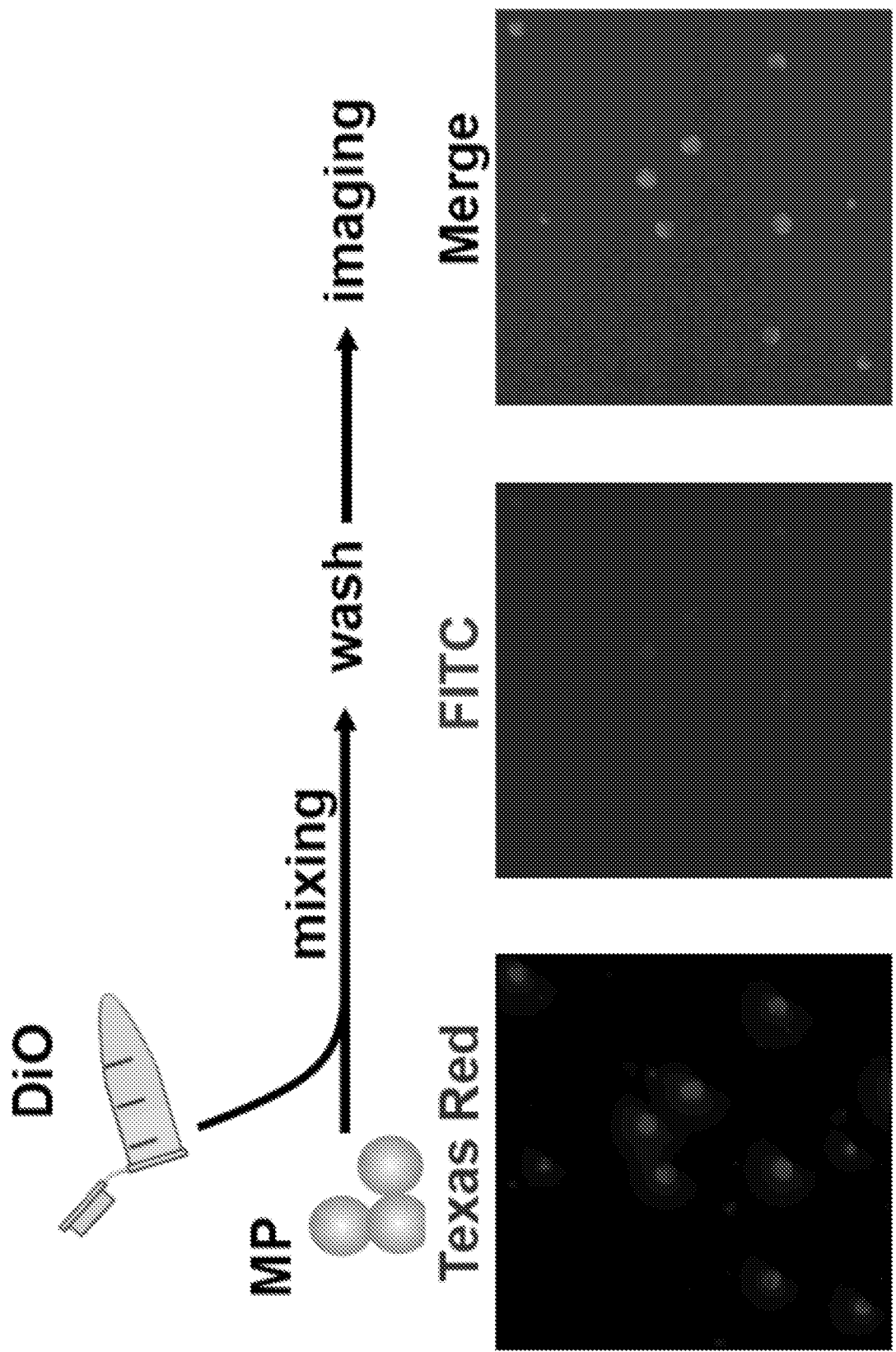
FIG. 8 illustrates fluorescent imaging that revealed there is no specific DiO outer layer fluorescence on Texas red succinimidyl ester-labeled MPs (Control MP$_1$) after 30 mins co-culture with cell membranes.
Figure 9A:
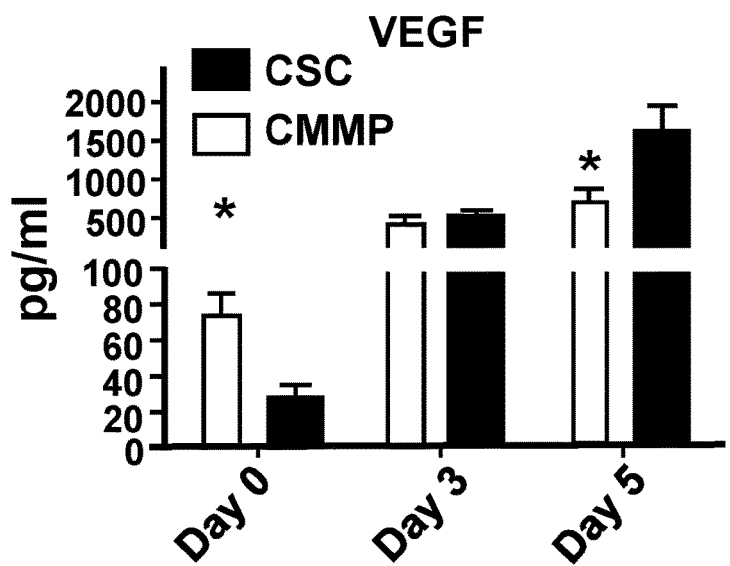
FIGS. 9A-9C illustrate release profiles of CSC factors (vascular endothelial growth factor (VEGF) (FIG. 9A), insulin-like growth factor (IGF)-1 (FIG. 9B), and hepatocyte growth factor (HGF) (FIG. 9C)) observed in CMMPs and CSCs, indicating membrane cloaking did not affect the release of CSC factors from CMMPs and CSCs. n=3 for each time point. All data are mean±s.d.
Figure 9B:
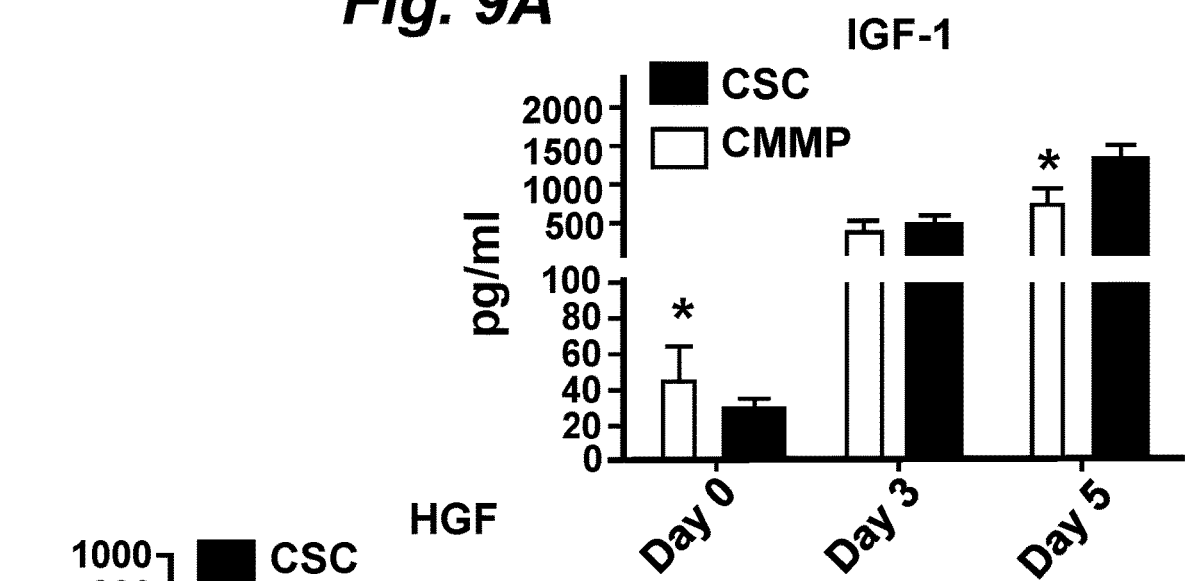
Figure 9C:
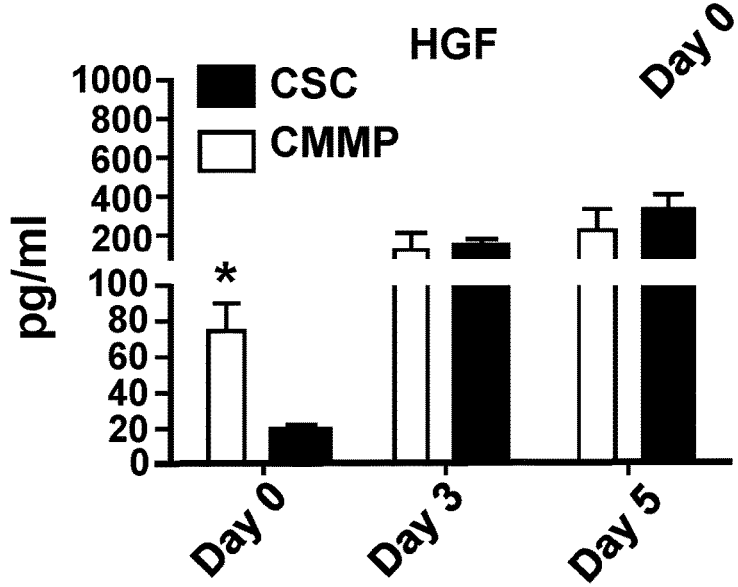

Fluorescent imaging revealed there was no specific DiO outer layer fluorescence on Texas red succinimidyl ester-labeled MPs (Control $MP_1$) after 30 mins co-culture, as shown in FIG. 8. Scanning electron microscopy (SEM) revealed the effective CSC membrane cloaking on CMMPs (FIG. 1E) but not on non-cloaked MPs (Control $MP_1$) (FIG. 1D), As another control particle; Control $MP_2$ was fabricated by cloaking empty PLGA particles with CSC membranes. CMMPs, Control $MP_1$, and Control $MP_2$ were fabricated with sizes similar to those of real CSCs (FIG. 1H).

Figure 1F:
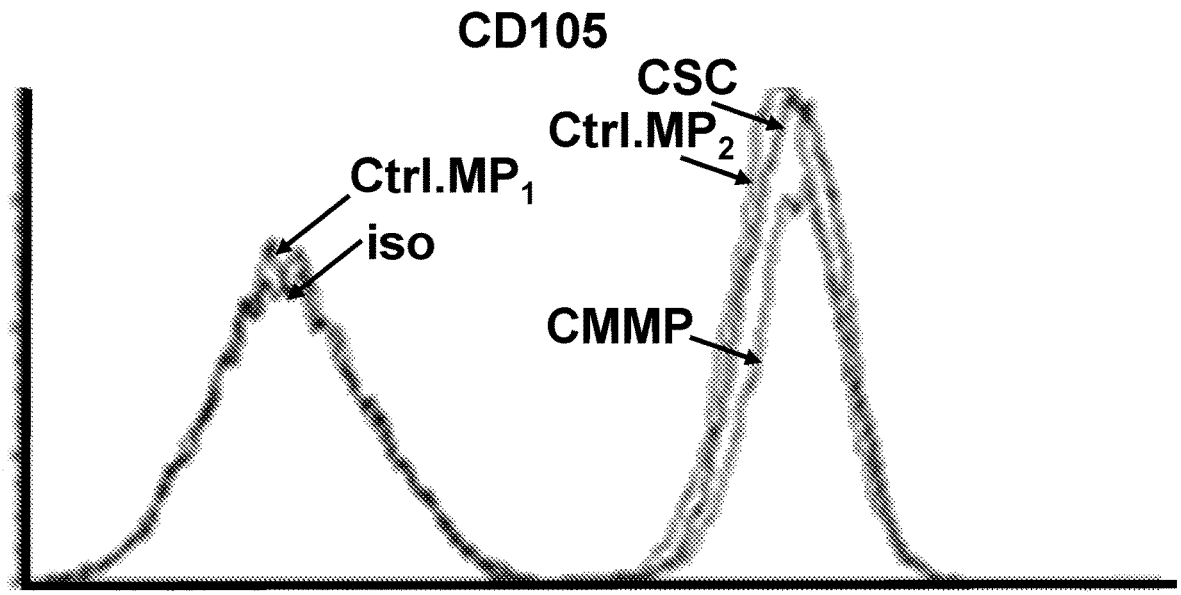
Figure 1G:
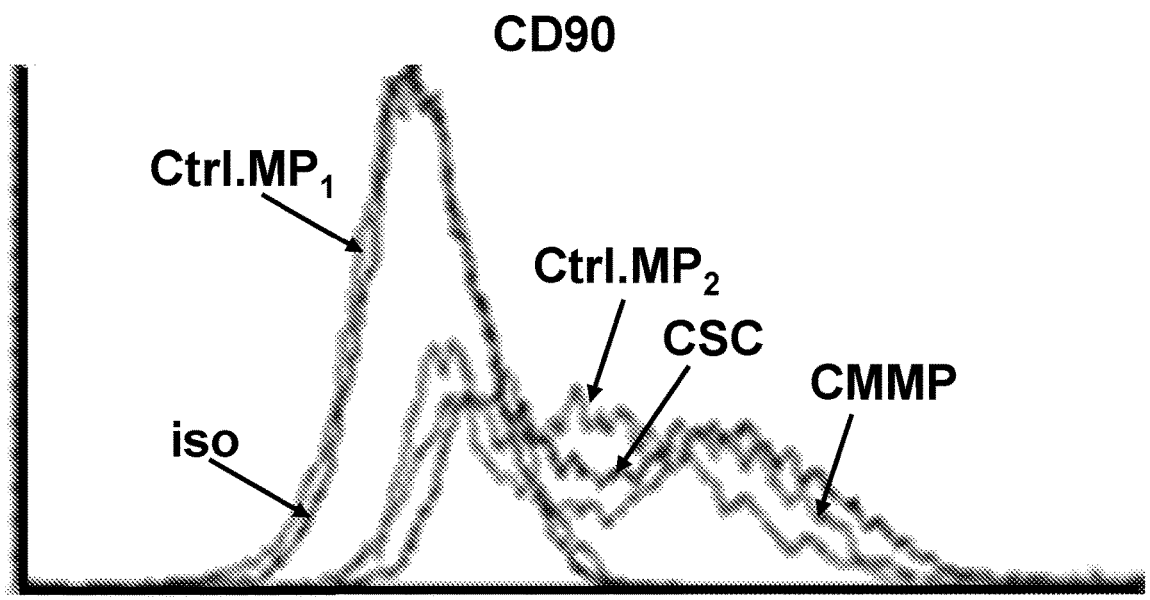
Figure 1H:
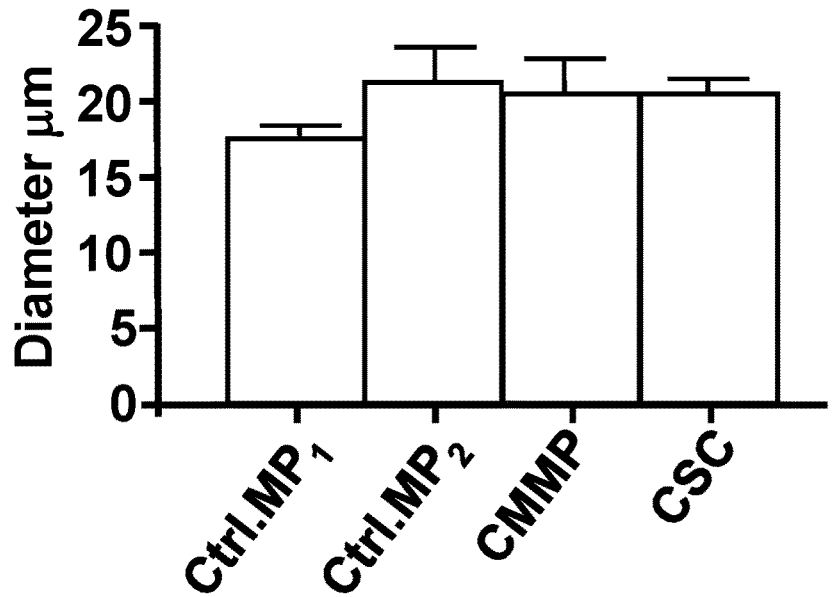
Figure 1I:
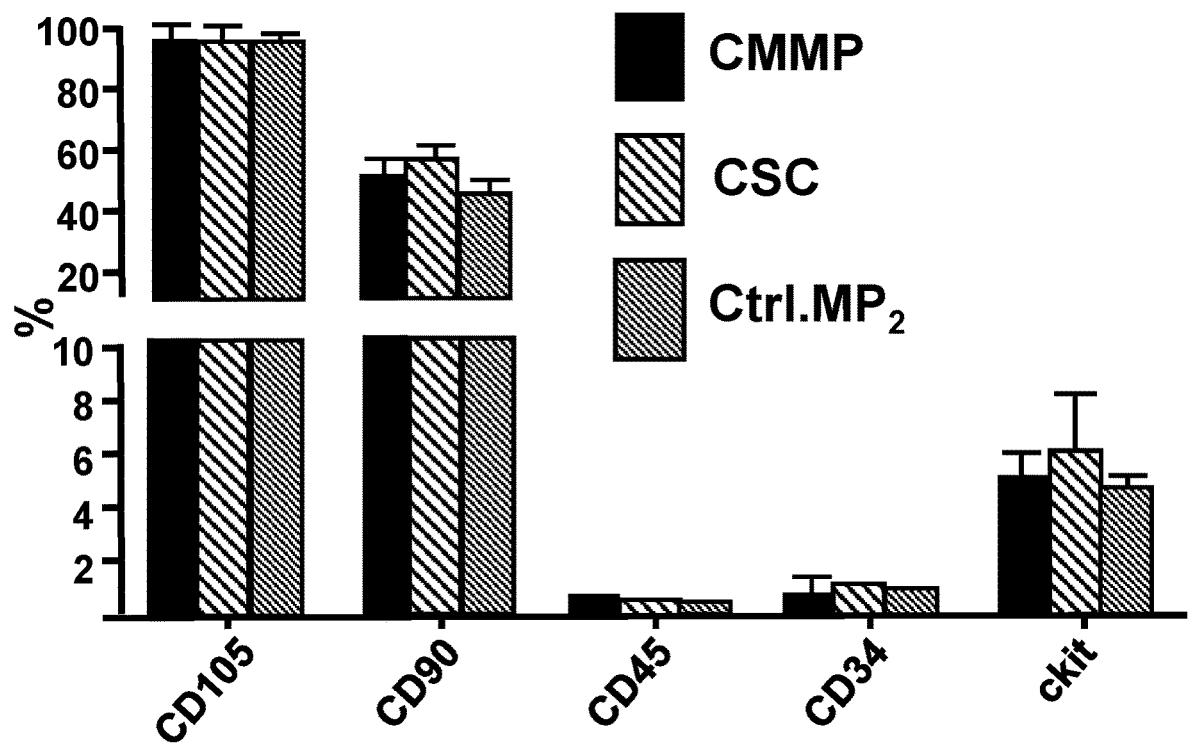
Figure 1J:
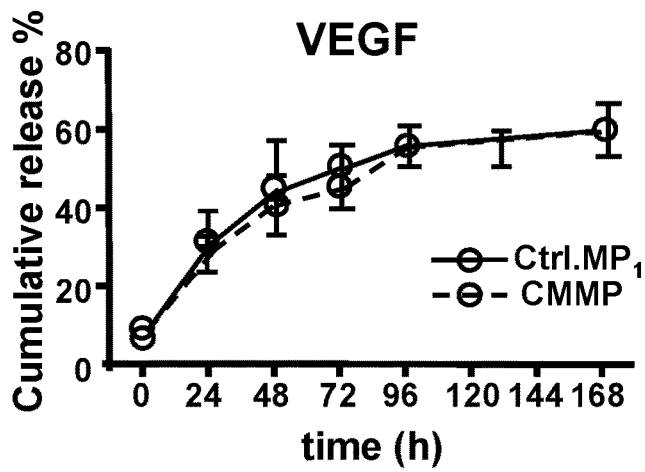
Figure 1K:
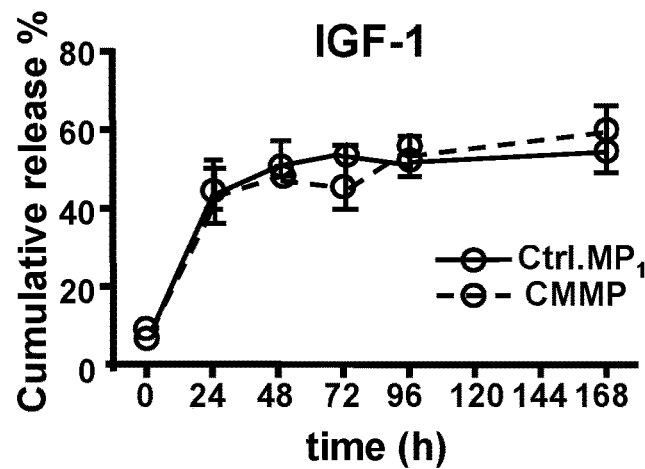
Figure 1L:
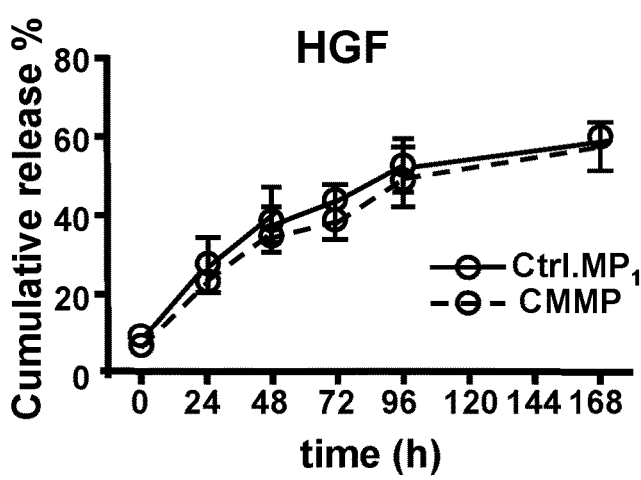
Figure 2A:
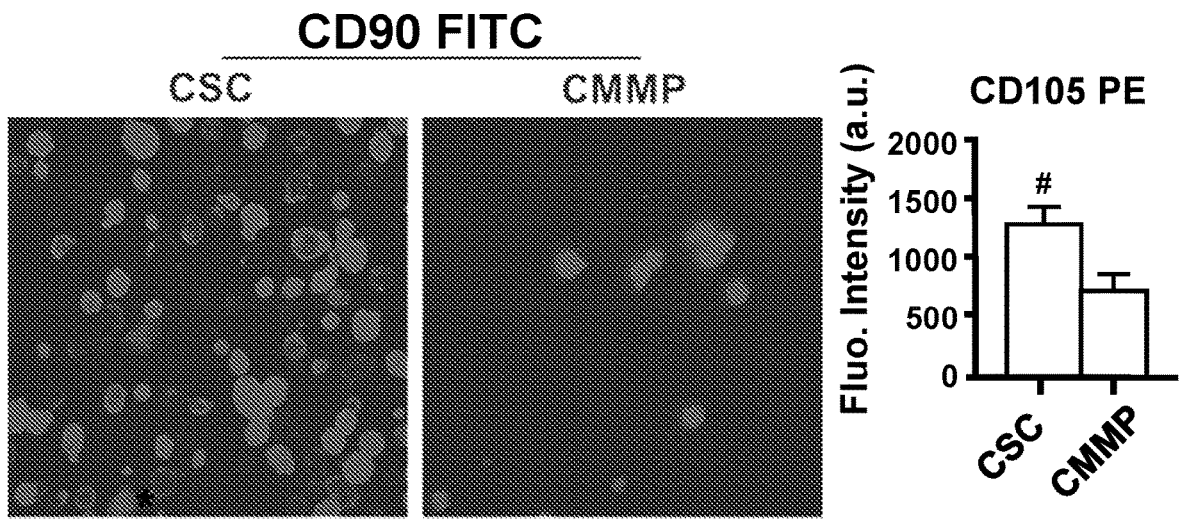
FIGS. 2A and 2B illustrate the fluorescence densities of CD105 and CD90 expressions on cell-mimicking microparticles (CMMPs) and cardiac stem cells (CSCs). n=6 for each group. All data are mean±s.d. * indicating P<0.05 when compared to CMMP group. Comparisons were performed by two-tailed unpaired Student's t-test.
Figure 2B:
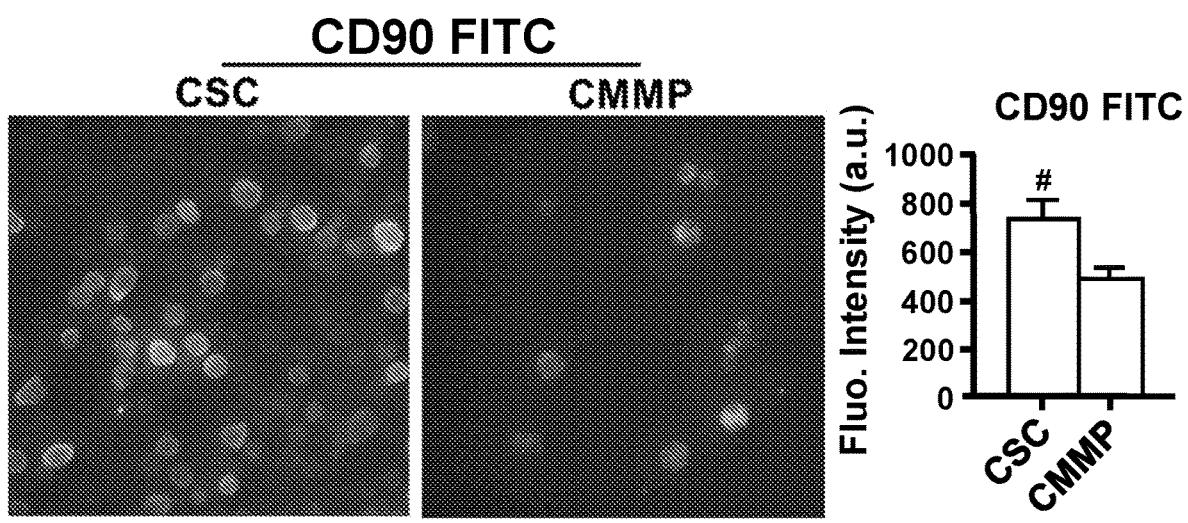
Figure 10A:
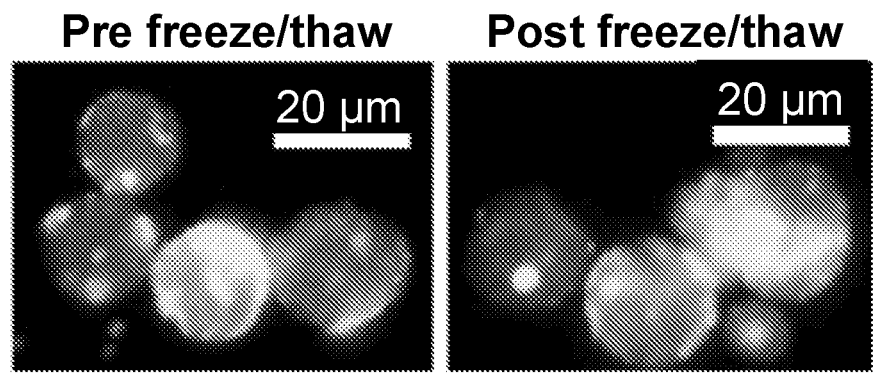
FIGS. 10A-10F illustrate snap freezing in −80° C. and thawing in water did not affect the membrane coating (FIG. 10A), size (FIGS. 10B and 10C), or surface antigen expression of CMMPs (FIGS. 10D-10F).
Figure 10B:
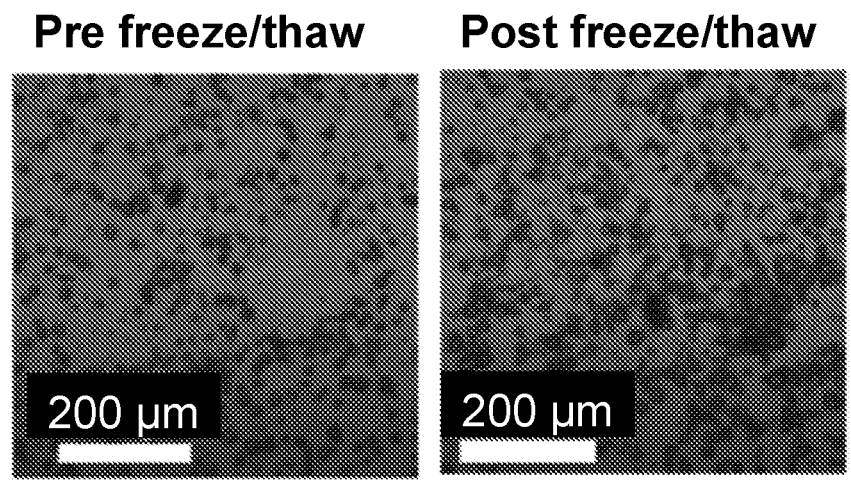
Figure 10C:
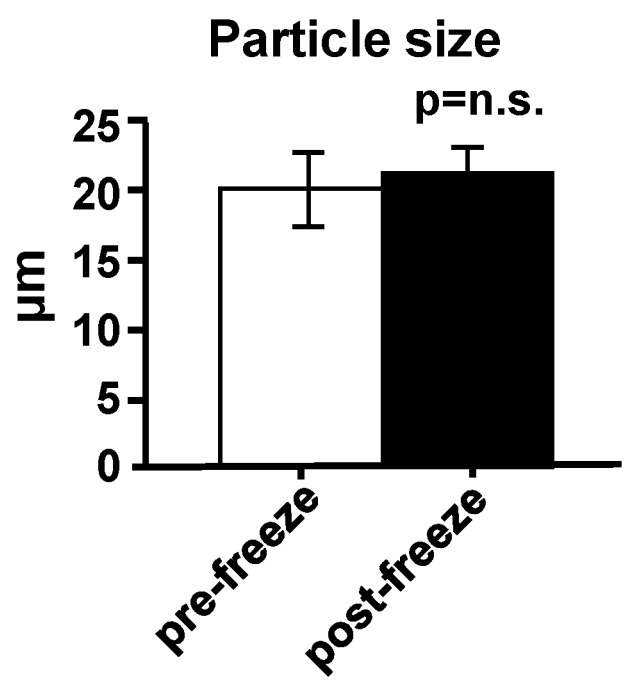
Figure 10D:
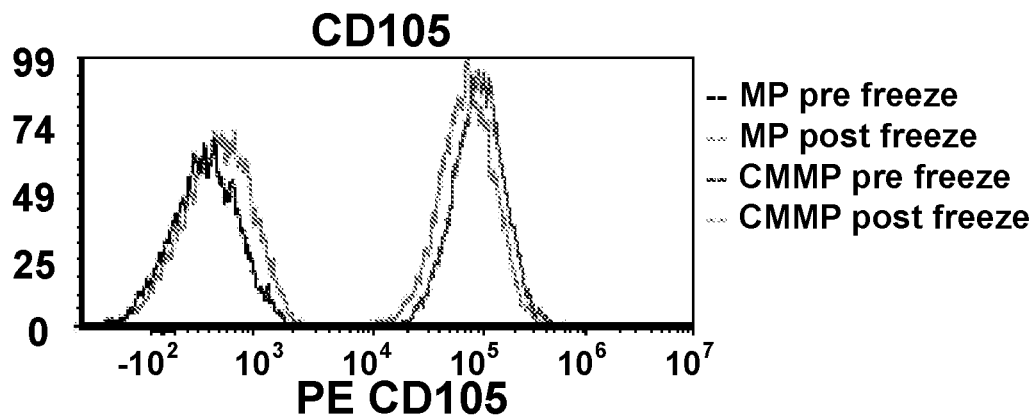
Figure 10E:
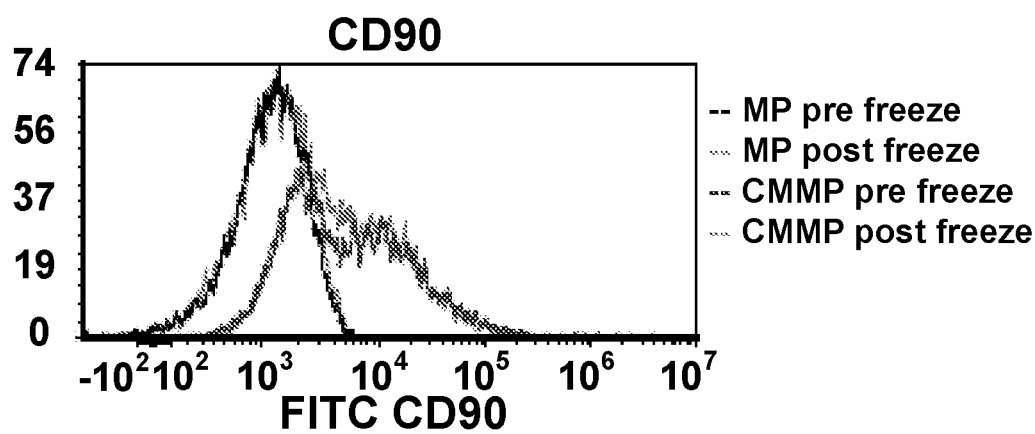
Figure 10F:
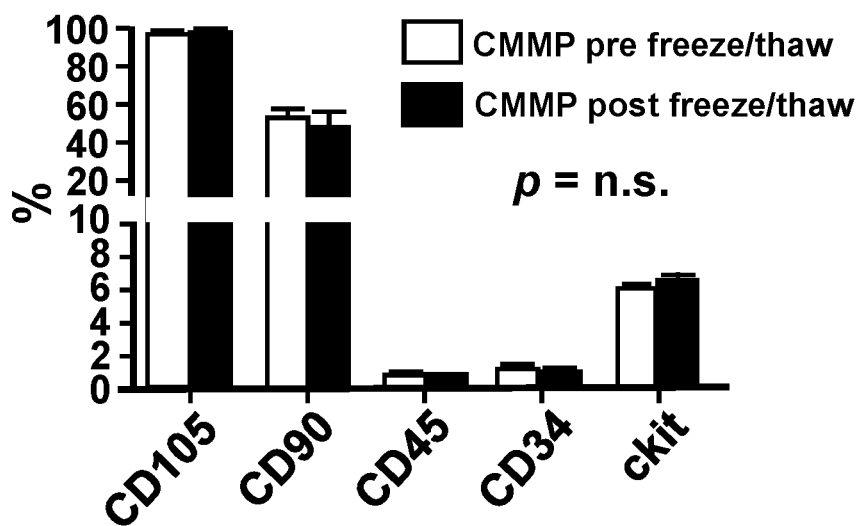

As an indicator of successful membrane cloaking, flow cytometry analysis confirmed the expression of major human CSC markers (e.g. CD105, CD90) on CMMPs and Control $MP_2$ but not on Control $MP_1$ (FIGS. 1F and 1G; FIGS. 2A and 2B). Overall, both CMMPs and Control $MP_2$ carried similar surface antigens as CSCs did (FIG. 1I). Membrane cloaking did not affect the release of CSC factors, namely vascular endothelial growth factor (VEGF), insulin-like growth factor (IGF)-1, and hepatocyte growth factor (HGF) from CMMPs and Control $MP_1$ (FIGS. 1J-1L and 9A-9C). Snap freezing in −80° C. and thawing in water did not affect the membrane coating (FIG. 10A), size (FIGS. 10B and 10C), or surface antigen expression of CMMPs (FIGS. 10D-10F), These results confirmed CMMPs recapitulated the secretome and surface antigen profile of genuine CSCs. In contrast, Control $MP_1$ contained CSC secretome but not the membrane of CSCs, while Control $MP_2$ carried the membrane of CSCs successfully.

Example 15

Figure 3A:
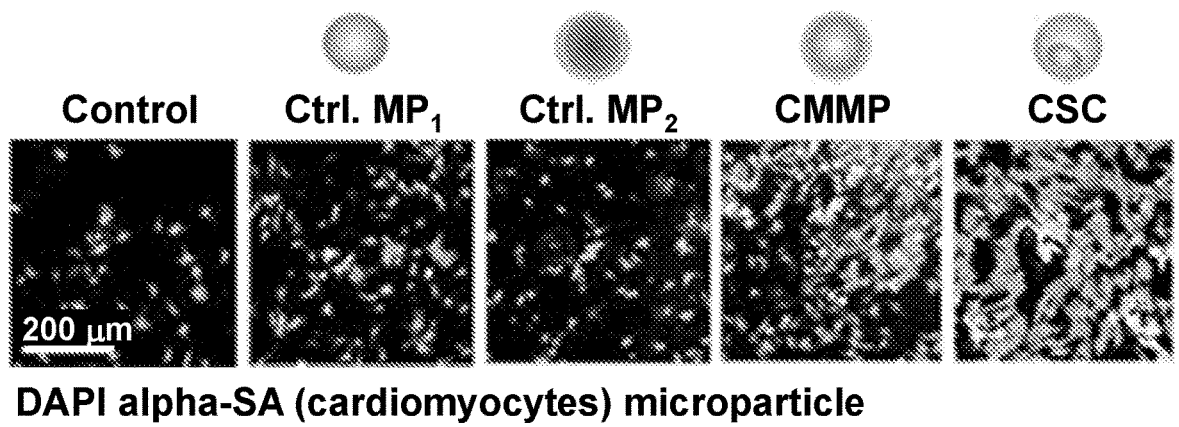
FIGS. 3A-3H illustrate the effects of cell-mimicking microparticles (CMMPs) on neonatal rat cardiomyocytes (NRCM) functions in vitro.

CMMPs Promote Cardiomyocyte Functions In Vitro:

An important potency indicator of CSCs is their ability to promote the functions of in vitro-cultured cardiomyocytes. CMMPs, Control $MP_1$, Control $MP_2$, or CSCs (FIG. 3A) were co-cultured with neonatal rat cardiomyocytes (NRCMs) (stained for alpha-sarcomeric actin, FIG. 3A) in plain Iscove's Modified Dulbecco's Medium (IMDM). Solitary NRCM culture was included as the negative control.

Figure 3B:
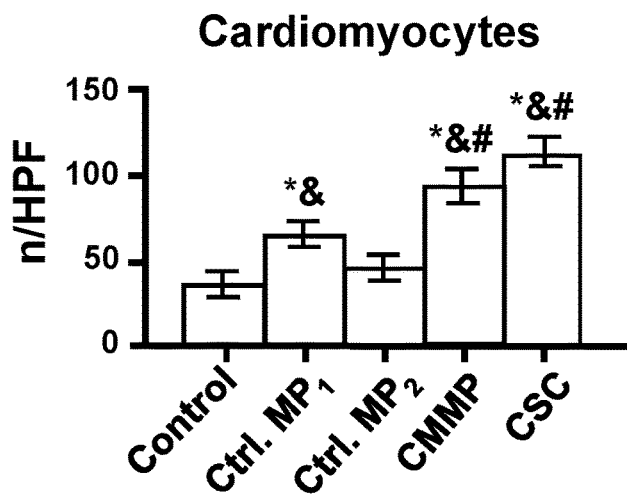
Figure 3C:
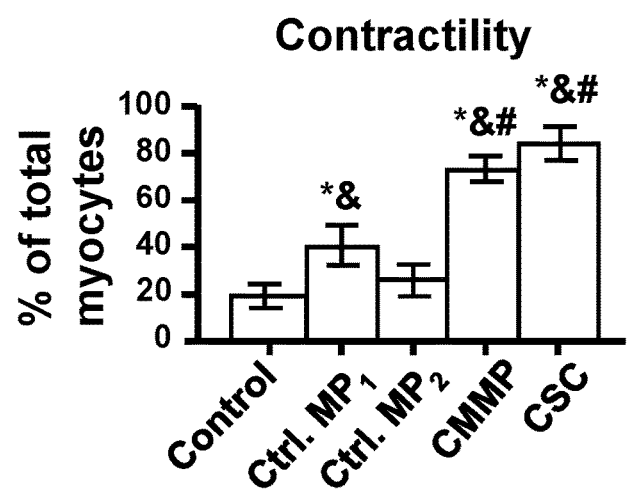
Figure 3D:
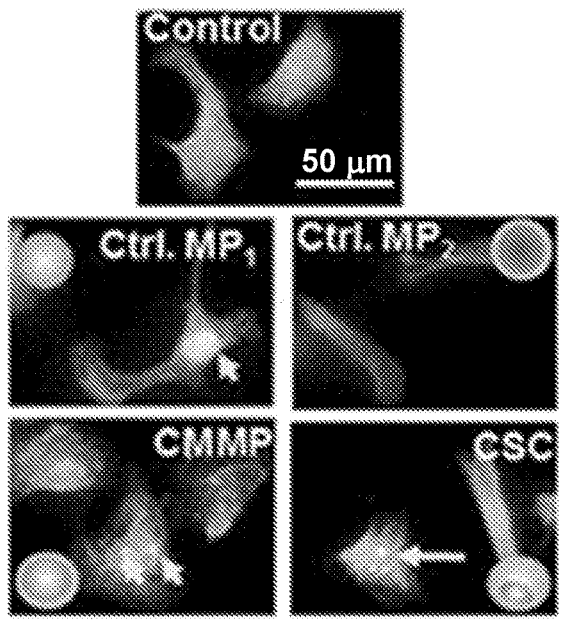
Figure 3D:
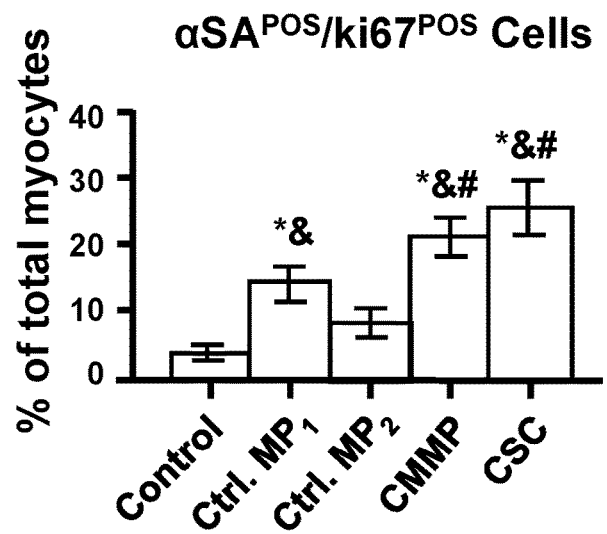
Figure 3E:
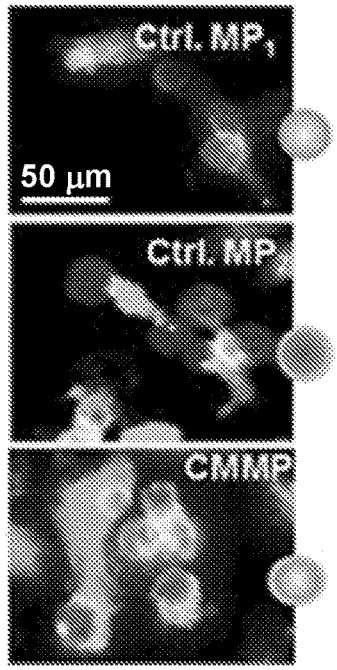
Figure 3E:
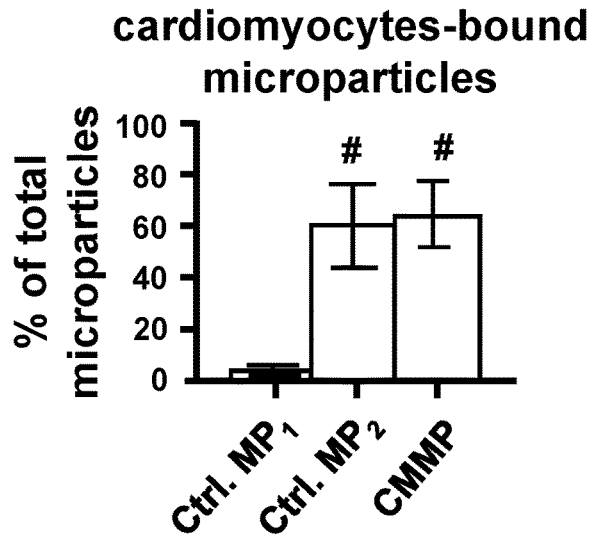
Figure 3F:
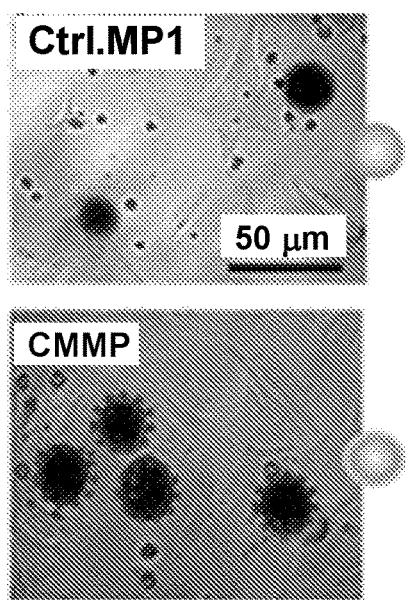
Figure 3F:
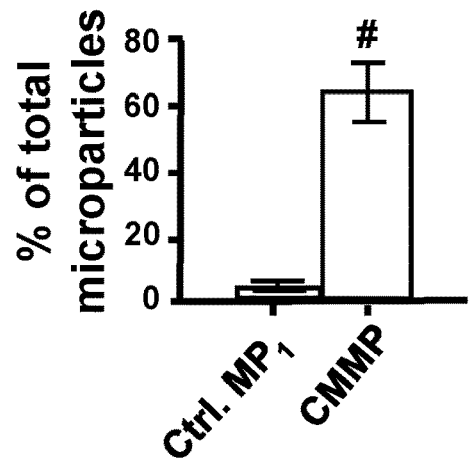
Figure 3G:
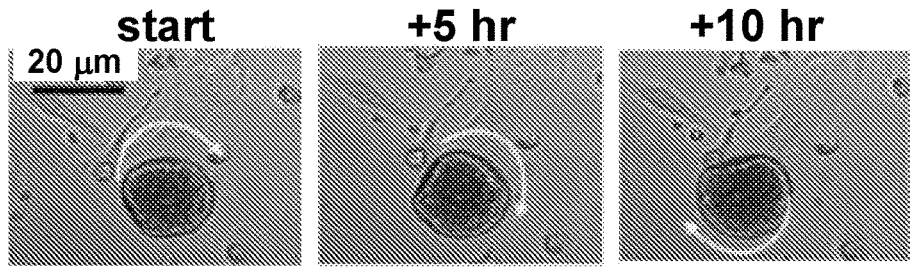
Figure 3H:
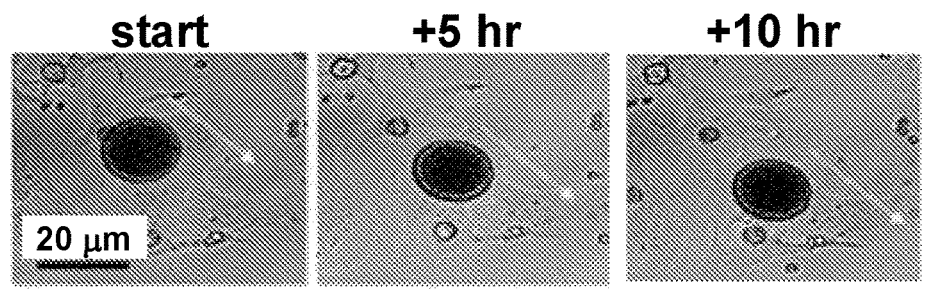

While Control $MP_1$ (FIG. 3B) increased the numbers of NRCMs as compared to those from Control $MP_2$ or solitary NRCM culture, the greatest NRCM numbers were seen in those co-cultured with CMMPs and genuine CSCs (blue bar, FIG. 3B). Furthermore, CMMPs and Control $MP_1$ robustly promoted NRCM contractility and proliferation (as indicated by Ki67-positive nuclei, FIG. 3D). Both CMMPs and Control $MP_2$ could firmly bind to cardiomyocytes, as cells did, while most non-cloaked Control $MP_1$ floated in the media (FIG. 3E). Such binding was confirmed by CMMPs' synchronized movement with adjacent beating cardiomyocytes (FIG. 3F). Moreover, time-lapse imaging revealed the rolling (FIG. 3G) and traveling (FIG. 3H) of CMMPs on attached cardiomyocytes, suggesting the biointerfacing between CMMPs and cardiomyocytes. Such dynamic activities were not seen in non-cloaked Control $MP_1$. These in vitro cell-based assays suggest the regenerative potential of CMMPs in the heart.

Example 16

Figure 4A:
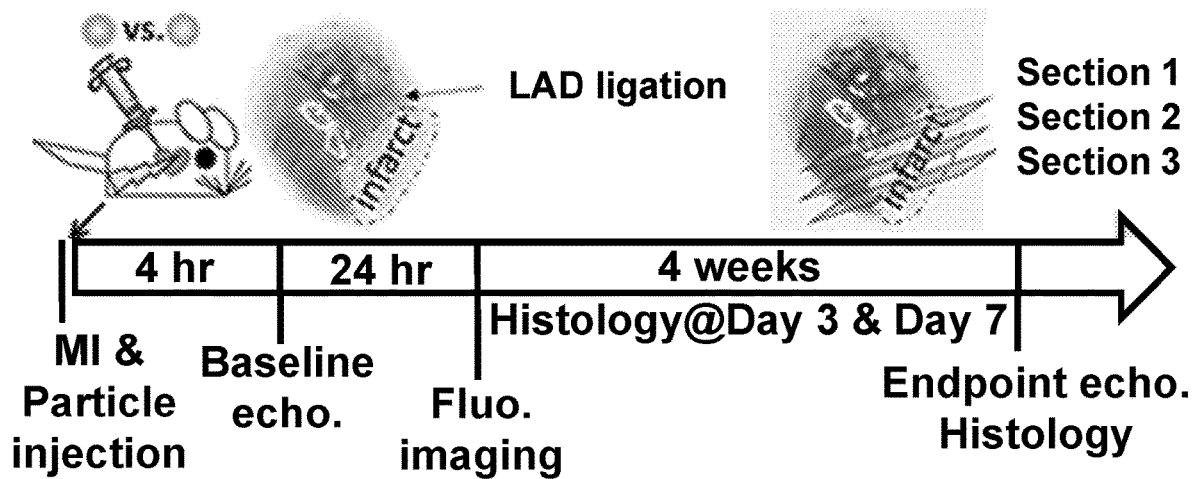

Therapeutic Benefits of CMMP Injection in a Mouse Model of Heart Attack:

To test the therapeutic potential of CMMPs, a mouse model of myocardial infarction (heart attack) by left anterior descending artery (LAD) ligation was used (FIG. 4A). CMMPs or Control $MP_1$ were intramyocardially injected immediately after LAD ligation. Negative or positive control animals received injection of vehicle (PBS) or CSCs, respectively.

Figure 4B:
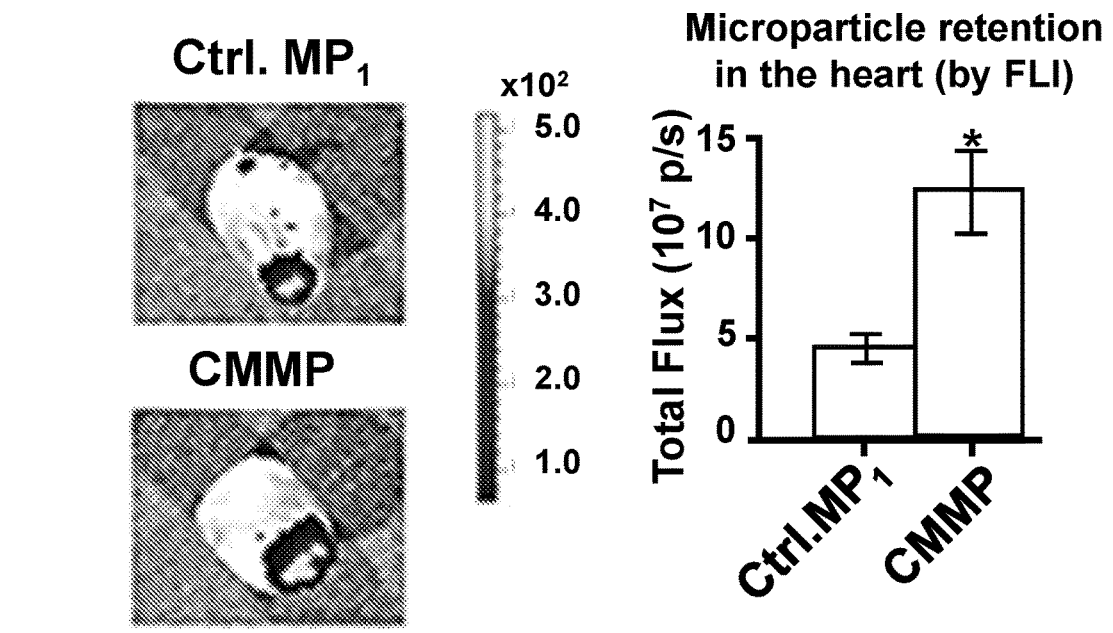
Figure 4C:
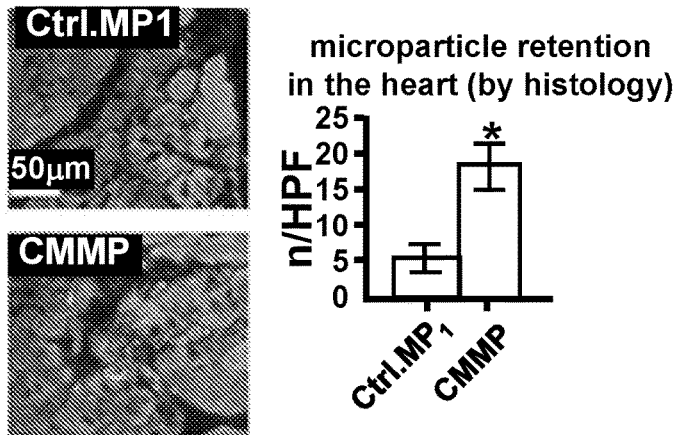
Figure 11:
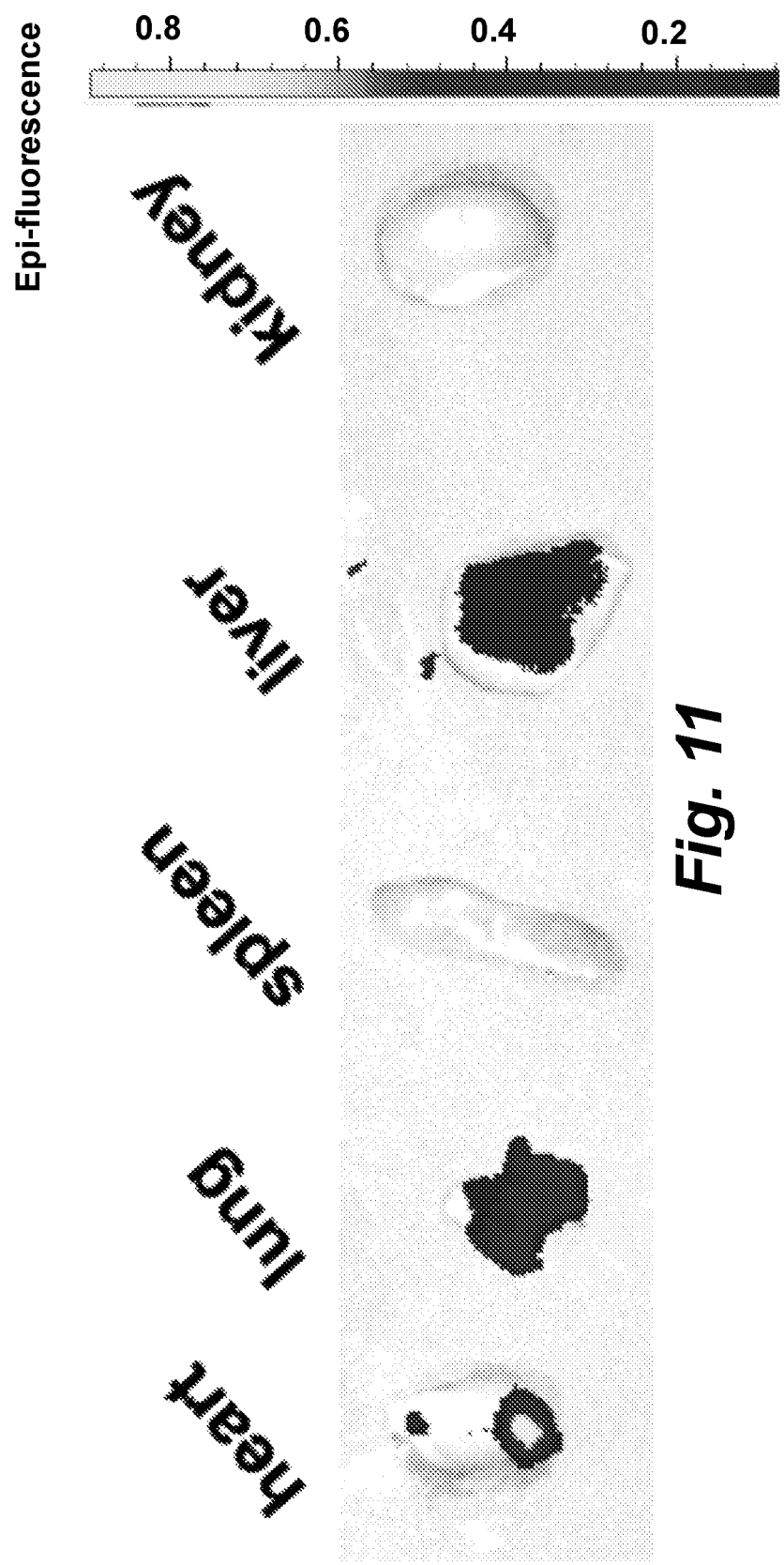
FIG. 11 is a series of digital images illustrating ex vivo fluorescent imaging showing that the majority of CMMPs remained in the heart after injection, while "washed away" CMMP signal could be found in the lung and the liver.

Ex vivo fluorescent imaging at Day 3 revealed that more CMMPs were retained in the heart after injection than Control $MP_1$ (FIG. 4B) were. This was further confirmed by histology (FIG. 4C). This was consistent with CMMP's superior binding to cardiomyocytes in vitro (as seen in FIGS. 3A-3H). In addition, ex vivo fluorescent imaging indicated that the majority of CMMPs remained in the heart after injection, while "washed away" CMMP signal could be found in the lung and the liver, as shown in FIG. 11, consistent with the notion that the needle injection can cause vessel damage and the venous drainage brings the particles to the lungs (Al Kindi et al., (2008) *Front. Biosci.* 13: 2421-2434). The off-target expression in the liver may represent the leakage of CMMPs into the LV cavity during injection. Nevertheless, the majority of CMMPs remains in the heart after injection.

Figure 4D:
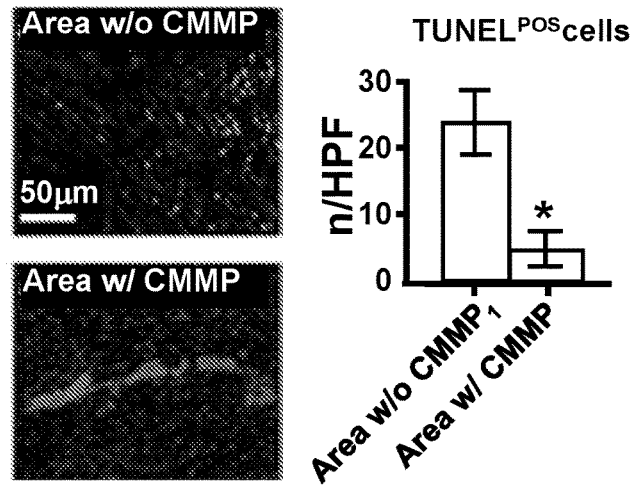
Figure 4E:
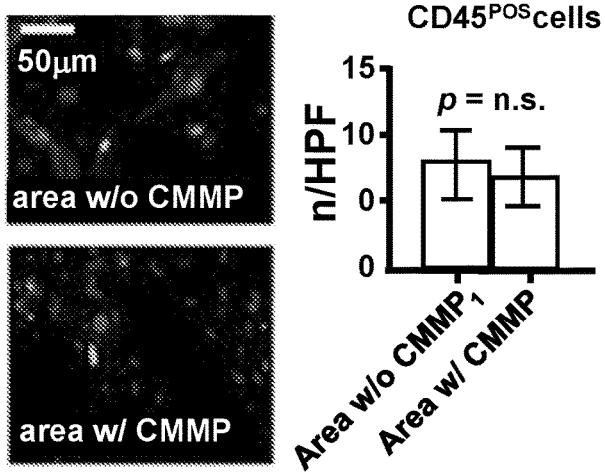
Figure 12:
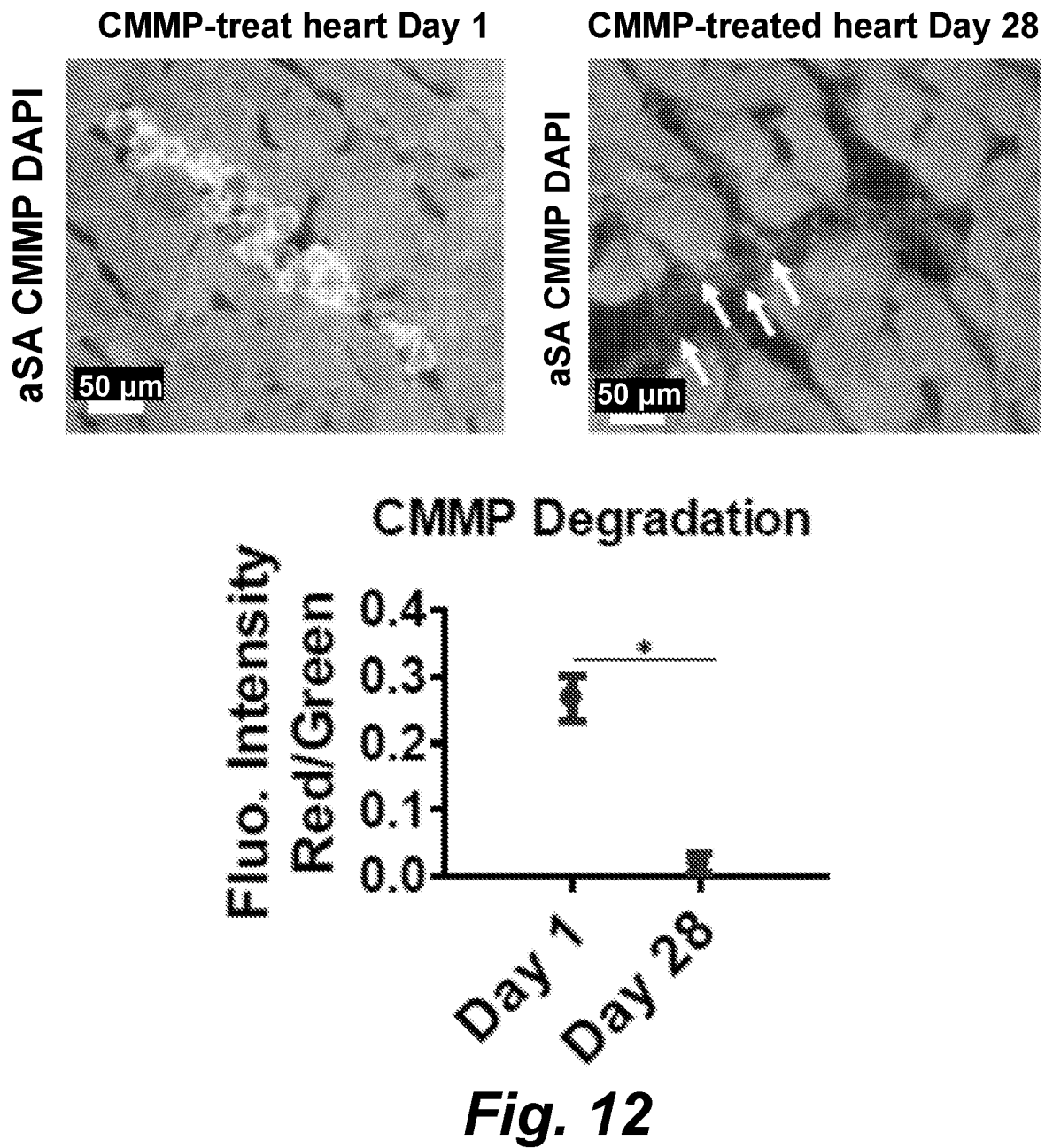
FIG. 12 illustrates in vivo degradation of CMMPs evident as only negligible amount of particles remaining in the heart at Day 28.

In vivo degradation of CMMPs were evident as only negligible amount of particles remained in the heart at Day 28, as shown in FIG. 12. A cohort of animals were sacrificed at Day 7 for assessment of myocardial tissue apoptosis and infiltration of macrophages in CMMP-treated animals. TUNEL staining revealed the anti-apoptosis effects of CMMP: less apoptotic nuclei were detected in area with the CMMP presence (FIG. 4D). CMMP treatment did not cause exacerbation of inflammation: the tissue density of CD45-positive cells was indistinguishable in area with or without CMMPs (FIG. 4E).

Figure 4F:
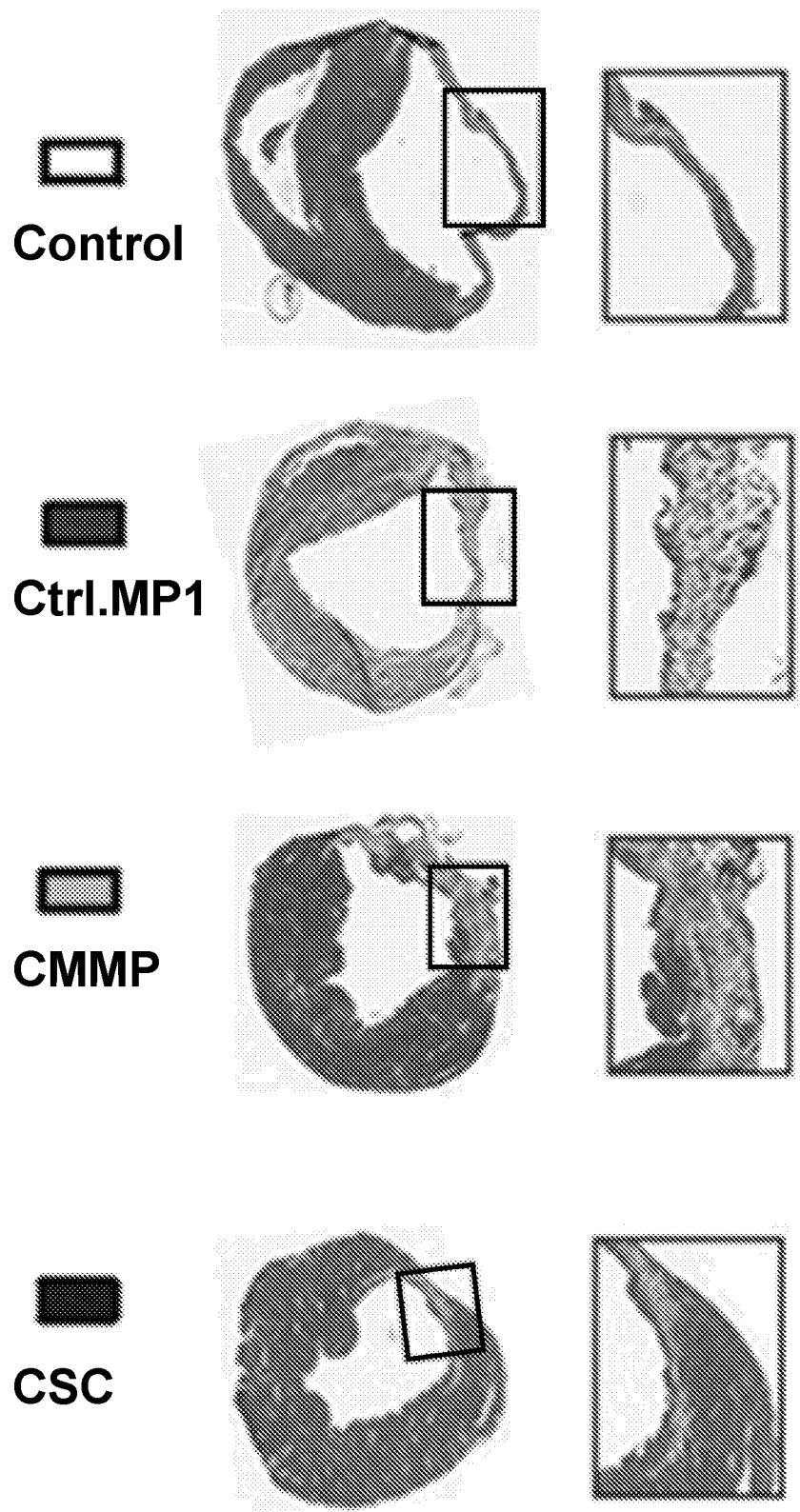

Masson's trichrome staining 4 weeks after treatment (FIG. 4F) revealed Control $MP_1$ treatment (FIGS. 4G-4I) exhibited a certain degree of heart morphology protection compared to Control PBS injections. However, the greatest protective effects were seen in the animals treated with CMMPs. Such protection effects were similar to those injected with CSCs.

The bona fide efficacy indicator for stem cell therapy is the ability to ameliorate ventricular dysfunction or even boost cardiac function over time, gauged by echocardiography. Left ventricular ejection fractions (LVEFs) were measured at baseline (4 h post infarct) and 4 weeks afterwards. LVEFs were indistinguishable at baseline for all groups (FIG. 4J), indicating a similar degree of initial heart injury.

Over the 4 week period, the LVEFs in control (PBS or saline)-treated animals continued deteriorating (FIG. 4K) while the Control $MP_1$-treated animals exhibited a trend of LVEF augmentation but did not reach statistical significance. CMMP treatment robustly boosted cardiac function with the highest LVEFs at 4 weeks (FIG. 4K). Such treatment effects were indistinguishable with those treated with real CSCs (FIG. 4K).

Figure 5A:
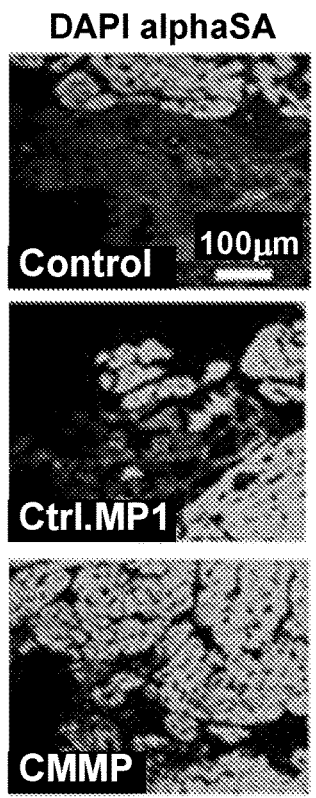
FIGS. 5A-5D illustrate the injection of cell-mimicking microparticles (CMMPs) promotes remuscularization, myocyte proliferation, and angiogenesis.
Figure 5A:
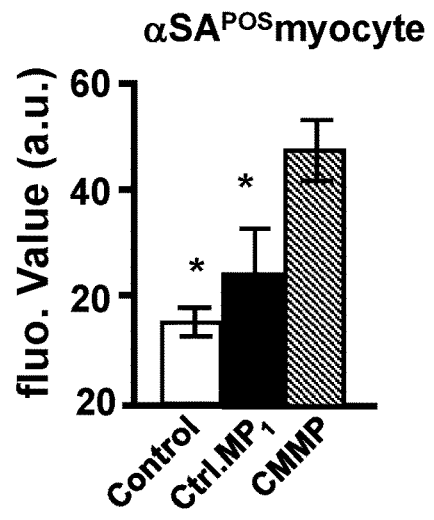
Figure 5B:
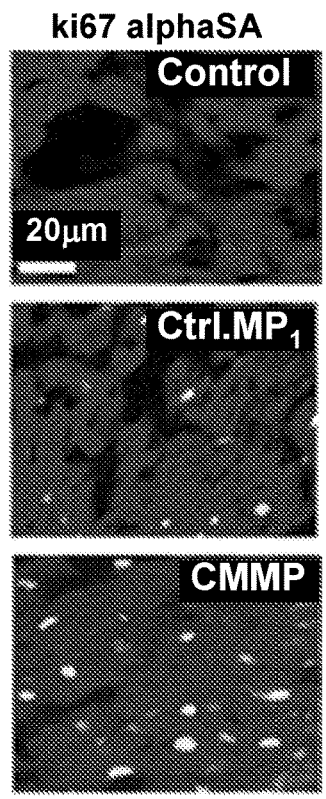
Figure 5B:
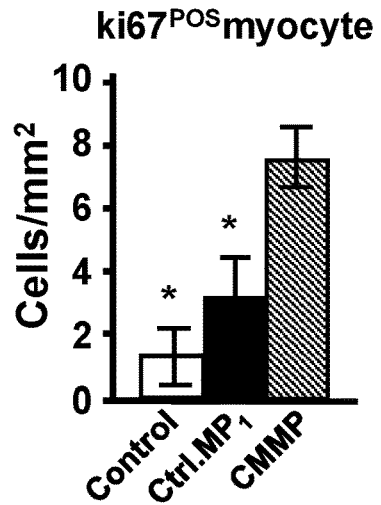
Figure 5C:
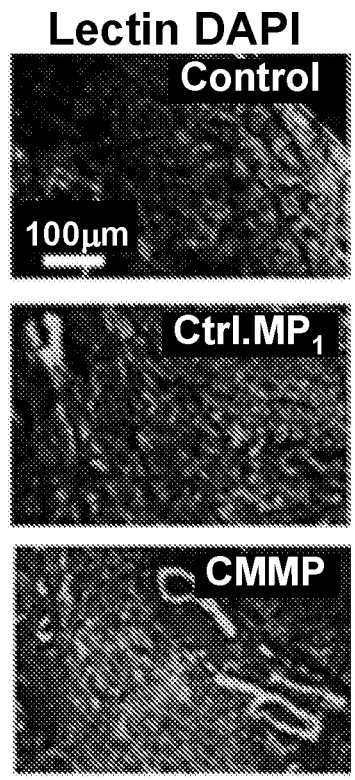
Figure 5C:
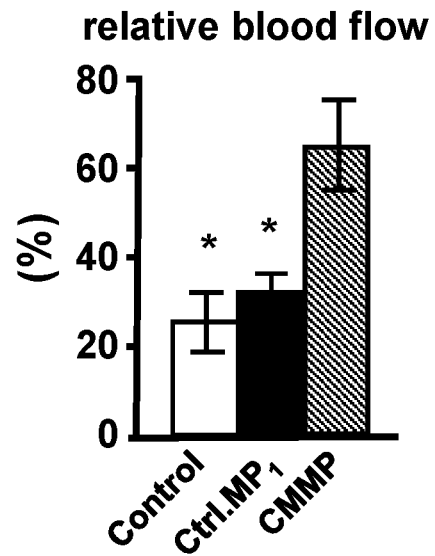
Figure 5D:
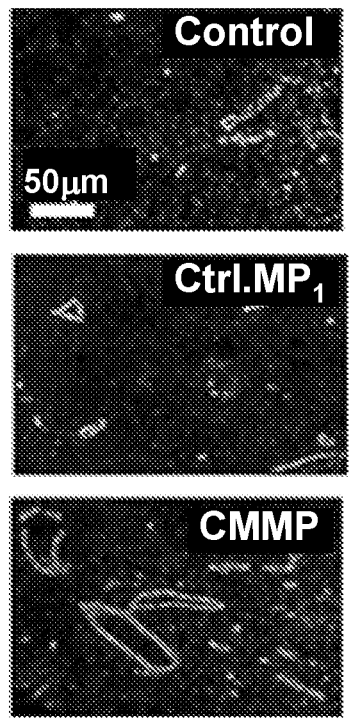
Figure 5D:
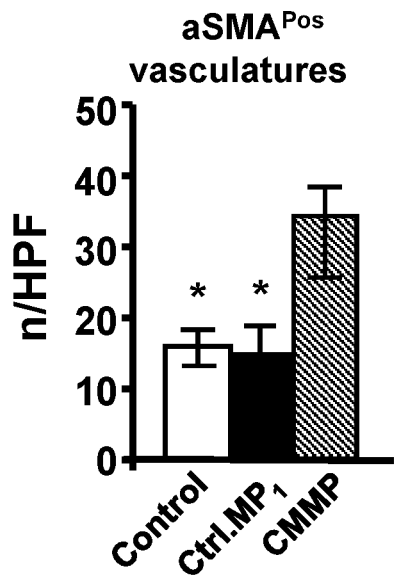

Histological analysis indicated that such functional benefits by CMMP treatment were accompanied by remuscularisation (FIG. 5A), proliferation of endogenous cardiomyocytes (FIG. 5B), augmentation of blood flow (FIG. 5C), and increase of vessel density (FIG. 5D) in the post-MI heart.

Example 17

Figure 6A:
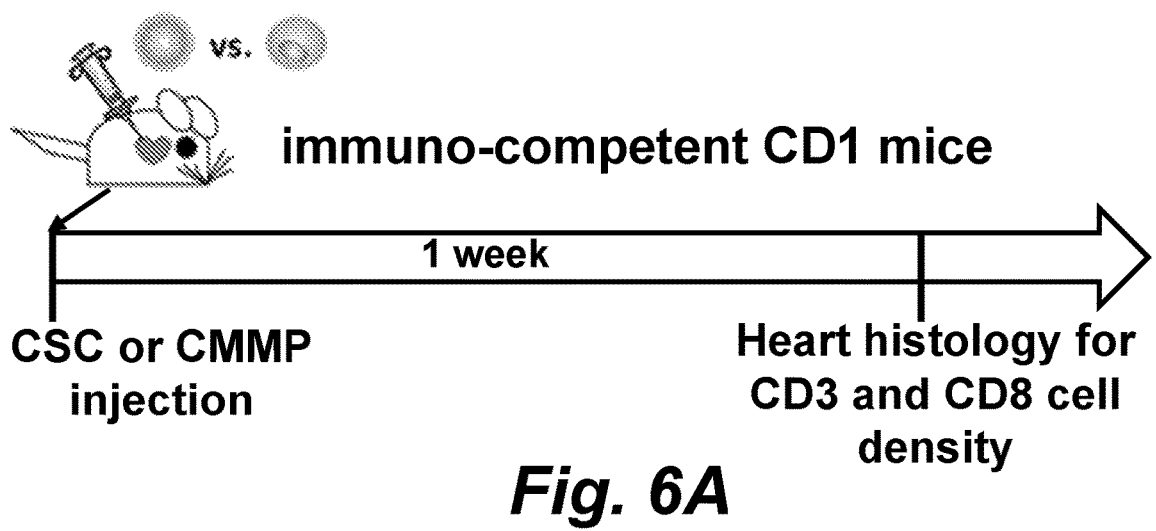
FIGS. 6A-6G illustrate cell-mimicking microparticles (CMMPs) injection does not stimulate local T cell immune response in immunocompetent mice.

CMMP Injection does not Promote T Cell Infiltration:

To evaluate the local T cell immune response to CMMPs, immune-competent CD1 mice were intramyocardially injected with human CSCs or CMMPs. Animals were sacrificed 7 days after injection for assessment of T cell immune rejection in the heart, as gauged by $CD3^+$ and $CD8^+$ T cells (FIG. 6A). CMMP (red) injection elicited negligible T cell rejection as very few $CD3^+$ or $CD8^+$ T cells were detected in the heart (FIGS. 6C and 6E).

Figure 6B:
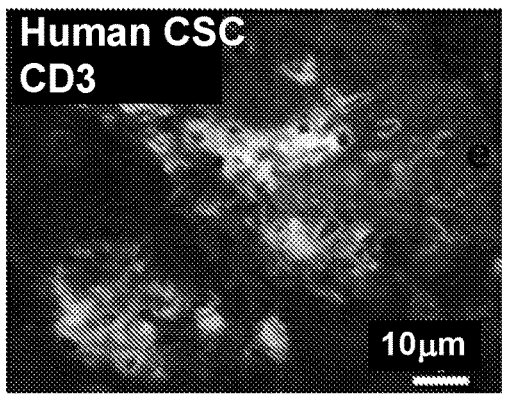
Figure 6C:
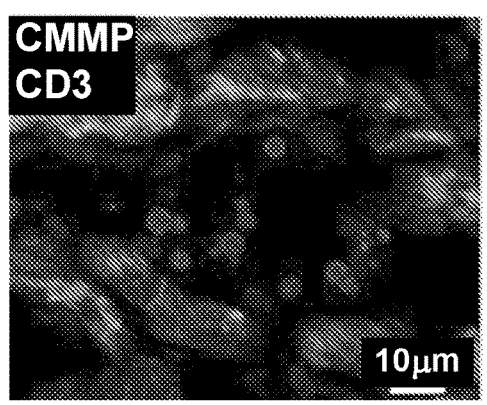
Figure 6D:
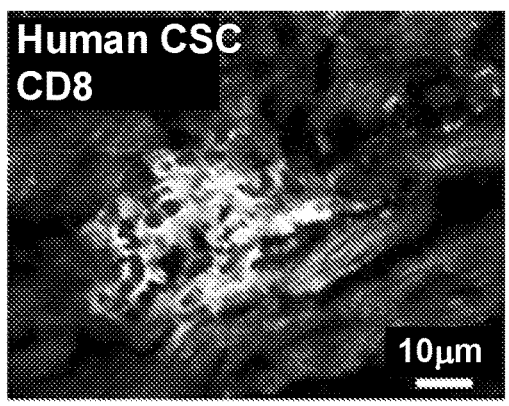
Figure 6E:
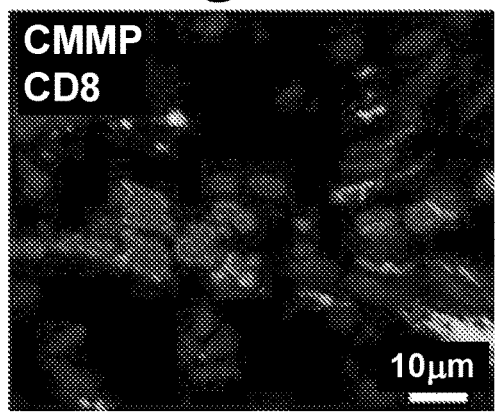
Figure 6F:
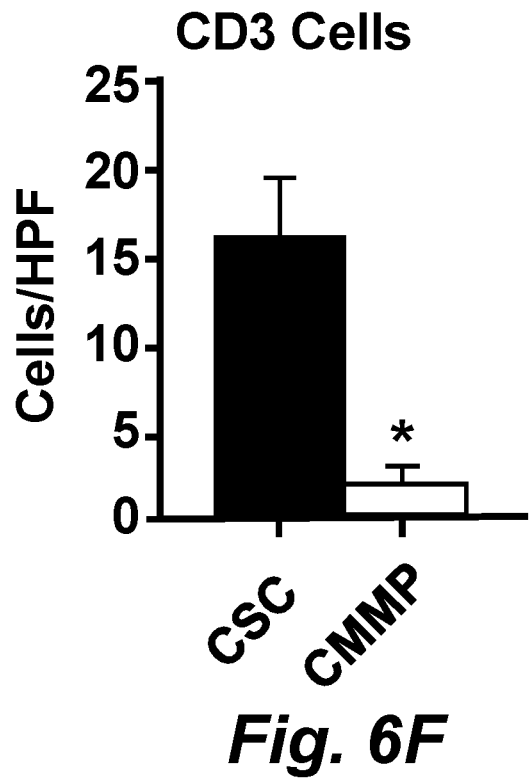
Figure 6G:
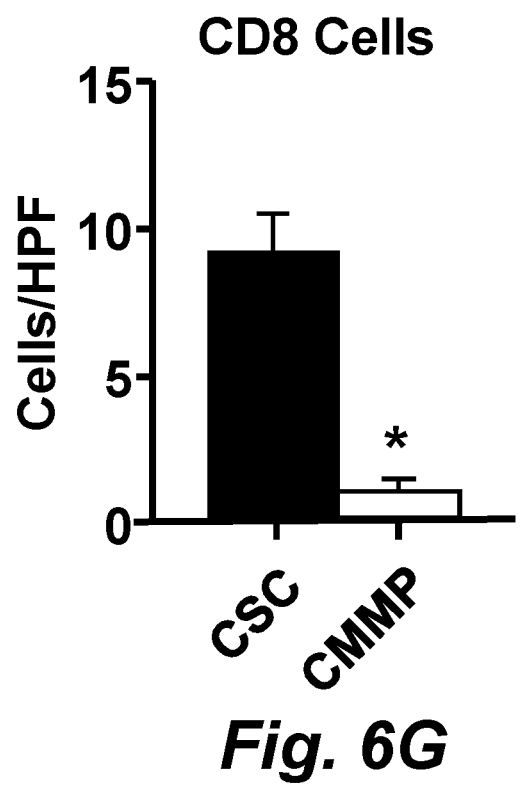

In contrast, severe rejection was detected in mouse hearts treated with human CSCs: engrafted CSCs were surrounded by clusters of $CD3^+$ or $CD8^+$ T cells (FIGS. 6B and 6D). Quantitative analysis also confirmed that CMMP stimulated less local T cell infiltration as compared to the severe T cell stimulation by human CSCs (FIGS. 6F and 6G).

Example 18

A comparison between the CMMP of the disclosure and stem cells is outlined in Table 1.

TABLE 1

| Characteristics | Stem Cells | Cell-mimicking microparticles (CMMPs) |
| --- | --- | --- |
| Secretion of regenerative factors | Yes | Yes |
| Binding to host cells | Yes | Yes |
| Ability to differentiate into host cells | Yes (but rare) | No |
| Ability to proliferate | Yes (limited proliferation in vivo) | No |
| Ability to leave blood vessels after delivery | Yes | Yes |
| Therapeutic benefits in myocardial infarction | Yes | Yes |
| Cryopreservation and storage without affecting quality | No | Yes |
| Stimulate local T cell immune response | Yes | No |

Example 19

Figure 13A:
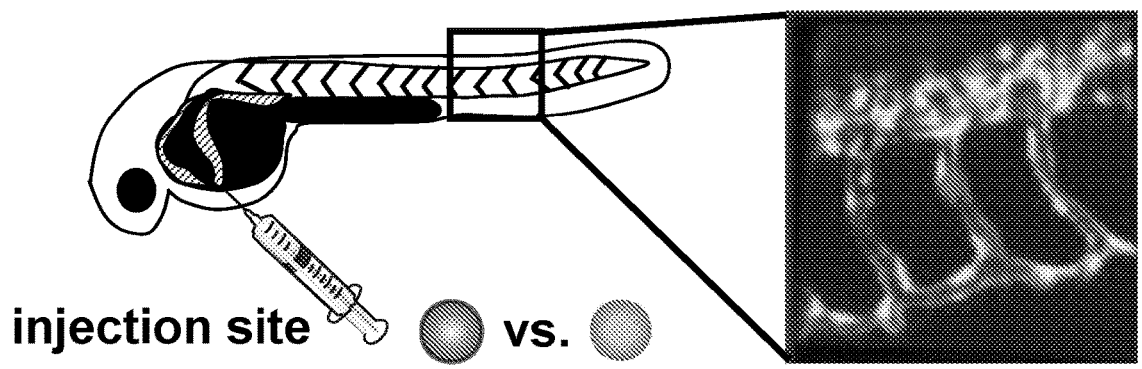
FIG. 13A illustrates the extravasation of CMMPs through active vascular expulsion after intravenously injecting at 48 h post fertilization (hpf) Texas red fluorescent MPs or CMMPs into fli1a:egfp zebra fish embryos overexpressing green fluorescent protein (GFP) in its vasculatures.
Figure 13B:
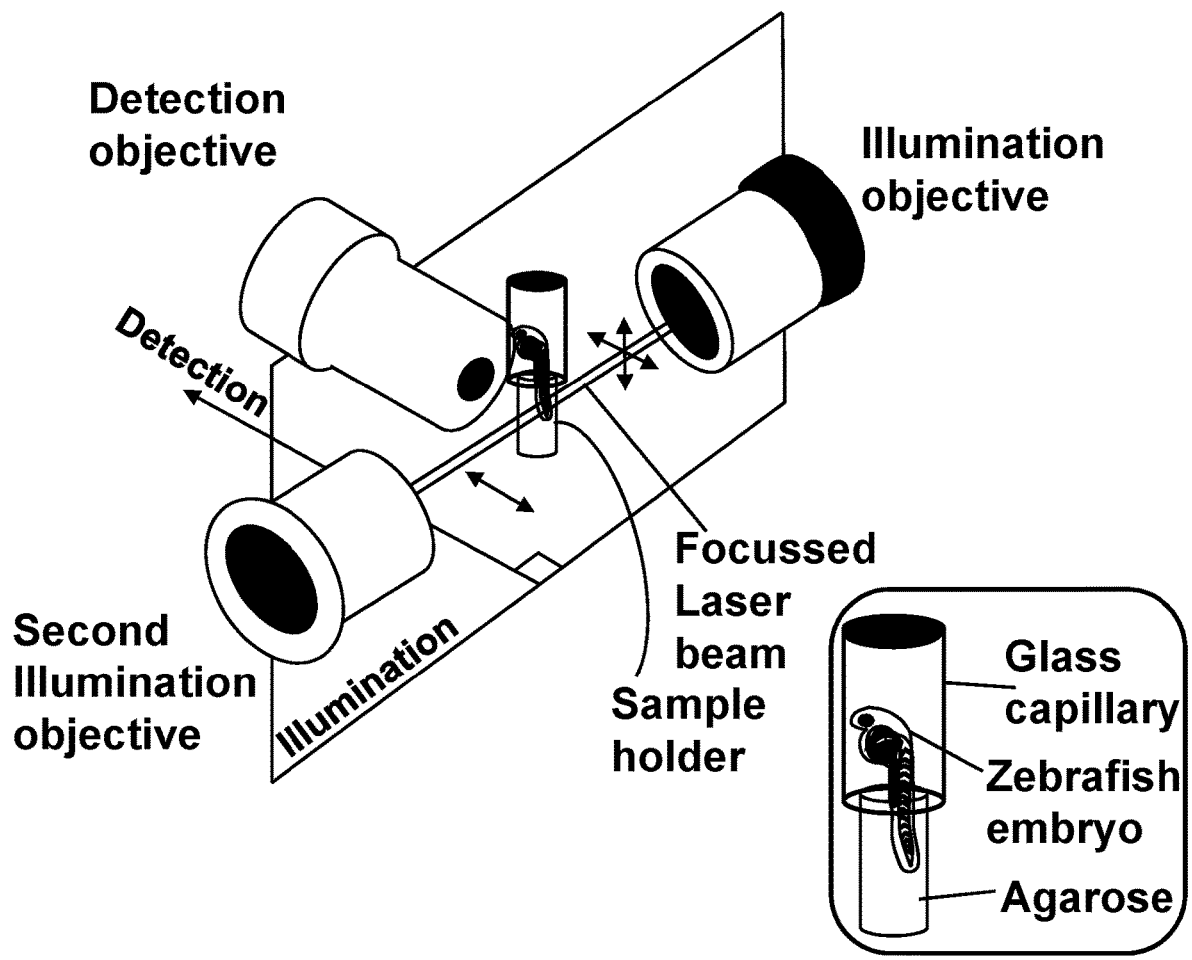
FIG. 13B illustrates the tail intersegmental vessels digitally imaged using light sheet microscopy for the observation of particle extravasation.
Figure 13C:
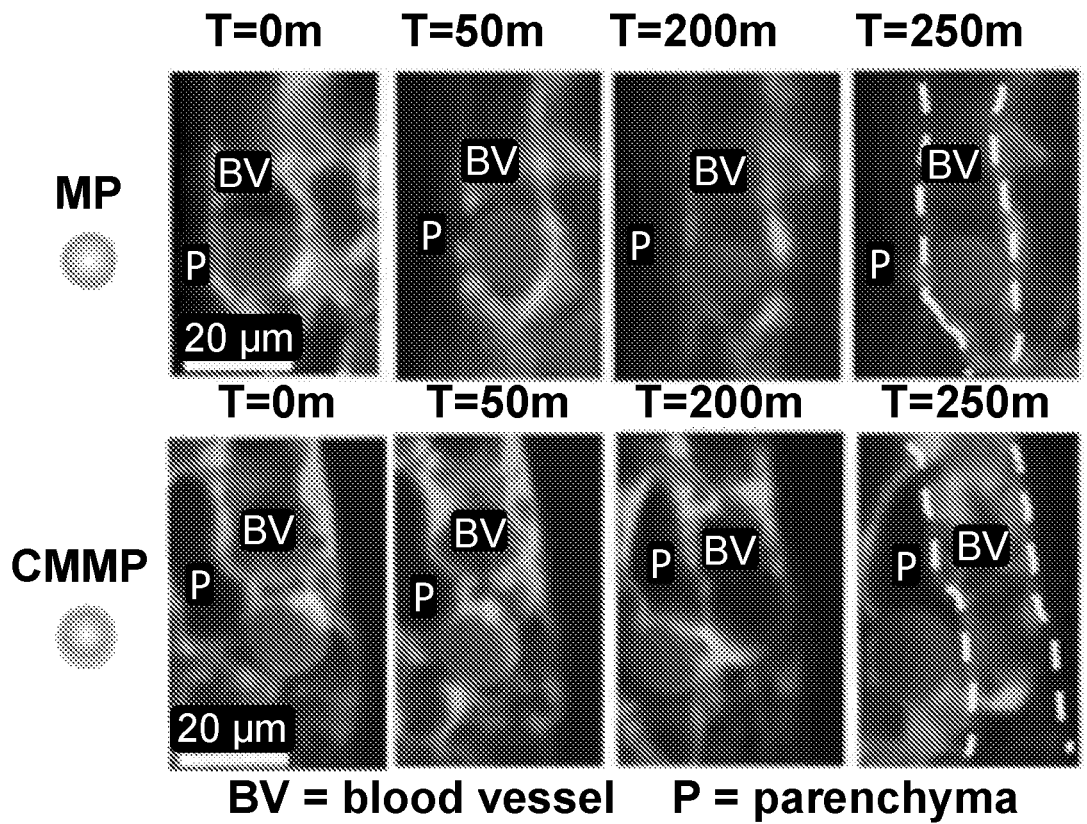
FIG. 13C illustrates that non-coated MPs remained in the blood vessel and did not extravasate over the observation period (upper panel), while CMMPs were observed to extravasate with a multistep active vascular expulsion process (lower panel)
Figure 13D:
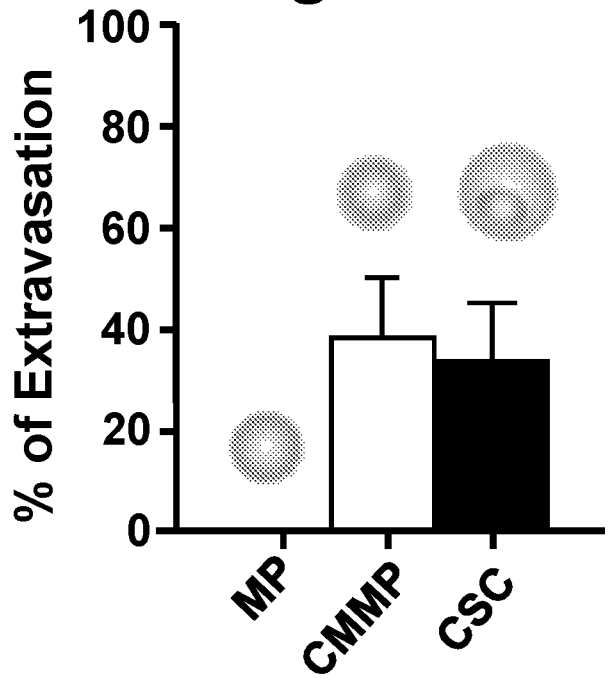
FIG. 13D illustrates that the overall extravasation efficiency for CMMPs was approximately 40% as compared to MPs' failure (0%) to extravasate.

Extravasation of Intravenously-Delivered CMMPs Through Active Vascular Expulsion:

Intramyocardial injection of stem cells normally involves traumatic open-chest surgery, which limits its translation to the clinic. Intravenous injection represents a minimally-invasive and safe route to deliver therapeutic stem cells for multiple diseases. In order for stem cells to reach the parenchyma for repair they have to cross the vascular barrier (i.e. extravasation) either through diapedesis or active vascular expulsion. Unlike live cells, inert polymer MPs cannot extravasate, limiting their potential to be applied intravenously. To test this hypothesis that CMMPs could extravasate through active vascular expulsion we intravenously injected Texas red fluorescent MPs or CMMPs into fli1a:egfp zebra fish embryos at 48 h post fertilization (hpf). This fish line overexpressed green fluorescent protein (GFP) in its vasculatures (FIG. 13A). After infusion, the tail intersegmental vessels were imaged using light sheet microscopy (FIG. 13B) for the observation of particle extravasation. As a result, non-coated MPs remained in the blood vessel and did not extravasate over the observation period (FIG. 13C, upper panel). In contrast, CMMPs were observed to extravasate with a multistep active vascular expulsion process (FIG. 13C lower panel): first, they became in-lodged in the vessels, then the endothelial cells of the blood vessel extended protrusions which surrounded the cell. The endothelial protrusions actively remove the cell from the lumen into the surrounding tissue or nearby vascular cavities. The overall extravasation efficiency for CMMPs was approximately 40% (FIG. 13D) as compared to MPs' failure (0%) to extravasate (FIG. 13D). Such extravasation rate was similar to that from CSCs.

The CMMP technology is generalizable to other cell types. For example, we have demonstrated that we could make CMMPs from mesenchymal stem cells, a commonly used adult stem cell type in clinical trials.

Example 20

Figure 14A:
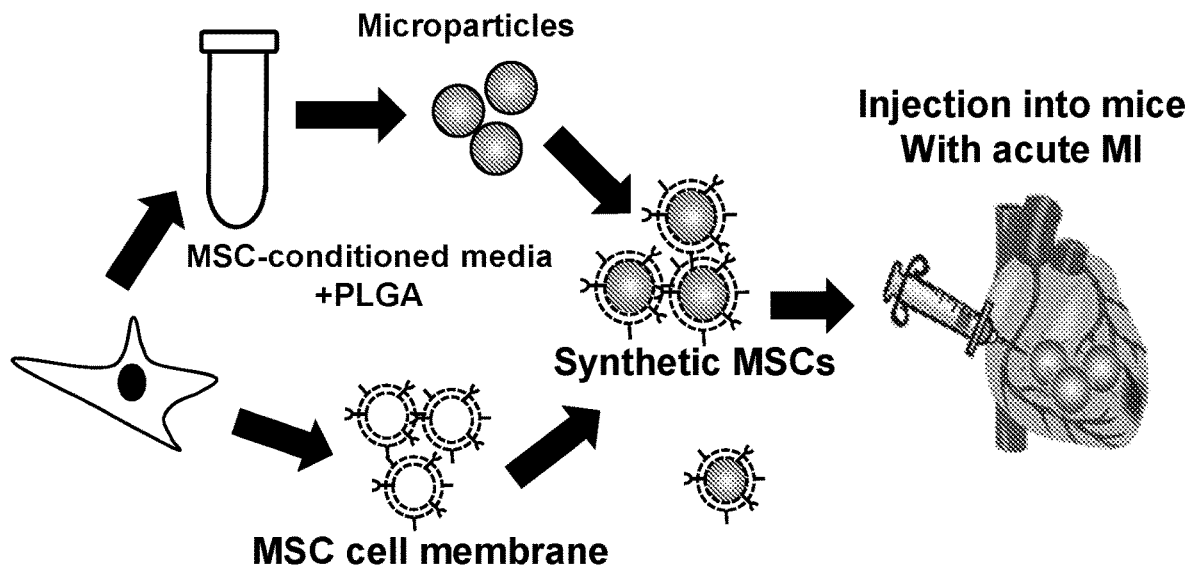
FIGS. 14A-14G illustrate the fabrication and characterization of synthetic mesenchymal stem cells (synMSC).
Figure 14B:
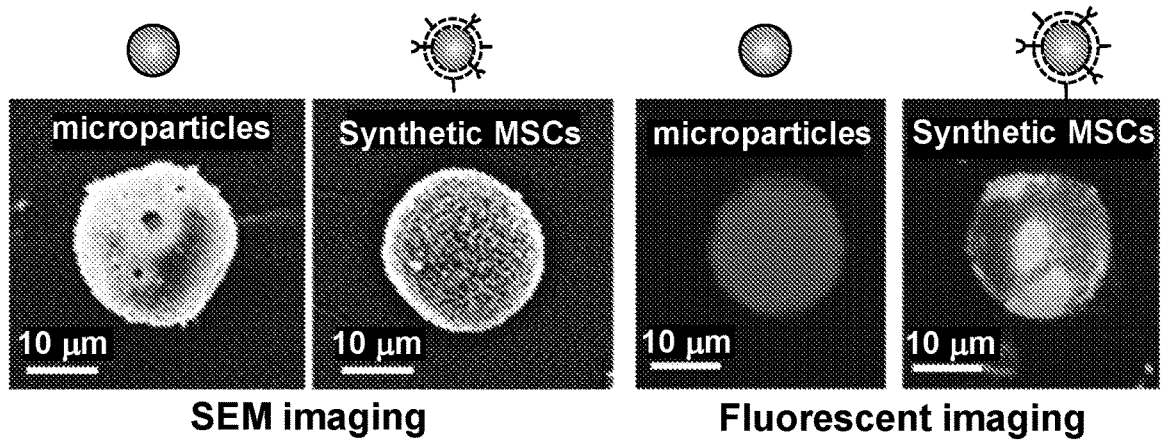
Figure 14C:
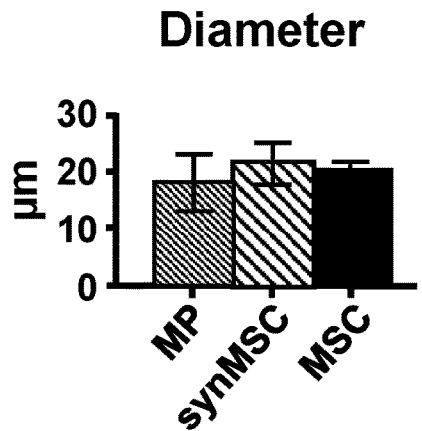
Figure 14D:
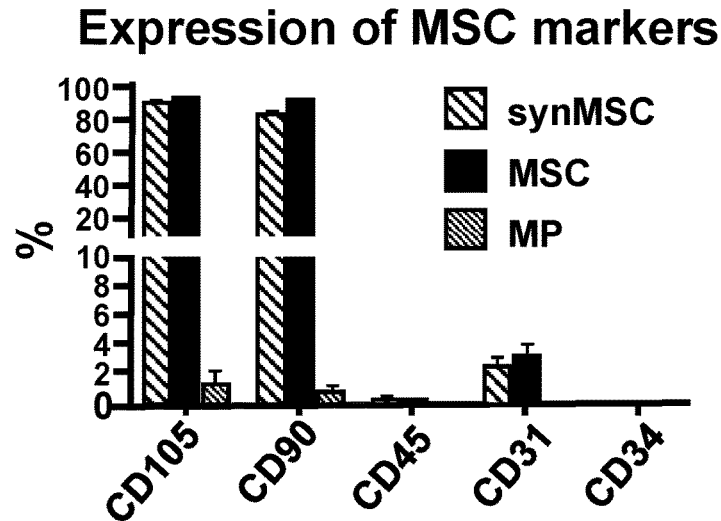
Figure 14E:
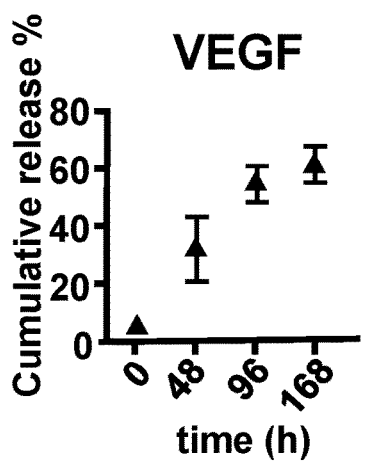
Figure 14F:
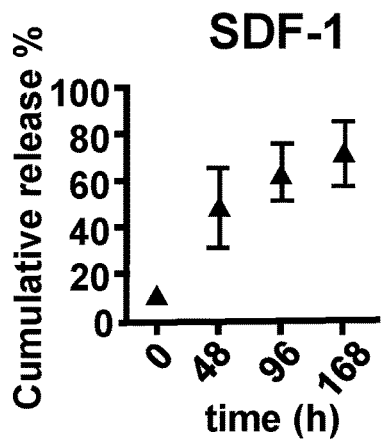
Figure 14G:
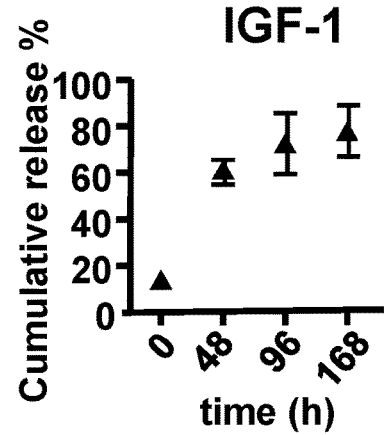

SynMSC Fabrication and Biological Properties:

The schematic design of synMSC fabrication is summarized in FIG. 14A. In brief, MSC-conditioned media was incorporated in PLGA to form microparticles and then the microparticles were coated with MSC cell membrane to form synthetic MSCs (synMSC). Scanning electron microscopy and fluorescent imaging (FIG. 14B) confirmed the successful MSC cell membrane coating on microparticles. synMSC had a size approximately 20 µm, similar to those of microparticles and real MSC (FIG. 14C). Flow cytometry analysis showed that synMSC exhibited similar expressions of CD105, CD90, CD45, CD31, and CD34 compared with MSC, whereas microparticles did not (FIG. 14D). Furthermore, synMSC could sustain the re-lease of growth factors like vascular endothelial growth factor (FIG. 14E), stromal cell-derived factor-1 (FIG. 14F), and insulin-like growth factor 1 (FIG. 14G). These results demonstrated that synMSC and MSC were comparable in terms of secretome and surface antigen expressions.

Example 21 synMSC Promotes Cardiomyocyte Functions In Vitro:

To test the cardiomyocyte protective capability of synMSC in vitro, neonatal rat cardiomyocytes (NRCM, stained by α-sarcomeric actin; FIG. 15A) were co-cultured with microparticles, synMSC and MSC (FIG. 15A). Solitary NRCM culture was included as negative control. synMSC significantly increased NRCM number (FIG. 15B) and promoted NRCM contractility (FIG. 15C). Such beneficial effects were comparable to those from MSC. The promotion of NRCM number and contractility of synMSC might be because of its significantly higher number existed in NRCM (FIG. 15D) although the same amount of particles was originally applied to NRCM. These results demonstrated that the MSC membrane on synMSC allow them to bind and interact with cardiomyocytes.

Example 22

Figure 15H:
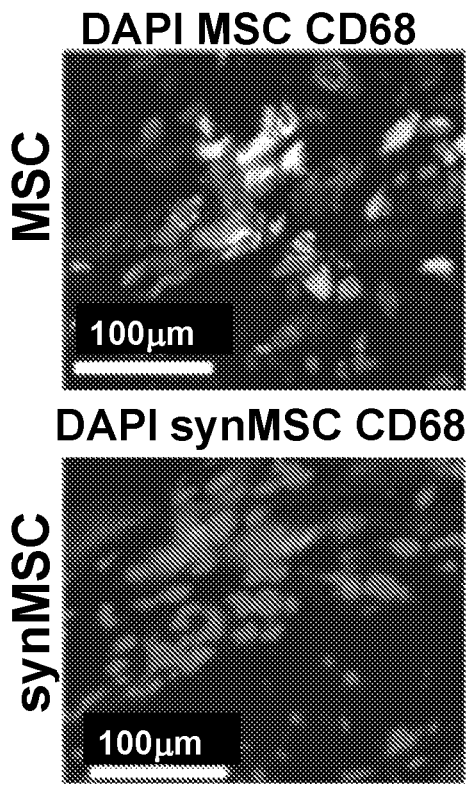
Figure 15H:
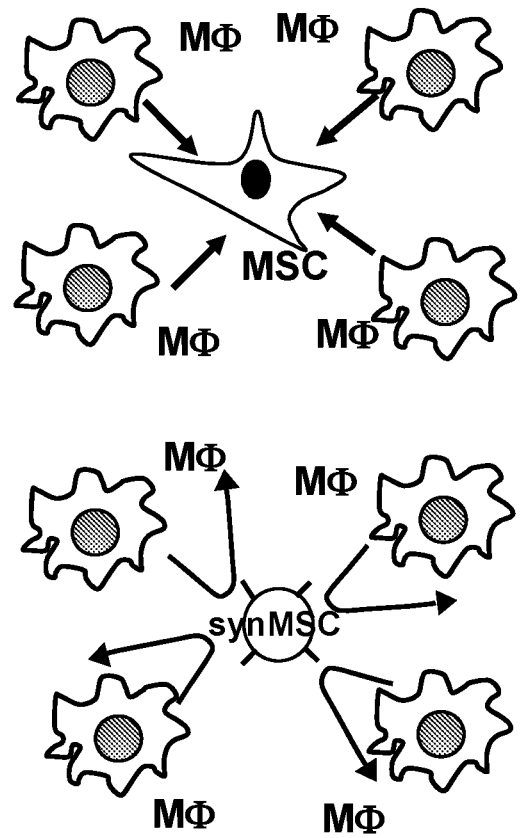
Figure 15I:
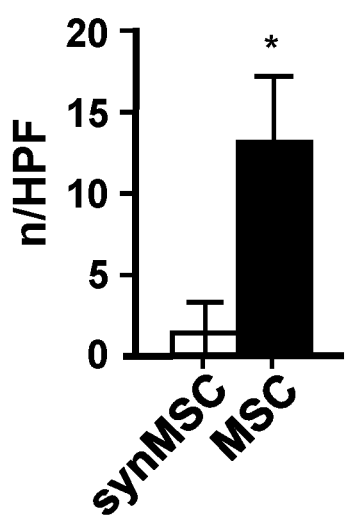

Cryopreservation and Lyophilization Stability of synMSC:

Cryopreservation stability is one of the major challenges of cell therapy products. Here, we tested the stability of synMSC after rapid freezing and thawing. Fluorescent and white light microscopy images revealed that freeze/thaw treatment did not alter the structure (FIG. 15E) or size (FIG. 15F) of synMSC. Flow cytometry analysis showed no significant difference on the surface antigen expressions of synMSC pre- and post-freeze (FIG. 15G). Furthermore, we tested the lyophilization stability of synMSC and found that the lyophilization process did not alter the structure, size, surface antigen expressions, or sustained vascular endothelial growth factor release of synMSC. MSC, however, could not under-go the harsh freeze/thaw process without inducing cell death. After injecting freeze/thawed synMSC or MSC into a mouse heart, MSC were targeted by macrophages while synMSC were not (FIGS. 15H and 15I). These results demonstrated the cryopreservation and lyophilization stability and advantages of synMSC over real MSC.

Example 23 synMSC Injection Mitigates Left Ventricle Remodeling of Infarcted Heart:

To test the therapeutic effect of synMSC, an acute MI model in mice was made by left anterior descending artery ligation and then synMSC were immediately injected intramyocardially. Negative control mice received no treatment after MI.

Figure 16A:
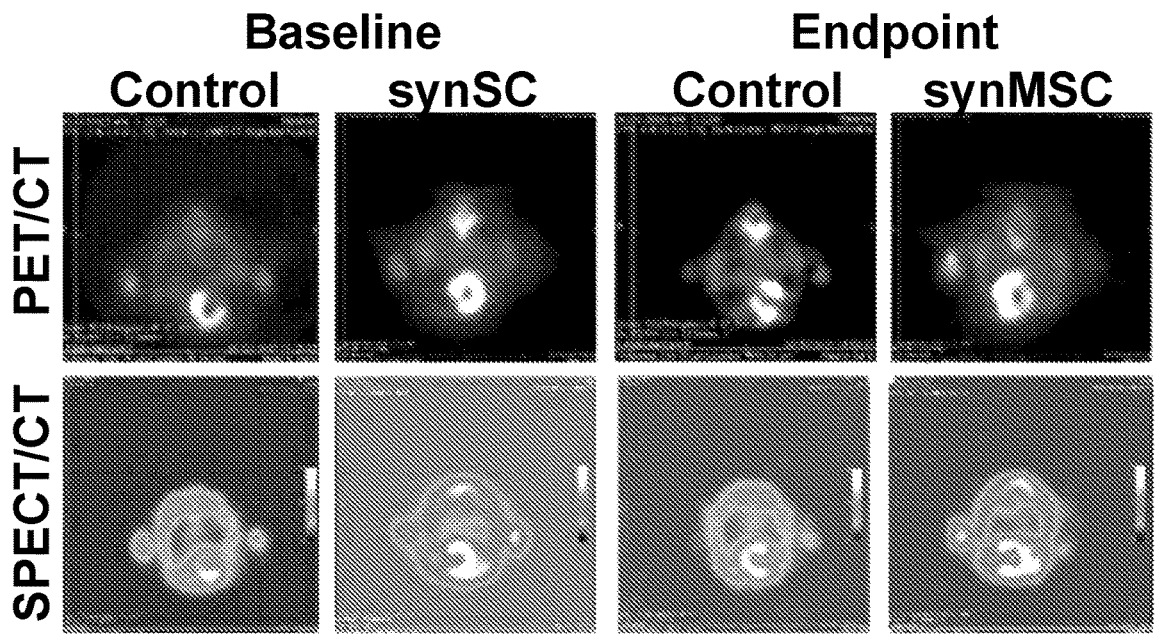
FIGS. 16A-16E illustrates the benefits of synthetic mesenchymal stem cells (synMSC) injection in mice with myocardial infarction.
Figure 16B:
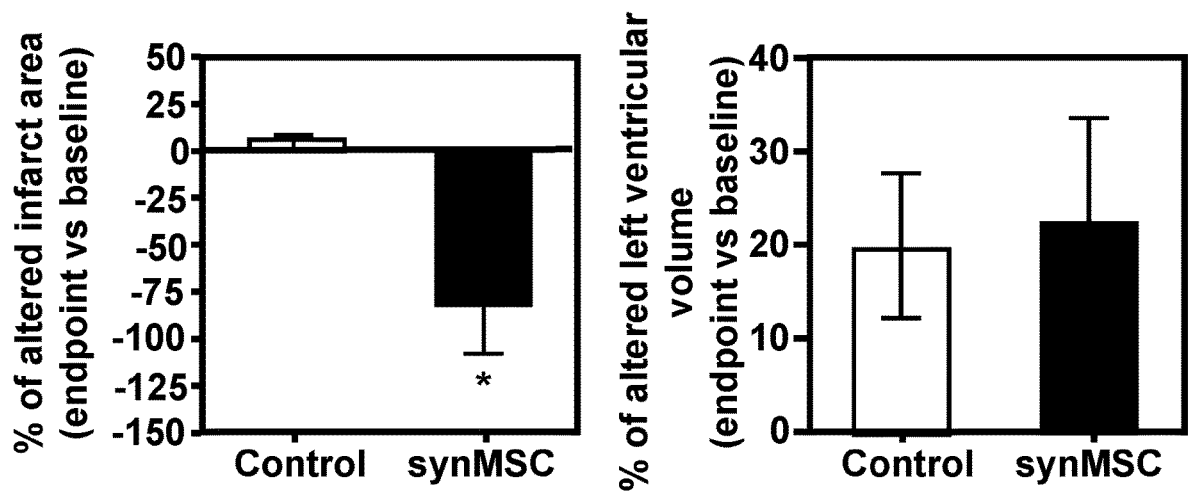
Figure 16C:
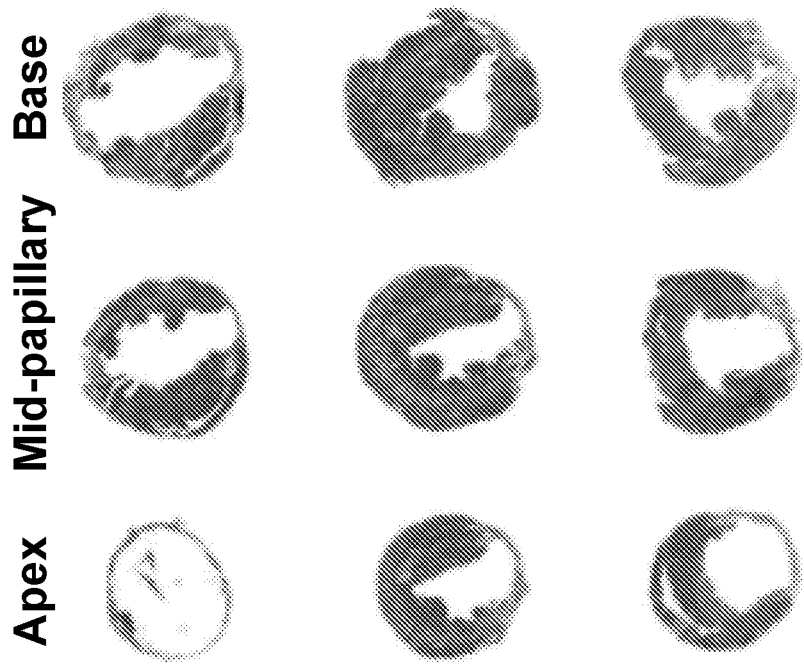
Figure 16D:
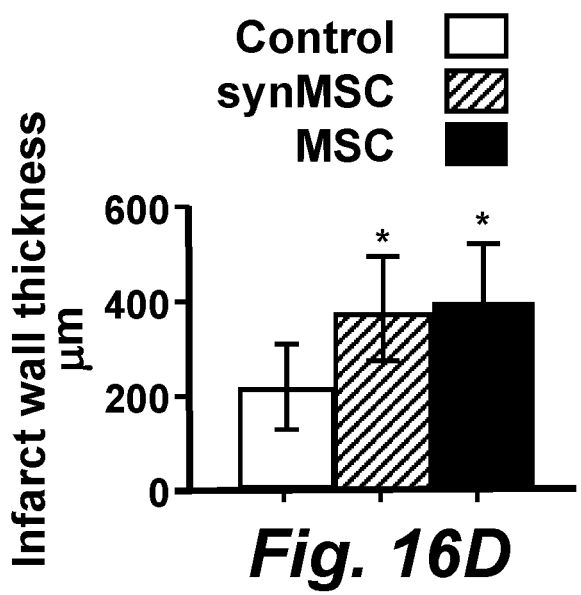
Figure 16E:
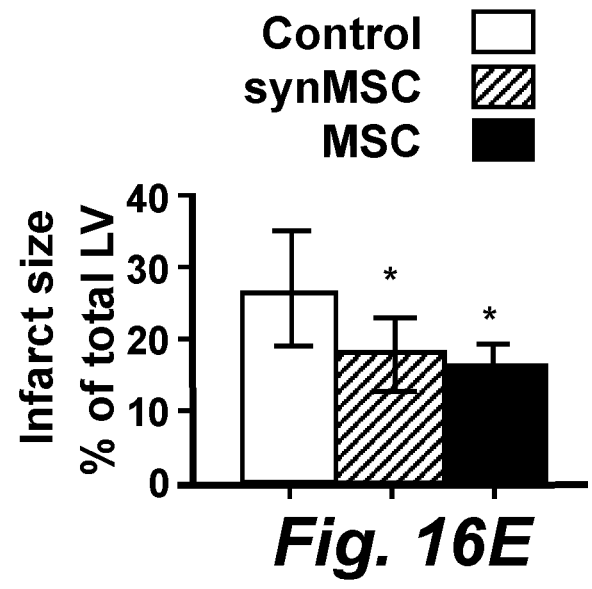

18F-fluorodeoxglucose positron emission tomography/computed tomography (CT) was performed at 1 (baseline) and 14 (end point) days after infarction to measure the infarct area (FIG. 16A). 99mTc-tetrofosmin single photon emission CT/CT was performed at 2 (baseline) and 15 (end point) days after infarction to measure left ventricular volume (FIG. 16A). synMSC injection showed a significant reduction of infarct area (FIG. 16B). The left ventricular volume changes were indistinguishable between the 2 groups (FIG. 16B). Left ventricle morphometry imaged by Masson trichrome staining revealed the protective effects of synMSC and MSC treatment on heart morphology (FIG. 16C). The infarct wall thickness was increased (FIG. 16D) and infarct size was reduced (FIG. 16E) both in synMSC- and MSC-treated mice when compared with the control group.

Figure 17A:
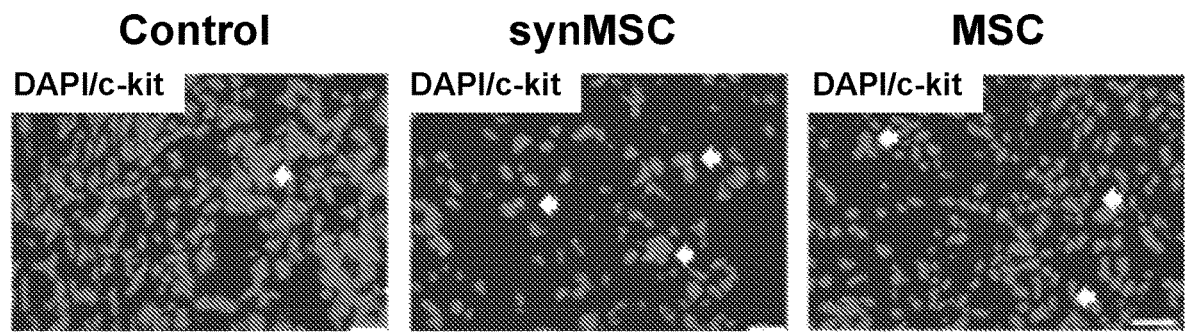
FIGS. 17A-17F illustrate the injection of synthetic mesenchymal stem cells (synMSC) promoted endogenous repair in the infarcted heart.
Figure 17B:
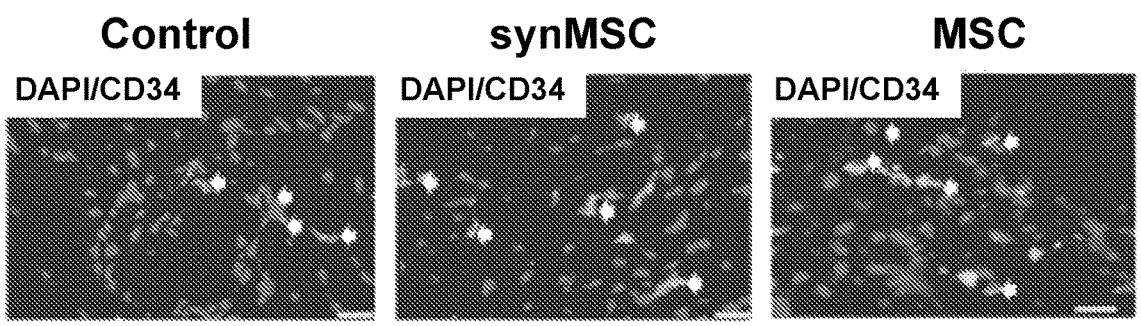
Figure 17C:
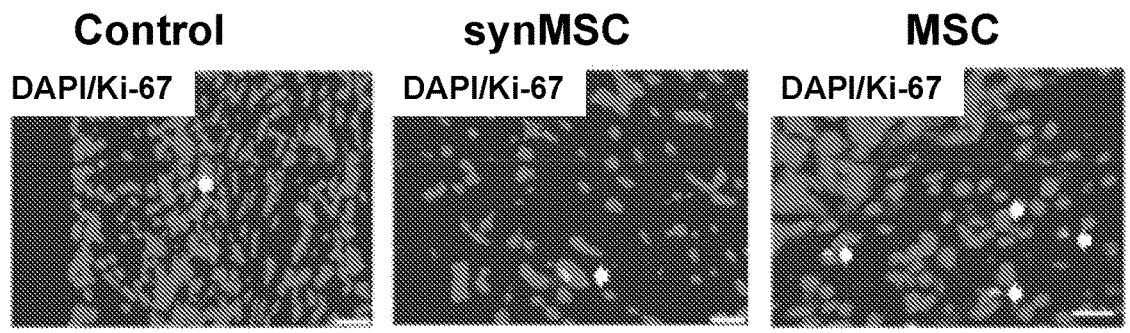
Figure 17F:
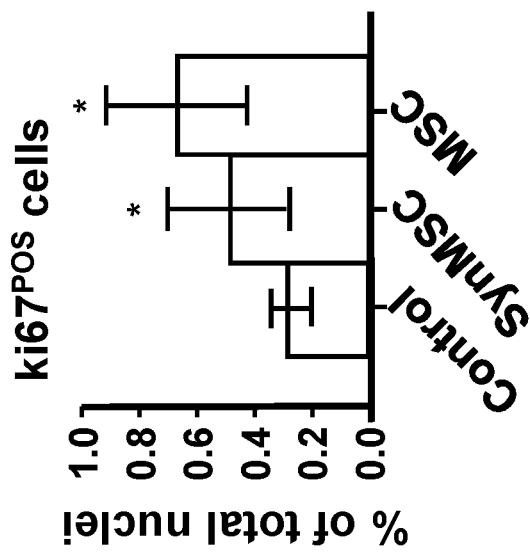
Figure 17E:
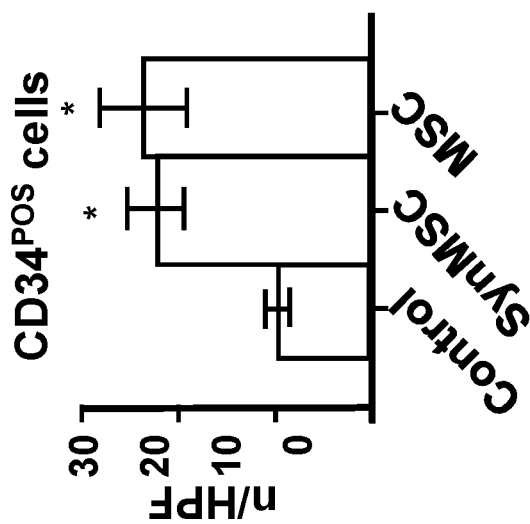
Figure 17D:
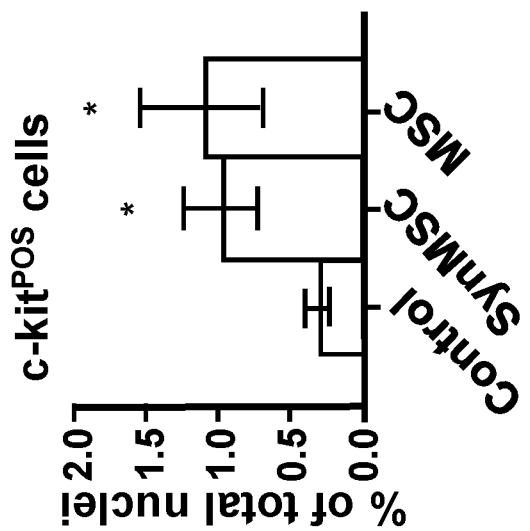

Example 24 synMSC Injection Promotes Endogenous Repair in the Infarcted Heart:

To reveal the mechanisms underlying the therapeutic benefits of synMSC, it was investigated whether synMSC injection could recruit more c-kit-positive stem cells, promote angiogenesis, and improve cell proliferation in the infarcted heart. Immunostaining analyses with c-kit (FIG. 17A), CD34 (FIG. 17B), and ki67 (FIG. 17C) were performed in the infarcted hearts of control, synMSC-, and MSC-treated mice. Compared with control, synMSC and MSC treatments increased the c-kit-positive stem cell recruitment (FIG. 17D) and vessel density (FIG. 17E) of the infarcted heart. Compared with control, the proliferated cells were slightly increased in the infarcted heart of synMSC-treated mice, but significantly increased in the infarcted heart of MSC treated mice (FIG. 17F). These results suggested that the therapeutic effects of synMSC may be through activation of c-kit-positive stem cells and promotion of angiogenesis.

We claim:

1. A stem cell biomimetic microparticle comprising:
   (i) cardiac stem cell-conditioned culture medium or a secretome of a cardiac stem cell embedded in a biocompatible polymer core microparticle; and
   (ii) an outer layer of fragments of cardiac stem cell membranes disposed on the polymer core microparticle, wherein the outer layer of fragments of cardiac stem cell membranes does not significantly alter release profiles of cardiac stem cell factors from the biomimetic microparticles;

wherein the biocompatible polymer core of the microparticle consists of a single species of polymer, a plurality of biocompatible polymer species, a block copolymer, or a plurality of polymer species, and wherein the polymer or polymers of the polymer core are optionally cross-linked.

2. The stem cell biomimetic microparticle of claim 1, wherein the biocompatible polymer core is poly(lactic-co-glycolic acid) (PLGA).

3. A stem cell biomimetic microparticle comprising:
  (i) cardiac stem cell-conditioned culture medium or a secretome of a cardiac stem cell embedded in a biocompatible polymer core microparticle; and
  (ii) an outer layer of fragments of cardiac stem cell membranes disposed on the polymer core microparticle, wherein the outer layer of fragments of cardiac stem cell membranes does not significantly alter release profiles of cardiac stem cell factors from the biomimetic microparticles;

wherein the biocompatible polymer core of the microparticle consists of a single species of polymer, a plurality of biocompatible polymer species, a block copolymer, or a plurality of polymer species, and wherein the polymer or polymers of the polymer core are optionally cross-linked, and wherein the stem cell biomimetic microparticle further comprises a pharmaceutically acceptable carrier.

4. A method of generating a biomimetic microparticle, said method comprising the steps of:
  (a) admixing an aqueous solution comprising a cardiac stem cell-conditioned culture medium or a secretome of a cardiac stem cell with an organic phase having a polymerizable monomer dissolved therein;
  (b) emulsifying the admixture from step (a); and
  (c) admixing the emulsion from step (b) with an aqueous solution and allowing the organic phase to evaporate, thereby generating polymer microparticles comprising the cardiac stem cell-conditioned culture medium or a secretome of a cardiac stem cell embedded therein;
  (d) obtaining an isolated cardiac stem cell membrane or fragments thereof; and
  (e) generating cardiac stem cell membrane-coated biomimetic microparticles by mixing the polymer microparticles from step (c) with the suspension of isolated cardiac stem cell membrane or fragments thereof;

wherein each individual biomimetic microparticle comprises an outer layer of the cardiac stem cell membranes or fragments thereof.

5. A method of tissue repair in a patient in need thereof by delivering to the patient a pharmaceutically acceptable composition comprising a population of stem cell biomimetic microparticles, the microparticles comprising:
  (i) cardiac stem cell-conditioned culture medium or a secretome of a cardiac stem cell embedded in a biocompatible polymer core microparticle; and
  (ii) an outer layer of fragments of cardiac stem cell membranes disposed on the polymer core microparticle, wherein the outer layer of fragments of cardiac stem cell membranes does not significantly alter release profiles of cardiac stem cell factors from the biomimetic microparticles;

wherein the biocompatible polymer core of the microparticle consists of a single species of polymer, a plurality of biocompatible polymer species, a block copolymer, or a plurality of polymer species, and wherein the polymer or polymers of the polymer core are optionally cross-linked.

6. The method of claim 5, wherein the polymer core of the microparticle is biodegradable.

7. The method of claim 5, wherein the polymer core is poly(lactic-co-glycolic acid) (PLGA).

8. The stem cell biomimetic microparticle of claim 1, wherein the release profiles of the cardiac stem cell factors comprises sustained release of the cardiac stem cell factors from about 1 hour to about 168 hours.

9. The stem cell biomimetic microparticle of claim 1, wherein the outer layer of fragments of cardiac stem cell membranes are disposed on a single polymer core microparticle comprising the cardiac stem cell-conditioned culture medium or the secretome of a cardiac stem cell embedded therein.

* * * * *